(12) United States Patent
Desnoyer et al.

(10) Patent No.: US 7,687,460 B2
(45) Date of Patent: Mar. 30, 2010

(54) METHODS OF TREATMENT USING WISP POLYPEPTIDES

(75) Inventors: Luc Desnoyer, San Francisco, CA (US); Ellen H. Filvaroff, San Francisco, CA (US); Diane Pennica, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 10/399,093

(22) PCT Filed: Oct. 12, 2001

(86) PCT No.: PCT/US01/32142

§ 371 (c)(1),
(2), (4) Date: Apr. 14, 2003

(87) PCT Pub. No.: WO02/33085

PCT Pub. Date: Apr. 25, 2002

(65) Prior Publication Data

US 2005/0054563 A1    Mar. 10, 2005

Related U.S. Application Data

(60) Provisional application No. 60/241,222, filed on Oct. 16, 2000.

(51) Int. Cl.
*A61K 38/00* (2006.01)
(52) U.S. Cl. ..................................................... 514/12
(58) Field of Classification Search .................. None
See application file for complete search history.

(56) References Cited

U.S. PATENT DOCUMENTS

| 5,408,040 | A | 4/1995 | Grotendorst et al. | |
|---|---|---|---|---|
| 5,444,047 | A | 8/1995 | DiPasquale | |
| 6,387,657 | B1 * | 5/2002 | Botstein et al. | 435/69.1 |
| 6,812,339 | B1 * | 11/2004 | Venter et al. | 536/24.31 |
| 2002/0192209 | A1 * | 12/2002 | Baker et al. | 424/130.1 |
| 2003/0180891 | A1 * | 9/2003 | Young et al. | 435/69.4 |
| 2003/0199440 | A1 * | 10/2003 | Dack et al. | 514/12 |

FOREIGN PATENT DOCUMENTS

| WO | WO 91/19510 | 12/1991 |
|---|---|---|
| WO | WO 92/13565 | 8/1992 |
| WO | WO 95/17416 | 6/1995 |
| WO | WO 98/21236 | 5/1998 |
| WO | WO 99/21998 | 5/1999 |
| WO | WO 99/62927 | * 9/1999 |
| WO | WO 01/07085 | 2/2001 |
| WO | WO 01/49309 | 7/2001 |

OTHER PUBLICATIONS

J Rudinger. In: Peptide Hormones, JA Parsons, Ed. (1976) 1-7.*

SIGMA. Designing Custom Peptides. http://www.sigma-genosys.com/peptide_design.asp (Accessed Dec. 16, 2004). 2 pages.*
HJC Berendsen. A Glimpse of the Holy Grail? Science (1998) vol. 282, pp. 642-643.*
D Voet and JG Voet. Biochemistry. 2nd edition. (1995) pp. 235-241.*
DE Smilek et al. A single amino acid change in a myelin basic protein peptide confers the capacity to prevent rather than induce experimental autoimmune encephalomyelitis. Proc. Natl. Acad. Sci. USA (1991) Vo. 88, pp. 9633-9637.*
Adany et al., "Altered Expression of Chondroitin Sulfate Proteoglycan in the Stroma of Human Colon Carcinoma" *Journal of Biological Chemistry* 265:11389-11396 (1990).
Amin et al., "The Role of nitric oxide in articular cartilage breakdown in osteoarthritis" *Curr. Opin. Rheum.* 10:263-268 (1998).
Babic AM et al., "CYR61, a product of a growth factor-inducible immediate early gene, promotes angiogenesis and tumor growth" *Proc. Natl. Acad. Sci. USA* 95(11):6355-6360 (May 26, 1998).
Baker, N., "Embryonic and imaginal requirements for wingless, a segment-polarity gene in Drosophila" *Dev. Biol.* 125:96-108 (1988).
Baragi et al., "Transplantation of Adenovirally Transduced Allogeneic Chondrocytes into Articular Cartilage Defects In Vivo." *Osteoarthritis and Cartilage.* 5(4):275-282 (1997).
Baragi et al., "Transplantation of Transduced Chondrocytes Protects Articular Cartilage from Interleukin 1-Induced Extracellular Matrix Degradation" *J. Clin. Invest.* 96(5):2454-2460 (Nov. 1995).
Bradbury et al., "Wnt-4 expression induces a pregnancy-like growth pattern in reconstituted mammary glands in virgin mice" *Dev. Biol.* 170:553-563 (1995).
Bradley and Brown, "The proto-oncogene int-1 encodes a secreted protein associated with the extracellular matrix" *EMBO Journal* 9:1569-1575 (1990).
Brigstock, "The Connective Tissue Growth Factor/Cysteine-Rich 61/Nephroblastoma Overexpressed (CCN) Family" *Endocrine Reviews* 20:189-206 (1999).
Cadigan and Nusse, "Wnt signaling: a common theme in animal development" *Genes & Development* 11(24):3286-3305 (Dec. 15, 1997).
Chen et al., "Chondrocyte Transplantation and Experimental Treatment Options for Articular Cartilage Defects" *Amer. J. Orthop.* 26(6):396-406 (1997).

(Continued)

*Primary Examiner*—Cecilia Tsang
*Assistant Examiner*—Marcela M Cordero Garcia

(57) ABSTRACT

The present invention relates to methods for the treatment and repair of cartilage, including cartilage damaged by injury or degenerative cartilagenous disorders, including arthritis, comprising the administration of WISP polypeptide. Optionally, the administration may be in combination with one or more cartilage agents (e.g., peptide growth factor, catabolism antagonist, osteo-, synovial, anti-inflammatory factor). Alternatively, the method provides for the treatment and repair of cartilage damaged by injury or degenerative cartilagenous disorders comprising the administration of WISP polypeptide in combination with standard surgical techniques. Alternatively, the method provides for the treatment and repair of cartilage damaged by injury or degenerative cartilagenous disorders comprising the administration of chondrocytes previously treated with an effective amount of WISP polypeptide.

17 Claims, 24 Drawing Sheets

OTHER PUBLICATIONS

Chin et al., "Interactions Between Interleukin-1 and Basic Fibroblast Growth Factor on Articular Chondrocytes. Effects on Cell Growth, Prostanoid Production, and Receptor Modulation" *Arthritis Rheum.* 34(3):314-324 (Mar. 1991).

Christiansen et al., "Murine Wnt-11 and Wnt-12 have temporally and spatially restricted expression patterns during embryonic development" *Mech. Dev.* 51(2-3):341-350 (1995).

Coutts et al., "Effect of Growth Factors on Cartilage Repair" *Amer. Acad. Orthop. Surg.* (Instructional Course Lect.), Chapter 47, pp. 487-494 (1997).

Desnoyers et al., "WISP-1 Binds to Decorin and Biglycan" *Journal of Biological Chemistry* 276:47599-47607 (2001).

Desnoyers L. and Pennica D., "Identification of WISP-1 Binding Factors" *1st International Workshop on the CCN Family* (2000).

Dzierzak and Medvinsky, "Mouse embryonic hematopoiesis" *Trends Genet.* 11:359-366 (1995).

Evans and Robbins, "Getting Genes Into Human Synovium" *J. Rheumatol.* 24(11):2061-2063 (1997).

Evans et al., "Blocking Cytokines with Genes" *J. Leukocyte Biol.* 64:55-61 (Jul. 1998).

Fiorini and Roberts, "Effect of Rat Age on Blood Levels of Somatomedin-like Growth Factors" *J. Gerontol.* 35(1):23-30 (1980).

Frazier et al., "Stimulation of Fibroblast Cell Growth, Matrix Production, and Granulation Tissue Formation by Connective Tissue Growth Factor" *J. Invest. Dermatol.* 107:404-411 (1996).

Gavin et al., "Expression of multiple novel Wnt-1/int-1-related genes during fetal and adult mouse development" *Genes Dev.* 4:2319-2332 (1990).

Guerne et al., "Growth Factor Responsiveness of Human Articular Chondrocytes: Distinct Profiles in Primary Chondrocytes, Subcultured Chondrocytes, and Fibroblasts." *J. Cellular Physiology* 158(3):476-484 (1994).

Hashimoto et al., "Expression of the Elm1 gene, a novel gene of the CCN (connective tissue growth factor, Cyr61/Cef10, and neuroblastoma overexpressed gene) family, suppresses In vivo tumor growth and metastasis of K-1735 murine melanoma cells" *Journal of Experimental Medicine* 187(3):289-296 (Feb. 2, 1998).

Herman and Horvitz, "The *Caenorhabditis elegans* gene lin-44 controls the polarity of asymmetric cell divisions" *Development* 120:1035-1047 (1994).

Hill and Logan, "Peptide Growth Factors and their Interactions During Chondrogenesis" *Progress in Growth Factor Research* 4(1):45-68 (1992).

Holland et al., "Gene duplications and the origins of vertebrate development" *Develpment—Supplement* pp. 125-133 (1994).

Holt et al., "Properdin Binds to Sulfatide [Gal (3-SO $^4$β1-1Cer] and Has a Sequence Homology with Other Proteins That Bind Sulfated Glycoconjugates" *Journal of Biological Chemistry* 265:2852-2855 (1990).

Hunziker and Rosenberg, "Induction of Repair in Partial Thickness Articular Cartilage Lesions by Timed Release of TGFβ" (40th Annual Meeting, Orthop. Res. Soc., Feb. 21-24, New Orleans, LA) 19:236-41 (1994).

Hunzlemann et al., "Altered Immunohistochemical Expression of Small Proteoglycans in the Tumor Tissue and Stroma of Basal Cell Carcinoma" *J. Invest. Dermatol.* 104:509-513 (1995).

Hurvitz et al., "Mutations in the CCN gene family member WISP3 cause progressive pseudorheumatoid dysplasia" *Nature Genetics* 23:94-97 (1999).

Kanatsu and Nishikawa, "In vitro analysis of epiblast tissue potency for hematopoietic cell differentiation" *Development* 122:823-830 (1996).

Kang et al., "Ex Vivo Gene Transfer to Chondrocytes in Full-Thickness Articular Cartilage Defects: A Feasibility Study." *Osteoarthritis and Cartilage.* 5(2):139-143 (1997).

Kang et al., "Gene Therapy for Arthritis: Principles and Clinical Practice." *Biochemical Society Transactions.* 25(2):533-537 (1997).

Kim et al., "Identification of a family of low-affinity insulin-like growth factor binding proteins (IGFBPs): Characterization of connective tissue growth factor as a member of the IGFBP superfamily" *Proc. Natl. Acad. Sci. USA* 94(24):12981-12986 (Nov. 25, 1997).

Kireeva et al., "Cyr61, a Product of a Growth Factor-Inducible Immediate-Early Gene, Promotes Cell Proliferation, Migration, and Adhesion" *Molecular & Cellular Biology* 16:1326-1334 (1996).

Klingensmith and Nusse, "Signaling by wingless in *Drosophila*" *Dev. Biol.* 166:396-414 (1994).

Lee et al., "Insertional mutagenesis identifies a member of the Wnt gene family as a candidate oncogene in the mammary epithelium of int-2/Fgf-3 transgenic mice" *Proc. Natl. Acad. Sci.* 92(6):2268-2272 (1995).

Martel-Pelletier et al., "Cytokines and Their Role in the Pathophysiology of Osteoarthritis." *Front. Bioscience.* 4:d694-703 (Oct. 1999).

Martinerie et al., "Regulation of nov by WT1: a potential role for nov in nephrogenesis" *Oncogene* 12(7):1479-1492 (Apr. 4, 1996).

Martinerie et al., "Structural analysis of the human nov proto-oncogene and expression in Wilms tumors" *Oncogene* 9(9):2729-2732 (Sep. 1994).

McMahon and Bradley, "The Wnt-1 (int-1) proto-oncogene is required for development of a large region of the mouse brain" *Cell* 62:1073-1085 (1990).

McMahon, A., "The Wnt Family of Developmental Regulators" *Trends in Genetics* 8(7):236-242 (1992).

Morata and Lawrence, "The development of wingless, a homeotic mutation of *Drosophila*" *Dev. Biol.* 56:227-240 (1977).

Nusse and Varmus, "Many tumors induced by the mouse mammary tumor virus contain a provirus integrated in the same region of the host genome" *Cell* 31:99-109 (1982).

Nusse and Varmus, "Wnt genes" *Cell* 69:1073-1087 (1992).

Oemar and Luscher, "Connective tissue growth factor. Friend or foe?" *Arteriosclerosis, Thrombosis & Vascular Biology* 17(8):1483-1489 (Aug. 1997).

Osborn et al., "Growth Factor Stimulation of Adult Articular Cartilage" *J. Orthoped. Res.* 7(1):35-42 (1989).

Papkoff and Schryver, "Secreted int-1 protein is associated with the cell surface" *Mole. Cell. Biol.* 10:2723-2730 (1990).

Parr and McMahon, "Dorsalizing signal Wnt-7a required for normal polarity of D-V and A-P axes of mouse limb" *Nature* 374:350-353 (1995).

Pennica D, et al., "WISP genes are members of the connective tissue growth factor family that are up-regulated in wnt-1-transformed cells and aberrantly expressed in human colon tumors" *Proc. Acad. Sci. USA* 95(25):14717-14722 (Dec. 8, 1998).

Rijsewik et al., "The *Drosophila* Homolog of the Mouse Mammary Oncogene int-1 Is Identical to the Segment Polarity Gene wingless" *Cell* 50:649-657 (1987).

Rogachefsky et al., "Treatment of Canine Osteoarthritis with Sodium Pentosan Polysulfate and Insulin-Like Growth Factor-1" *Ann. NY Acad. Sci.* pp. 392-394 (1994).

Sah et al., "Differential Effects of bFGF and IGF-1 on Matrix Metabolism in Calf and Adult Bovine Cartilage Explants" *Arch. Biochem. and Biophys.*, Academic Press, Inc. vol. 308(1):137-147 (1994).

Sato and Urist., "Bone Morphogenetic Protein-Induced Cartilage Development in Tissue Culture." *Clin. Ortho. Rel. Res.* (Sect. II, Basic Science and Pathology) 183:180-187 (Mar. 1984).

Stander et al., "Decorin gene transfer-mediated suppression of TGF-β synthesis abrogates experimental malignant glioma growth in vivo" *Gene Therapy* 5:1187-1194 (1998).

Stark et al., "Epithelial transformation of metanephric mesenchyme in the developing kidney regulated by Wnt-4" *Nature* 372:679-683 (1994).

Takada et al., "Wnt-3a regulates somite and tailbud formation in the mouse embryo" *Genes Dev.* 8:174-189 (1994).

Thomas and Cappechi, "Targeted disruption of the murine int-1 proto-oncogene resulting in severe abnormalities in midbrain and cerebellar development" *Nature* 346:847-850 (1990).

Toolan et al., "Development of Novel Osteochondral Graft for Cartilage Repair." *J. Biomed. Mater. Res.* 41(2):244-250 (1998).

van Beuningen et al., "Protection From Interleukin 1 Induced Destruction of Articular Cartilage by Transforming Growth Factor β: Studies in Anatomically Intact Cartilage In Vitro and In Vivo." *Annals of Rheum. Diseases.* 52(3):185-191 (1993).

van der Kraan et al., "Inhibition of Proteoglycan Synthesis by Transforming Growth Factor β in Anatomically Intact Articular Cartilage of Murine Patellae" *Annals Rheum. Dis.* 51(5):643-647 (1992).

Vant Veer et al., "Molecular cloning and chromosomal assignment of the human homolog of int-1, a mouse gene implicated in mammary tumorigenesis" *Mole. Cell. Biol.* 4:2532-2534 (1984).

Xu et al., "WISP-1 is a Wnt-l- and β-catenin-responsive oncogene" *Gene & Develop.* 14:585-595 (2000).

Yamanaka et al., "Inhibition of insulin receptor activation by insulin-like growth factor binding proteins" *Journal of Biological Chemistry* 272(49):30729-30734 (Dec. 5, 1997).

Yang et al., "Cyr61, Product of a Growth Factor-inducible Immediate Early Gene, Is Associated with the Extracellular Matrix and the Cell Surface" *Cell. Growth Diff* 2:351-357 (1991).

Zhang R et al., "Identification of rCop-1, a new member of the CCN protein family, as a negative regulator for cell transformation" *Mol Cell Biol* 18(10):6131-6141 (Oct. 1998).

Zon et al., "The zebrafish: a new model for studying embryonic hematopoiesis" *Collogue, INSERM,* Gluckman and Coulombel, eds. vol. 235:17-22 (1995).

Kumar, S. et al., "Identification and Cloning of a Connective Tissue Growth Factor-like cDNA from Human Osteoblasts Encoding a Novel Regulator of Osteoblast Functions" *The Journal of Biological Chemistry* 274(24):17123-17131 (Jul. 11, 1999).

* cited by examiner

Cell Binding with WISP-1

Hs 597.Sk (Hum. normal skin fibroblasts)
Hs 839.T (Hum. skin melanoma fibroblasts)
Hs 908.Sk (Hum. skin melanoma fibroblasts)
NRK (Normal rat kidney fibroblasts)

RAG (Mouse kidney adenocarcinoma)
COLO 320 DM (Hum. colon adenocarcinoma)
293 (Hum. kidney epithelial)
HUVEC (Hum. umbilical vein endothelial)
WM-266-4 (Hum. skin melanoma epithelial)

Negative Control

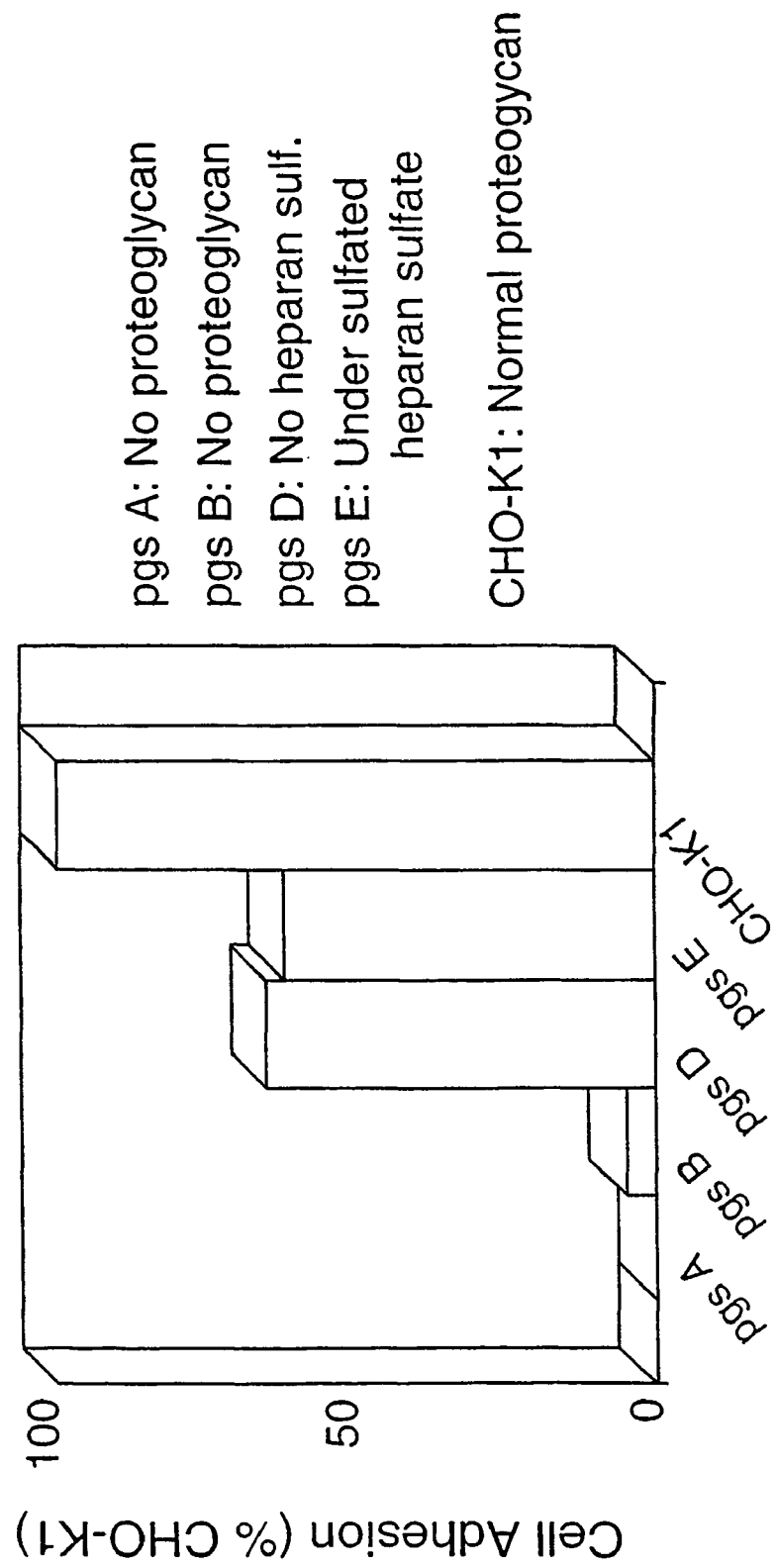

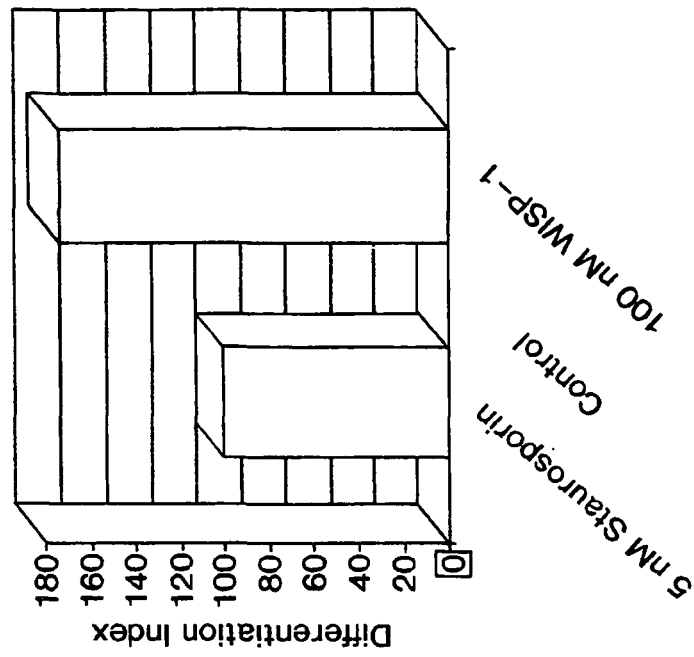
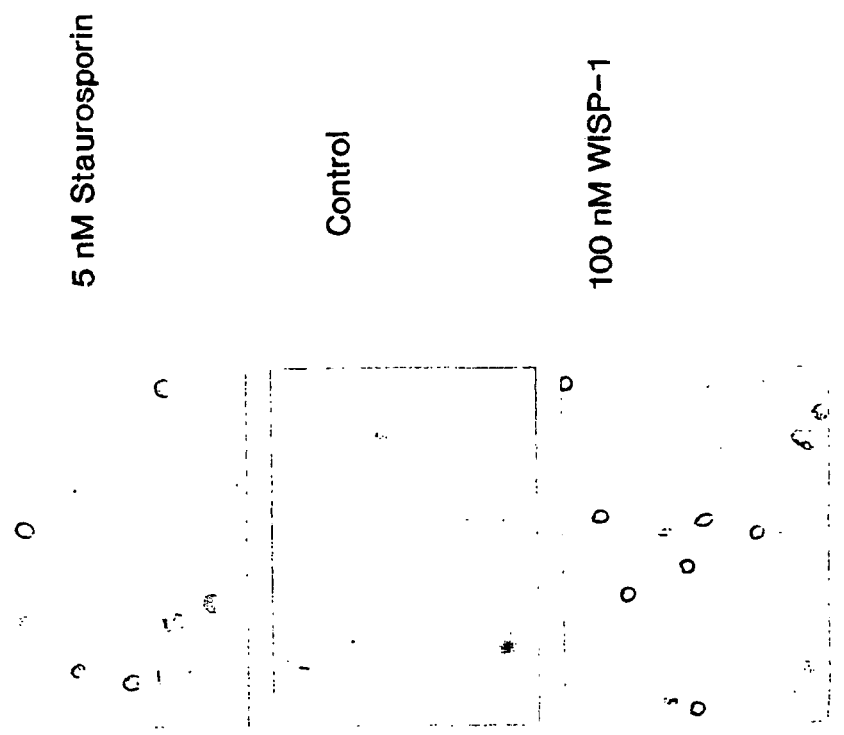
FIG. 12
WISP-1 Induces Chondrocyte Differentiation

WISP-1 Sequences

Constructs Sequences

PIN 414
DNA 43059
HUMAN WISP-1-IgG

SEQ ID 1:
```
MRWFLPWTLAAVTAAAASTVLATALSPAPTTMDFTPAPLEDTSSRPQFCKWPCECPPSPP
RCPLGVSLITDGCECCKMCAQQLGDNCTEAAICDPHRGLYCDYSGDRPRYAIGVCAQVVG
VGCVLDGVRYNNGQSFQPNCKYNCTCIDGAVGCTPLCLRVRPPRLWCPHPRRVSIPGHCC
EQWVCEDDAKRPRKTAPRDTGAFDAVGEVEAWHRNCIAYTSPWSPCSTSCGLGVSTRISN
VNAQCWPEQESRLCNLRPCDVDIHTLIKAGKKCLAVYQPEASMNFTLAGCISTRSYQPKY
CGVCMDNRCCIPYKSKTIDVSFQCPDGLGFSRQVLWINACFCNLSCRNPNDIFADLESYP
DFSEIANPDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAPI
EKTISKAKGQPREPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSLSLSPGK
```

MOUSE WISP-1-IgG

SEQ ID 2:
```
MRWLLPWTLAAVAVLRVGNILATALSPTPTTMTFTPAPLEETTTRPEFCKWPCECPQSPP
RCPLGVSLITDGCECCKICAQQLGDNCTEAAICDPHRGLYCDYSGDRPRYAIGVCAQVVG
VGCVLDGVRYTNGESFQPNCRYNCTCIDGTVGCTPLCLSPRPPRLWCRQPRHVRVPGQCC
EQWVCDDDARRPRQTALLDTRAFAASGAVEQRYENCIAYTSPWSPCSTTCGLGISTRISN
VNARCWPEQESRLCNLRPCDVDIQLHIKAGKKCLAVYQPEEATNFTLAGCVSTRTYRPKY
CGVCTDNRCCIPYKSKTISVDFQCPEGPGFSRQVLWINACFCNLSCRNPNDIFADLESYP
DFEEIANPDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAPI
EKTISKAKGQPREPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSLSLSPGK
```

"Wild Type" Sequences:

HUMAN WISP-1

SEQ ID 3:
```
MRWFLPWTLAAVTAAAASTVLATALSPAPTTMDFTPAPLEDTSSRPQFCKWPCECPPSPP
RCPLGVSLITDGCECCKMCAQQLGDNCTEAAICDPHRGLYCDYSGDRPRYAIGVCAQVVG
VGCVLDGVRYNNGQSFQPNCKYNCTCIDGAVGCTPLCLRVRPPRLWCPHPRRVSIPGHCC
EQWVCEDDAKRPRKTAPRDTGAFDAVGEVEAWHRNCIAYTSPWSPCSTSCGLGVSTRISN
VNAQCWPEQESRLCNLRPCDVDIHTLIKAGKKCLAVYQPEASMNFTLAGCISTRSYQPKY
CGVCMDNRCCIPYKSKTIDVSFQCPDGLGFSRQVLWINACFCNLSCRNPNDIFADLESYP
DFSEIAN
```

MOUSE WISP-1

SEQ ID 4:
```
MRWLLPWTLAAVAVLRVGNILATALSPTPTTMTFTPAPLEETTTRPEFCKWPCECPQSPP
RCPLGVSLITDGCECCKICAQQLGDNCTEAAICDPHRGLYCDYSGDRPRYAIGVCAQVVG
VGCVLDGVRYTNGESFQPNCRYNCTCIDGTVGCTPLCLSPRPPRLWCRQPRHVRVPGQCC
EQWVCDDDARRPRQTALLDTRAFAASGAVEQRYENCIAYTSPWSPCSTTCGLGISTRISN
VNARCWPEQESRLCNLRPCDVDIQLHIKAGKKCLAVYQPEEATNFTLAGCVSTRTYRPKY
CGVCTDNRCCIPYKSKTISVDFQCPEGPGFSRQVLWINACFCNLSCRNPNDIFADLESYP
DFEEIAN
```

HUMAN IgG tag

SEQ ID 5:
```
PDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAPI
EKTISKAKGQPREPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSLSLSPGK
```

FIG. 17

WISP-3 IgG
></usr/seqdb2/sst/DNA/Dnaseqs.full/ss.DNA59535
><subunit 1 of 1, 600 aa, 1 stop
><MW: 67062, pI: 8.82, NX(S/T): 3

SEQ ID 6
{
MNKRRLLYPSGWLHGPSDMQGLLFSTLLLAGLAQFCCRVQGTGPLDTTPEGRPGEVSDAP
QRKQFCHWPCKCPQQKPRCPPGVSLVRDGCGCCKICAKQPGEICNEADLCDPHKGLYCDY
SVDRPRYETGVCAYLVAVGCEFNQVHYHNGQVFQPNPLFSCLCVSGAIGCTPLFIPKLAG
SHCSGAKGGKKSDQSNCSLEPLLQQLSTSYKTMPAYRDLPLIWKKKCLVQATKWTPCSRT
CGMGISNRVTNENSNCEMRKEKRLCYIQPCDSNILKTIKIPKGKTCQPTFQLSKAEKFVF
SGCSSTQSYKPTFCGICLDKRCCIPNKSKMITIQFDCPNEGSFKWKMLWITSCVCQRNCR
EPGDIFSELKILPDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHYTQKSLSLSPGK
} alternate WISP3-IgG
></usr/seqdb2/sst/DNA/Dnaseqs.full/ss.DNA59533
><subunit 1 of 1, 582 aa, 1 stop
><MW: 64952, pI: 8.79, NX(S/T): 3

SEQ ID 7
{
MQGLLFSTLLLAGLAQFCCRVQGTGPLDTTPEGRPGEVSDAPQRKQFCHWPCKCPQQKPR
CPPGVSLVRDGCGCCKICAKQPGEICNEADLCDPHKGLYCDYSVDRPRYETGVCAYLVAV
GCEFNQVHYHNGQVFQPNPLFSCLCVSGAIGCTPLFIPKLAGSHCSGAKGGKKSDQSNCS
LEPLLQQLSTSYKTMPAYRNLPLIWKKKCLVQATKWTPCSRTCGMGISNRVTNENSNCEM
RKEKRLCYIQPCDSNILKTIKIPKGKTCQPTFQLSKAEKFVFSGCSSTQSYKPTFCGICL
DKRCCIPNKSKMITIQFDCPNEGSFKWKMLWITSCVCQRNCREPGDIFSELKILPDKTHT
CPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSFF
LYSKLTVDKSRWQQGNVFSCSVMHEALHNHYTQKSLSLSPGK
}

WISP3
></usr/seqdb2/sst/DNA/Dnaseqs.full/ss.DNA58800
><subunit 1 of 1, 354 aa, 1 stop
><MW: 39293, pI: 8.93, NX(S/T): 2

SEQ ID 8
{
MQGLLFSTLLLAGLAQFCCRVQGTGPLDTTPEGRPGEVSDAPQRKQFCHWPCKCPQQKPR
CPPGVSLVRDGCGCCKICAKQPGEICNEADLCDPHKGLYCDYSVDRPRYETGVCAYLVAV
GCEFNQVHYHNGQVFQPNPLFSCLCVSGAIGCTPLFIPKLAGSHCSGAKGGKKSDQSNCS
LEPLLQQLSTSYKTMPAYRNLPLIWKKKCLVQATKWTPCSRTCGMGISNRVTNENSNCEM
RKEKRLCYIQPCDSNILKTIKIPKGKTCQPTFQLSKAEKFVFSGCSSTQSYKPTFCGICL
DKRCCIPNKSKMITIQFDCPNEGSFKWKMLWITSCVCQRNCREPGDIFSELKIL
}

WISP3 " long 5' splicing"
></usr/seqdb2/sst/DNA/Dnaseqs.full/ss.DNA56350
><subunit 1 of 1, 372 aa, 1 stop
><MW: 41403, pI: 8.96, NX(S/T): 2

SEQ ID 9
{
MNKRRLLYPSGWLHGPSDMQGLLFSTLLLAGLAQFCCRVQGTGPLDTTPEGRPGEVSDAP
QRKQFCHWPCKCPQQKPRCPPGVSLVRDGCGCCKICAKQPGEICNEADLCDPHKGLYCDY
SVDRPRYETGVCAYLVAVGCEFNQVHYHNGQVFQPNPLFSCLCVSGAIGCTPLFIPKLAG
SHCSGAKGGKKSDQSNCSLEPLLQQLSTSYKTMPAYRDLPLIWKKKCLVQATKWTPCSRT
CGMGISNRVTNENSNCEMRKEKRLCYIQPCDSNILKTIKIPKGKTCQPTFQLSKAEKFVF
SGCSSTQSYKPTFCGICLDKRCCIPNKSKMITIQFDCPNEGSFKWKMLWITSCVCQRNCR
EPGDIFSELKIL

SEQUENCE LISTING

<160> NUMBER OF SEQ ID NOS: 10

<210> SEQ ID NO 1
<211> LENGTH: 595
<212> TYPE: PRT
<213> ORGANISM: homo sapien

<400> SEQUENCE: 1

```
Met Arg Trp Phe Leu Pro Trp Thr Leu Ala Ala Val Thr Ala Ala
 1               5                  10                  15

Ala Ala Ser Thr Val Leu Ala Thr Ala Leu Ser Pro Ala Pro Thr
                20                  25                  30

Thr Met Asp Phe Thr Pro Ala Pro Leu Glu Asp Thr Ser Ser Arg
                35                  40                  45

Pro Gln Phe Cys Lys Trp Pro Cys Glu Cys Pro Pro Ser Pro Pro
                50                  55                  60

Arg Cys Pro Leu Gly Val Ser Leu Ile Thr Asp Gly Cys Glu Cys
                65                  70                  75

Cys Lys Met Cys Ala Gln Gln Leu Gly Asp Asn Cys Thr Glu Ala
                80                  85                  90

Ala Ile Cys Asp Pro His Arg Gly Leu Tyr Cys Asp Tyr Ser Gly
                95                 100                 105

Asp Arg Pro Arg Tyr Ala Ile Gly Val Cys Ala Gln Val Val Gly
               110                 115                 120

Val Gly Cys Val Leu Asp Gly Val Arg Tyr Asn Asn Gly Gln Ser
               125                 130                 135
```

-continued

```
Phe Gln Pro Asn Cys Lys Tyr Asn Cys Thr Cys Ile Asp Gly Ala
                140                 145                 150
Val Gly Cys Thr Pro Leu Cys Leu Arg Val Arg Pro Arg Leu
            155                 160                 165
Trp Cys Pro His Pro Arg Arg Val Ser Ile Pro Gly His Cys Cys
        170                 175                 180
Glu Gln Trp Val Cys Glu Asp Asp Ala Lys Arg Pro Arg Lys Thr
                185                 190                 195
Ala Pro Arg Asp Thr Gly Ala Phe Asp Ala Val Gly Glu Val Glu
                200                 205                 210
Ala Trp His Arg Asn Cys Ile Ala Tyr Thr Ser Pro Trp Ser Pro
                215                 220                 225
Cys Ser Thr Ser Cys Gly Leu Gly Val Ser Thr Arg Ile Ser Asn
                230                 235                 240
Val Asn Ala Gln Cys Trp Pro Glu Gln Glu Ser Arg Leu Cys Asn
                245                 250                 255
Leu Arg Pro Cys Asp Val Asp Ile His Thr Leu Ile Lys Ala Gly
                260                 265                 270
Lys Lys Cys Leu Ala Val Tyr Gln Pro Glu Ala Ser Met Asn Phe
                275                 280                 285
Thr Leu Ala Gly Cys Ile Ser Thr Arg Ser Tyr Gln Pro Lys Tyr
                290                 295                 300
Cys Gly Val Cys Met Asp Asn Arg Cys Cys Ile Pro Tyr Lys Ser
                305                 310                 315
Lys Thr Ile Asp Val Ser Phe Gln Cys Pro Asp Gly Leu Gly Phe
                320                 325                 330
Ser Arg Gln Val Leu Trp Ile Asn Ala Cys Phe Cys Asn Leu Ser
                335                 340                 345
Cys Arg Asn Pro Asn Asp Ile Phe Ala Asp Leu Glu Ser Tyr Pro
                350                 355                 360
Asp Phe Ser Glu Ile Ala Asn Pro Asp Lys Thr His Thr Cys Pro
                365                 370                 375
Pro Cys Pro Ala Pro Glu Leu Leu Gly Gly Pro Ser Val Phe Leu
                380                 385                 390
Phe Pro Pro Lys Pro Lys Asp Thr Leu Met Ile Ser Arg Thr Pro
                395                 400                 405
Glu Val Thr Cys Val Val Val Asp Val Ser His Glu Asp Pro Glu
                410                 415                 420
Val Lys Phe Asn Trp Tyr Val Asp Gly Val Glu Val His Asn Ala
                425                 430                 435
Lys Thr Lys Pro Arg Glu Glu Gln Tyr Asn Ser Thr Tyr Arg Val
                440                 445                 450
Val Ser Val Leu Thr Val Leu His Gln Asp Trp Leu Asn Gly Lys
                455                 460                 465
Glu Tyr Lys Cys Lys Val Ser Asn Lys Ala Leu Pro Ala Pro Ile
                470                 475                 480
Glu Lys Thr Ile Ser Lys Ala Lys Gly Gln Pro Arg Glu Pro Gln
                485                 490                 495
Val Tyr Thr Leu Pro Pro Ser Arg Glu Glu Met Thr Lys Asn Gln
                500                 505                 510
Val Ser Leu Thr Cys Leu Val Lys Gly Phe Tyr Pro Ser Asp Ile
                515                 520                 525
```

```
Ala Val Glu Trp Glu Ser Asn Gly Gln Pro Glu Asn Asn Tyr Lys
            530                 535                 540

Thr Thr Pro Pro Val Leu Asp Ser Asp Gly Ser Phe Phe Leu Tyr
            545                 550                 555

Ser Lys Leu Thr Val Asp Lys Ser Arg Trp Gln Gln Gly Asn Val
            560                 565                 570

Phe Ser Cys Ser Val Met His Glu Ala Leu His Asn His Tyr Thr
            575                 580                 585

Gln Lys Ser Leu Ser Leu Ser Pro Gly Lys
            590                 595

<210> SEQ ID NO 2
<211> LENGTH: 595
<212> TYPE: PRT
<213> ORGANISM: mus musculus

<400> SEQUENCE: 2

Met Arg Trp Leu Leu Pro Trp Thr Leu Ala Ala Val Ala Val Leu
 1               5                  10                  15

Arg Val Gly Asn Ile Leu Ala Thr Ala Leu Ser Pro Thr Pro Thr
                20                  25                  30

Thr Met Thr Phe Thr Pro Ala Pro Leu Glu Glu Thr Thr Thr Arg
                35                  40                  45

Pro Glu Phe Cys Lys Trp Pro Cys Glu Cys Pro Gln Ser Pro Pro
                50                  55                  60

Arg Cys Pro Leu Gly Val Ser Leu Ile Thr Asp Gly Cys Glu Cys
                65                  70                  75

Cys Lys Ile Cys Ala Gln Gln Leu Gly Asp Asn Cys Thr Glu Ala
                80                  85                  90

Ala Ile Cys Asp Pro His Arg Gly Leu Tyr Cys Asp Tyr Ser Gly
                95                  100                 105

Asp Arg Pro Arg Tyr Ala Ile Gly Val Cys Ala Gln Val Val Gly
                110                 115                 120

Val Gly Cys Val Leu Asp Gly Val Arg Tyr Thr Asn Gly Glu Ser
                125                 130                 135

Phe Gln Pro Asn Cys Arg Tyr Asn Cys Thr Cys Ile Asp Gly Thr
                140                 145                 150

Val Gly Cys Thr Pro Leu Cys Leu Ser Pro Arg Pro Arg Leu
                155                 160                 165

Trp Cys Arg Gln Pro Arg His Val Arg Val Pro Gly Gln Cys Cys
                170                 175                 180

Glu Gln Trp Val Cys Asp Asp Asp Ala Arg Arg Pro Arg Gln Thr
                185                 190                 195

Ala Leu Leu Asp Thr Arg Ala Phe Ala Ala Ser Gly Ala Val Glu
                200                 205                 210

Gln Arg Tyr Glu Asn Cys Ile Ala Tyr Thr Ser Pro Trp Ser Pro
                215                 220                 225

Cys Ser Thr Thr Cys Gly Leu Gly Ile Ser Thr Arg Ile Ser Asn
                230                 235                 240

Val Asn Ala Arg Cys Trp Pro Glu Gln Glu Ser Arg Leu Cys Asn
                245                 250                 255

Leu Arg Pro Cys Asp Val Asp Ile Gln Leu His Ile Lys Ala Gly
                260                 265                 270

Lys Lys Cys Leu Ala Val Tyr Gln Pro Glu Glu Ala Thr Asn Phe
                275                 280                 285
```

-continued

```
Thr Leu Ala Gly Cys Val Ser Thr Arg Thr Tyr Arg Pro Lys Tyr
            290                 295                 300

Cys Gly Val Cys Thr Asp Asn Arg Cys Cys Ile Pro Tyr Lys Ser
            305                 310                 315

Lys Thr Ile Ser Val Asp Phe Gln Cys Pro Glu Gly Pro Gly Phe
            320                 325                 330

Ser Arg Gln Val Leu Trp Ile Asn Ala Cys Phe Cys Asn Leu Ser
            335                 340                 345

Cys Arg Asn Pro Asn Asp Ile Phe Ala Asp Leu Glu Ser Tyr Pro
            350                 355                 360

Asp Phe Glu Glu Ile Ala Asn Pro Asp Lys Thr His Thr Cys Pro
            365                 370                 375

Pro Cys Pro Ala Pro Glu Leu Leu Gly Gly Pro Ser Val Phe Leu
            380                 385                 390

Phe Pro Pro Lys Pro Lys Asp Thr Leu Met Ile Ser Arg Thr Pro
            395                 400                 405

Glu Val Thr Cys Val Val Val Asp Val Ser His Glu Asp Pro Glu
            410                 415                 420

Val Lys Phe Asn Trp Tyr Val Asp Gly Val Glu Val His Asn Ala
            425                 430                 435

Lys Thr Lys Pro Arg Glu Glu Gln Tyr Asn Ser Thr Tyr Arg Val
            440                 445                 450

Val Ser Val Leu Thr Val Leu His Gln Asp Trp Leu Asn Gly Lys
            455                 460                 465

Glu Tyr Lys Cys Lys Val Ser Asn Lys Ala Leu Pro Ala Pro Ile
            470                 475                 480

Glu Lys Thr Ile Ser Lys Ala Lys Gly Gln Pro Arg Glu Pro Gln
            485                 490                 495

Val Tyr Thr Leu Pro Pro Ser Arg Glu Glu Met Thr Lys Asn Gln
            500                 505                 510

Val Ser Leu Thr Cys Leu Val Lys Gly Phe Tyr Pro Ser Asp Ile
            515                 520                 525

Ala Val Glu Trp Glu Ser Asn Gly Gln Pro Glu Asn Asn Tyr Lys
            530                 535                 540

Thr Thr Pro Pro Val Leu Asp Ser Asp Gly Ser Phe Phe Leu Tyr
            545                 550                 555

Ser Lys Leu Thr Val Asp Lys Ser Arg Trp Gln Gln Gly Asn Val
            560                 565                 570

Phe Ser Cys Ser Val Met His Glu Ala Leu His Asn His Tyr Thr
            575                 580                 585

Gln Lys Ser Leu Ser Leu Ser Pro Gly Lys
            590                 595

<210> SEQ ID NO 3
<211> LENGTH: 367
<212> TYPE: PRT
<213> ORGANISM: homo sapien

<400> SEQUENCE: 3

Met Arg Trp Phe Leu Pro Trp Thr Leu Ala Ala Val Thr Ala Ala
  1               5                  10                  15

Ala Ala Ser Thr Val Leu Ala Thr Ala Leu Ser Pro Ala Pro Thr
            20                  25                  30

Thr Met Asp Phe Thr Pro Ala Pro Leu Glu Asp Thr Ser Ser Arg
            35                  40                  45
```

Pro Gln Phe Cys Lys Trp Pro Cys Glu Cys Pro Pro Ser Pro Pro
             50                  55                  60

Arg Cys Pro Leu Gly Val Ser Leu Ile Thr Asp Gly Cys Glu Cys
         65                  70                  75

Cys Lys Met Cys Ala Gln Gln Leu Gly Asp Asn Cys Thr Glu Ala
             80                  85                  90

Ala Ile Cys Asp Pro His Arg Gly Leu Tyr Cys Asp Tyr Ser Gly
             95                 100                 105

Asp Arg Pro Arg Tyr Ala Ile Gly Val Cys Ala Gln Val Val Gly
            110                 115                 120

Val Gly Cys Val Leu Asp Gly Val Arg Tyr Asn Asn Gly Gln Ser
            125                 130                 135

Phe Gln Pro Asn Cys Lys Tyr Asn Cys Thr Cys Ile Asp Gly Ala
            140                 145                 150

Val Gly Cys Thr Pro Leu Cys Leu Arg Val Arg Pro Pro Arg Leu
            155                 160                 165

Trp Cys Pro His Pro Arg Arg Val Ser Ile Pro Gly His Cys Cys
            170                 175                 180

Glu Gln Trp Val Cys Glu Asp Asp Ala Lys Arg Pro Arg Lys Thr
            185                 190                 195

Ala Pro Arg Asp Thr Gly Ala Phe Asp Ala Val Gly Glu Val Glu
            200                 205                 210

Ala Trp His Arg Asn Cys Ile Ala Tyr Thr Ser Pro Trp Ser Pro
            215                 220                 225

Cys Ser Thr Ser Cys Gly Leu Gly Val Ser Thr Arg Ile Ser Asn
            230                 235                 240

Val Asn Ala Gln Cys Trp Pro Glu Gln Glu Ser Arg Leu Cys Asn
            245                 250                 255

Leu Arg Pro Cys Asp Val Asp Ile His Thr Leu Ile Lys Ala Gly
            260                 265                 270

Lys Lys Cys Leu Ala Val Tyr Gln Pro Glu Ala Ser Met Asn Phe
            275                 280                 285

Thr Leu Ala Gly Cys Ile Ser Thr Arg Ser Tyr Gln Pro Lys Tyr
            290                 295                 300

Cys Gly Val Cys Met Asp Asn Arg Cys Cys Ile Pro Tyr Lys Ser
            305                 310                 315

Lys Thr Ile Asp Val Ser Phe Gln Cys Pro Asp Gly Leu Gly Phe
            320                 325                 330

Ser Arg Gln Val Leu Trp Ile Asn Ala Cys Phe Cys Asn Leu Ser
            335                 340                 345

Cys Arg Asn Pro Asn Asp Ile Phe Ala Asp Leu Glu Ser Tyr Pro
            350                 355                 360

Asp Phe Ser Glu Ile Ala Asn
            365

<210> SEQ ID NO 4
<211> LENGTH: 367
<212> TYPE: PRT
<213> ORGANISM: mus musculus

<400> SEQUENCE: 4

Met Arg Trp Leu Leu Pro Trp Thr Leu Ala Ala Val Ala Val Leu
  1               5                  10                  15

Arg Val Gly Asn Ile Leu Ala Thr Ala Leu Ser Pro Thr Pro Thr
             20                  25                  30

```
Thr Met Thr Phe Thr Pro Ala Pro Leu Glu Glu Thr Thr Arg
            35                  40                  45

Pro Glu Phe Cys Lys Trp Pro Cys Glu Cys Pro Gln Ser Pro Pro
        50                  55                  60

Arg Cys Pro Leu Gly Val Ser Leu Ile Thr Asp Gly Cys Glu Cys
            65                  70                  75

Cys Lys Ile Cys Ala Gln Gln Leu Gly Asp Asn Cys Thr Glu Ala
            80                  85                  90

Ala Ile Cys Asp Pro His Arg Gly Leu Tyr Cys Asp Tyr Ser Gly
            95                 100                 105

Asp Arg Pro Arg Tyr Ala Ile Gly Val Cys Ala Gln Val Val Gly
           110                 115                 120

Val Gly Cys Val Leu Asp Gly Val Arg Tyr Thr Asn Gly Glu Ser
           125                 130                 135

Phe Gln Pro Asn Cys Arg Tyr Asn Cys Thr Cys Ile Asp Gly Thr
           140                 145                 150

Val Gly Cys Thr Pro Leu Cys Leu Ser Pro Arg Pro Pro Arg Leu
           155                 160                 165

Trp Cys Arg Gln Pro Arg His Val Arg Val Pro Gly Gln Cys Cys
           170                 175                 180

Glu Gln Trp Val Cys Asp Asp Asp Ala Arg Arg Pro Arg Gln Thr
           185                 190                 195

Ala Leu Leu Asp Thr Arg Ala Phe Ala Ala Ser Gly Ala Val Glu
           200                 205                 210

Gln Arg Tyr Glu Asn Cys Ile Ala Tyr Thr Ser Pro Trp Ser Pro
           215                 220                 225

Cys Ser Thr Thr Cys Gly Leu Gly Ile Ser Thr Arg Ile Ser Asn
           230                 235                 240

Val Asn Ala Arg Cys Trp Pro Glu Gln Glu Ser Arg Leu Cys Asn
           245                 250                 255

Leu Arg Pro Cys Asp Val Asp Ile Gln Leu His Ile Lys Ala Gly
           260                 265                 270

Lys Lys Cys Leu Ala Val Tyr Gln Pro Glu Glu Ala Thr Asn Phe
           275                 280                 285

Thr Leu Ala Gly Cys Val Ser Thr Arg Thr Tyr Arg Pro Lys Tyr
           290                 295                 300

Cys Gly Val Cys Thr Asp Asn Arg Cys Cys Ile Pro Tyr Lys Ser
           305                 310                 315

Lys Thr Ile Ser Val Asp Phe Gln Cys Pro Glu Gly Pro Gly Phe
           320                 325                 330

Ser Arg Gln Val Leu Trp Ile Asn Ala Cys Phe Cys Asn Leu Ser
           335                 340                 345

Cys Arg Asn Pro Asn Asp Ile Phe Ala Asp Leu Glu Ser Tyr Pro
           350                 355                 360

Asp Phe Glu Glu Ile Ala Asn
           365

<210> SEQ ID NO 5
<211> LENGTH: 228
<212> TYPE: PRT
<213> ORGANISM: homo sapien
```

<400> SEQUENCE: 5

```
Pro Asp Lys Thr His Thr Cys Pro Pro Cys Pro Ala Pro Glu Leu
 1               5                  10                  15

Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val
            35                  40                  45

Asp Val Ser His Glu Asp Pro Glu Val Lys Phe Asn Trp Tyr Val
            50                  55                  60

Asp Gly Val Glu Val His Asn Ala Lys Thr Lys Pro Arg Glu Glu
            65                  70                  75

Gln Tyr Asn Ser Thr Tyr Arg Val Val Ser Val Leu Thr Val Leu
            80                  85                  90

His Gln Asp Trp Leu Asn Gly Lys Glu Tyr Lys Cys Lys Val Ser
            95                  100                 105

Asn Lys Ala Leu Pro Ala Pro Ile Glu Lys Thr Ile Ser Lys Ala
            110                 115                 120

Lys Gly Gln Pro Arg Glu Pro Gln Val Tyr Thr Leu Pro Pro Ser
            125                 130                 135

Arg Glu Glu Met Thr Lys Asn Gln Val Ser Leu Thr Cys Leu Val
            140                 145                 150

Lys Gly Phe Tyr Pro Ser Asp Ile Ala Val Glu Trp Glu Ser Asn
            155                 160                 165

Gly Gln Pro Glu Asn Asn Tyr Lys Thr Thr Pro Pro Val Leu Asp
            170                 175                 180

Ser Asp Gly Ser Phe Phe Leu Tyr Ser Lys Leu Thr Val Asp Lys
            185                 190                 195

Ser Arg Trp Gln Gln Gly Asn Val Phe Ser Cys Ser Val Met His
            200                 205                 210

Glu Ala Leu His Asn His Tyr Thr Gln Lys Ser Leu Ser Leu Ser
            215                 220                 225

Pro Gly Lys
```

<210> SEQ ID NO 6
<211> LENGTH: 600
<212> TYPE: PRT
<213> ORGANISM: homo sapien

<400> SEQUENCE: 6

```
Met Asn Lys Arg Arg Leu Leu Tyr Pro Ser Gly Trp Leu His Gly
 1               5                  10                  15

Pro Ser Asp Met Gln Gly Leu Leu Phe Ser Thr Leu Leu Leu Ala
            20                  25                  30

Gly Leu Ala Gln Phe Cys Cys Arg Val Gln Gly Thr Gly Pro Leu
            35                  40                  45

Asp Thr Thr Pro Glu Gly Arg Pro Gly Glu Val Ser Asp Ala Pro
            50                  55                  60

Gln Arg Lys Gln Phe Cys His Trp Pro Cys Lys Cys Pro Gln Gln
            65                  70                  75

Lys Pro Arg Cys Pro Pro Gly Val Ser Leu Val Arg Asp Gly Cys
            80                  85                  90

Gly Cys Cys Lys Ile Cys Ala Lys Gln Pro Gly Glu Ile Cys Asn
            95                  100                 105
```

-continued

```
Glu Ala Asp Leu Cys Asp Pro His Lys Gly Leu Tyr Cys Asp Tyr
                110                 115                 120

Ser Val Asp Arg Pro Arg Tyr Glu Thr Gly Val Cys Ala Tyr Leu
            125                 130                 135

Val Ala Val Gly Cys Glu Phe Asn Gln Val His Tyr His Asn Gly
            140                 145                 150

Gln Val Phe Gln Pro Asn Pro Leu Phe Ser Cys Leu Cys Val Ser
            155                 160                 165

Gly Ala Ile Gly Cys Thr Pro Leu Phe Ile Pro Lys Leu Ala Gly
            170                 175                 180

Ser His Cys Ser Gly Ala Lys Gly Gly Lys Ser Asp Gln Ser
            185                 190                 195

Asn Cys Ser Leu Glu Pro Leu Leu Gln Gln Leu Ser Thr Ser Tyr
            200                 205                 210

Lys Thr Met Pro Ala Tyr Arg Asp Leu Pro Leu Ile Trp Lys Lys
            215                 220                 225

Lys Cys Leu Val Gln Ala Thr Lys Trp Thr Pro Cys Ser Arg Thr
            230                 235                 240

Cys Gly Met Gly Ile Ser Asn Arg Val Thr Asn Glu Asn Ser Asn
            245                 250                 255

Cys Glu Met Arg Lys Glu Lys Arg Leu Cys Tyr Ile Gln Pro Cys
            260                 265                 270

Asp Ser Asn Ile Leu Lys Thr Ile Lys Ile Pro Lys Gly Lys Thr
            275                 280                 285

Cys Gln Pro Thr Phe Gln Leu Ser Lys Ala Glu Lys Phe Val Phe
            290                 295                 300

Ser Gly Cys Ser Ser Thr Gln Ser Tyr Lys Pro Thr Phe Cys Gly
            305                 310                 315

Ile Cys Leu Asp Lys Arg Cys Cys Ile Pro Asn Lys Ser Lys Met
            320                 325                 330

Ile Thr Ile Gln Phe Asp Cys Pro Asn Glu Gly Ser Phe Lys Trp
            335                 340                 345

Lys Met Leu Trp Ile Thr Ser Cys Val Cys Gln Arg Asn Cys Arg
            350                 355                 360

Glu Pro Gly Asp Ile Phe Ser Glu Leu Lys Ile Leu Pro Asp Lys
            365                 370                 375

Thr His Thr Cys Pro Pro Cys Pro Ala Pro Glu Leu Leu Gly Gly
            380                 385                 390

Pro Ser Val Phe Leu Phe Pro Pro Lys Pro Lys Asp Thr Leu Met
            395                 400                 405

Ile Ser Arg Thr Pro Glu Val Thr Cys Val Val Val Asp Val Ser
            410                 415                 420

His Glu Asp Pro Glu Val Lys Phe Asn Trp Tyr Val Asp Gly Val
            425                 430                 435

Glu Val His Asn Ala Lys Thr Lys Pro Arg Glu Glu Gln Tyr Asn
            440                 445                 450

Ser Thr Tyr Arg Val Val Ser Val Leu Thr Val Leu His Gln Asp
            455                 460                 465

Trp Leu Asn Gly Lys Glu Tyr Lys Cys Lys Val Ser Asn Lys Ala
            470                 475                 480

Leu Pro Ala Pro Ile Glu Lys Thr Ile Ser Lys Ala Lys Gly Gln
            485                 490                 495
```

-continued

```
Pro Arg Glu Pro Gln Val Tyr Thr Leu Pro Pro Ser Arg Glu Glu
                500                 505                 510

Met Thr Lys Asn Gln Val Ser Leu Thr Cys Leu Val Lys Gly Phe
                515                 520                 525

Tyr Pro Ser Asp Ile Ala Val Glu Trp Glu Ser Asn Gly Gln Pro
                530                 535                 540

Glu Asn Asn Tyr Lys Thr Thr Pro Pro Val Leu Asp Ser Asp Gly
                545                 550                 555

Ser Phe Phe Leu Tyr Ser Lys Leu Thr Val Asp Lys Ser Arg Trp
                560                 565                 570

Gln Gln Gly Asn Val Phe Ser Cys Ser Val Met His Glu Ala Leu
                575                 580                 585

His Asn His Tyr Thr Gln Lys Ser Leu Ser Leu Ser Pro Gly Lys
                590                 595                 600

<210> SEQ ID NO 7
<211> LENGTH: 582
<212> TYPE: PRT
<213> ORGANISM: homo sapien

<400> SEQUENCE: 7

Met Gln Gly Leu Leu Phe Ser Thr Leu Leu Leu Ala Gly Leu Ala
 1               5                  10                  15

Gln Phe Cys Cys Arg Val Gln Gly Thr Gly Pro Leu Asp Thr Thr
                20                  25                  30

Pro Glu Gly Arg Pro Gly Glu Val Ser Asp Ala Pro Gln Arg Lys
                35                  40                  45

Gln Phe Cys His Trp Pro Cys Lys Cys Pro Gln Gln Lys Pro Arg
                50                  55                  60

Cys Pro Pro Gly Val Ser Leu Val Arg Asp Gly Cys Gly Cys Cys
                65                  70                  75

Lys Ile Cys Ala Lys Gln Pro Gly Glu Ile Cys Asn Glu Ala Asp
                80                  85                  90

Leu Cys Asp Pro His Lys Gly Leu Tyr Cys Asp Tyr Ser Val Asp
                95                  100                 105

Arg Pro Arg Tyr Glu Thr Gly Val Cys Ala Tyr Leu Val Ala Val
                110                 115                 120

Gly Cys Glu Phe Asn Gln Val His Tyr His Asn Gly Gln Val Phe
                125                 130                 135

Gln Pro Asn Pro Leu Phe Ser Cys Leu Cys Val Ser Gly Ala Ile
                140                 145                 150

Gly Cys Thr Pro Leu Phe Ile Pro Lys Leu Ala Gly Ser His Cys
                155                 160                 165

Ser Gly Ala Lys Gly Gly Lys Lys Ser Asp Gln Ser Asn Cys Ser
                170                 175                 180

Leu Glu Pro Leu Leu Gln Leu Ser Thr Ser Tyr Lys Thr Met
                185                 190                 195

Pro Ala Tyr Arg Asn Leu Pro Leu Ile Trp Lys Lys Lys Cys Leu
                200                 205                 210

Val Gln Ala Thr Lys Trp Thr Pro Cys Ser Arg Thr Cys Gly Met
                215                 220                 225

Gly Ile Ser Asn Arg Val Thr Asn Glu Asn Ser Asn Cys Glu Met
                230                 235                 240

Arg Lys Glu Lys Arg Leu Cys Tyr Ile Gln Pro Cys Asp Ser Asn
                245                 250                 255
```

```
Ile Leu Lys Thr Ile Lys Ile Pro Lys Gly Lys Thr Cys Gln Pro
            260                 265                 270

Thr Phe Gln Leu Ser Lys Ala Glu Lys Phe Val Phe Ser Gly Cys
            275                 280                 285

Ser Ser Thr Gln Ser Tyr Lys Pro Thr Phe Cys Gly Ile Cys Leu
            290                 295                 300

Asp Lys Arg Cys Cys Ile Pro Asn Lys Ser Lys Met Ile Thr Ile
            305                 310                 315

Gln Phe Asp Cys Pro Asn Glu Gly Ser Phe Lys Trp Lys Met Leu
            320                 325                 330

Trp Ile Thr Ser Cys Val Cys Gln Arg Asn Cys Arg Glu Pro Gly
            335                 340                 345

Asp Ile Phe Ser Glu Leu Lys Ile Leu Pro Asp Lys Thr His Thr
            350                 355                 360

Cys Pro Pro Cys Pro Ala Pro Glu Leu Leu Gly Gly Pro Ser Val
            365                 370                 375

Phe Leu Phe Pro Pro Lys Pro Lys Asp Thr Leu Met Ile Ser Arg
            380                 385                 390

Thr Pro Glu Val Thr Cys Val Val Val Asp Val Ser His Glu Asp
            395                 400                 405

Pro Glu Val Lys Phe Asn Trp Tyr Val Asp Gly Val Glu Val His
            410                 415                 420

Asn Ala Lys Thr Lys Pro Arg Glu Glu Gln Tyr Asn Ser Thr Tyr
            425                 430                 435

Arg Val Val Ser Val Leu Thr Val Leu His Gln Asp Trp Leu Asn
            440                 445                 450

Gly Lys Glu Tyr Lys Cys Lys Val Ser Asn Lys Ala Leu Pro Ala
            455                 460                 465

Pro Ile Glu Lys Thr Ile Ser Lys Ala Lys Gly Gln Pro Arg Glu
            470                 475                 480

Pro Gln Val Tyr Thr Leu Pro Pro Ser Arg Glu Glu Met Thr Lys
            485                 490                 495

Asn Gln Val Ser Leu Thr Cys Leu Val Lys Gly Phe Tyr Pro Ser
            500                 505                 510

Asp Ile Ala Val Glu Trp Glu Ser Asn Gly Gln Pro Glu Asn Asn
            515                 520                 525

Tyr Lys Thr Thr Pro Pro Val Leu Asp Ser Asp Gly Ser Phe Phe
            530                 535                 540

Leu Tyr Ser Lys Leu Thr Val Asp Lys Ser Arg Trp Gln Gln Gly
            545                 550                 555

Asn Val Phe Ser Cys Ser Val Met His Glu Ala Leu His Asn His
            560                 565                 570

Tyr Thr Gln Lys Ser Leu Ser Leu Ser Pro Gly Lys
            575                 580

<210> SEQ ID NO 8
<211> LENGTH: 354
<212> TYPE: PRT
<213> ORGANISM: homo sapien

<400> SEQUENCE: 8

Met Gln Gly Leu Leu Phe Ser Thr Leu Leu Leu Ala Gly Leu Ala
  1               5                  10                  15

Gln Phe Cys Cys Arg Val Gln Gly Thr Gly Pro Leu Asp Thr Thr
            20                  25                  30
```

```
Pro Glu Gly Arg Pro Gly Glu Val Ser Asp Ala Pro Gln Arg Lys
            35                  40                  45

Gln Phe Cys His Trp Pro Cys Lys Cys Pro Gln Gln Lys Pro Arg
            50                  55                  60

Cys Pro Pro Gly Val Ser Leu Val Arg Asp Gly Cys Gly Cys Cys
            65                  70                  75

Lys Ile Cys Ala Lys Gln Pro Gly Glu Ile Cys Asn Glu Ala Asp
            80                  85                  90

Leu Cys Asp Pro His Lys Gly Leu Tyr Cys Asp Tyr Ser Val Asp
            95                 100                 105

Arg Pro Arg Tyr Glu Thr Gly Val Cys Ala Tyr Leu Val Ala Val
           110                 115                 120

Gly Cys Glu Phe Asn Gln Val His Tyr His Asn Gly Gln Val Phe
           125                 130                 135

Gln Pro Asn Pro Leu Phe Ser Cys Leu Cys Val Ser Gly Ala Ile
           140                 145                 150

Gly Cys Thr Pro Leu Phe Ile Pro Lys Leu Ala Gly Ser His Cys
           155                 160                 165

Ser Gly Ala Lys Gly Lys Lys Ser Asp Gln Ser Asn Cys Ser
           170                 175                 180

Leu Glu Pro Leu Leu Gln Gln Leu Ser Thr Ser Tyr Lys Thr Met
           185                 190                 195

Pro Ala Tyr Arg Asn Leu Pro Leu Ile Trp Lys Lys Lys Cys Leu
           200                 205                 210

Val Gln Ala Thr Lys Trp Thr Pro Cys Ser Arg Thr Cys Gly Met
           215                 220                 225

Gly Ile Ser Asn Arg Val Thr Asn Glu Asn Ser Asn Cys Glu Met
           230                 235                 240

Arg Lys Glu Lys Arg Leu Cys Tyr Ile Gln Pro Cys Asp Ser Asn
           245                 250                 255

Ile Leu Lys Thr Ile Lys Ile Pro Lys Gly Lys Thr Cys Gln Pro
           260                 265                 270

Thr Phe Gln Leu Ser Lys Ala Glu Lys Phe Val Phe Ser Gly Cys
           275                 280                 285

Ser Ser Thr Gln Ser Tyr Lys Pro Thr Phe Cys Gly Ile Cys Leu
           290                 295                 300

Asp Lys Arg Cys Cys Ile Pro Asn Lys Ser Lys Met Ile Thr Ile
           305                 310                 315

Gln Phe Asp Cys Pro Asn Glu Gly Ser Phe Lys Trp Lys Met Leu
           320                 325                 330

Trp Ile Thr Ser Cys Val Cys Gln Arg Asn Cys Arg Glu Pro Gly
           335                 340                 345

Asp Ile Phe Ser Glu Leu Lys Ile Leu
           350

<210> SEQ ID NO 9
<211> LENGTH: 372
<212> TYPE: PRT
<213> ORGANISM: homo sapien

<400> SEQUENCE: 9

Met Asn Lys Arg Arg Leu Leu Tyr Pro Ser Gly Trp Leu His Gly
 1               5                  10                  15

Pro Ser Asp Met Gln Gly Leu Leu Phe Ser Thr Leu Leu Leu Ala
            20                  25                  30
```

```
Gly Leu Ala Gln Phe Cys Cys Arg Val Gln Gly Thr Gly Pro Leu
             35                  40                  45

Asp Thr Thr Pro Glu Gly Arg Pro Gly Glu Val Ser Asp Ala Pro
             50                  55                  60

Gln Arg Lys Gln Phe Cys His Trp Pro Cys Lys Cys Pro Gln Gln
             65                  70                  75

Lys Pro Arg Cys Pro Pro Gly Val Ser Leu Val Arg Asp Gly Cys
             80                  85                  90

Gly Cys Cys Lys Ile Cys Ala Lys Gln Pro Gly Glu Ile Cys Asn
             95                 100                 105

Glu Ala Asp Leu Cys Asp Pro His Lys Gly Leu Tyr Cys Asp Tyr
            110                 115                 120

Ser Val Asp Arg Pro Arg Tyr Glu Thr Gly Val Cys Ala Tyr Leu
            125                 130                 135

Val Ala Val Gly Cys Glu Phe Asn Gln Val His Tyr His Asn Gly
            140                 145                 150

Gln Val Phe Gln Pro Asn Pro Leu Phe Ser Cys Leu Cys Val Ser
            155                 160                 165

Gly Ala Ile Gly Cys Thr Pro Leu Phe Ile Pro Lys Leu Ala Gly
            170                 175                 180

Ser His Cys Ser Gly Ala Lys Gly Gly Lys Ser Asp Gln Ser
            185                 190                 195

Asn Cys Ser Leu Glu Pro Leu Leu Gln Gln Leu Ser Thr Ser Tyr
            200                 205                 210

Lys Thr Met Pro Ala Tyr Arg Asp Leu Pro Leu Ile Trp Lys Lys
            215                 220                 225

Lys Cys Leu Val Gln Ala Thr Lys Trp Thr Pro Cys Ser Arg Thr
            230                 235                 240

Cys Gly Met Gly Ile Ser Asn Arg Val Thr Asn Glu Asn Ser Asn
            245                 250                 255

Cys Glu Met Arg Lys Glu Lys Arg Leu Cys Tyr Ile Gln Pro Cys
            260                 265                 270

Asp Ser Asn Ile Leu Lys Thr Ile Lys Ile Pro Lys Gly Lys Thr
            275                 280                 285

Cys Gln Pro Thr Phe Gln Leu Ser Lys Ala Glu Lys Phe Val Phe
            290                 295                 300

Ser Gly Cys Ser Ser Thr Gln Ser Tyr Lys Pro Thr Phe Cys Gly
            305                 310                 315

Ile Cys Leu Asp Lys Arg Cys Cys Ile Pro Asn Lys Ser Lys Met
            320                 325                 330

Ile Thr Ile Gln Phe Asp Cys Pro Asn Glu Gly Ser Phe Lys Trp
            335                 340                 345

Lys Met Leu Trp Ile Thr Ser Cys Val Cys Gln Arg Asn Cys Arg
            350                 355                 360

Glu Pro Gly Asp Ile Phe Ser Glu Leu Lys Ile Leu
            365                 370

<210> SEQ ID NO 10
<211> LENGTH: 250
<212> TYPE: PRT
<213> ORGANISM: homo sapien
```

-continued

```
<400> SEQUENCE: 10

Met Arg Gly Thr Pro Lys Thr His Leu Leu Ala Phe Ser Leu Leu
 1               5                  10                  15

Cys Leu Leu Ser Lys Val Arg Thr Gln Leu Cys Pro Thr Pro Cys
                20                  25                  30

Thr Cys Pro Trp Pro Pro Arg Cys Pro Leu Gly Val Pro Leu
                35                  40                  45

Val Leu Asp Gly Cys Gly Cys Cys Arg Val Cys Ala Arg Arg Leu
                50                  55                  60

Gly Glu Pro Cys Asp Gln Leu His Val Cys Asp Ala Ser Gln Gly
                65                  70                  75

Leu Val Cys Gln Pro Gly Ala Gly Pro Gly Gly Arg Gly Ala Leu
                80                  85                  90

Cys Leu Leu Ala Glu Asp Asp Ser Ser Cys Glu Val Asn Gly Arg
                95                  100                 105

Leu Tyr Arg Glu Gly Glu Thr Phe Gln Pro His Cys Ser Ile Arg
                110                 115                 120

Cys Arg Cys Glu Asp Gly Gly Phe Thr Cys Val Pro Leu Cys Ser
                125                 130                 135

Glu Asp Val Arg Leu Pro Ser Trp Asp Cys Pro His Pro Arg Arg
                140                 145                 150

Val Glu Val Leu Gly Lys Cys Cys Pro Glu Trp Val Cys Gly Gln
                155                 160                 165

Gly Gly Gly Leu Gly Thr Gln Pro Leu Pro Ala Gln Gly Pro Gln
                170                 175                 180

Phe Ser Gly Leu Val Ser Ser Leu Pro Pro Gly Val Pro Cys Pro
                185                 190                 195

Glu Trp Ser Thr Ala Trp Gly Pro Cys Ser Thr Thr Cys Gly Leu
                200                 205                 210

Gly Met Ala Thr Arg Val Ser Asn Gln Asn Arg Phe Cys Arg Leu
                215                 220                 225

Glu Thr Gln Arg Arg Leu Cys Leu Ser Arg Pro Cys Pro Pro Ser
                230                 235                 240

Arg Gly Arg Ser Pro Gln Asn Ser Ala Phe
                245                 250
```

}

METHODS OF TREATMENT USING WISP POLYPEPTIDES

RELATED APPLICATIONS

This application is a non-provisional application claiming priority under Section 119(e) to provisional application No. 60/241,222, filed Oct. 16, 2000, the contents of which are incorporated herein by reference.

FIELD OF THE INVENTION

The present invention relates generally to methods of using WISP polypeptides in the treatment of degenerative cartilagenous disorders and various immune related conditions.

BACKGROUND OF THE INVENTION

Connective tissue growth factor (CTGF) is a growth factor induced in fibroblasts by many factors, including TGF-β, and is essential for the ability of TGF-β to induce anchorage-independent growth (AIG), a property of transformed cells. CTGF was discovered in an attempt to identify the type of platelet-derived growth factor (PDGF) dimers present in the growth media of cultured endothelial cells, and is related immunologically and biologically to PDGF. See U.S. Pat. No. 5,408,040. CTGF also is mitogenic and chemotactic for cells, and hence growth factors in this family are believed to play a role in the normal development, growth, and repair of human tissue.

Seven proteins related to CTGF, including the chicken ortholog for Cyr61, CEF10, human, mouse, and *Xenopus laevis* CTGF, and human, chicken, and *Xenopus laevis* Nov have been isolated, cloned, sequenced, and characterized as belonging to the CCN gene family. Oemar and Luescher, *Arterioscler. Thromb. Vasc. Biol.,* 17: 1483-1489 (1997). The gene encoding Cyr61 has been found to promote angiogenesis, tumor growth, and vascularization. Babic et al., *Proc. Natl. Acad. Sci. USA,* 95: 6355-6360 (1998). The nov gene is expressed in the kidney essentially at the embryonic stage, and alterations of nov expression, relative to the normal kidney, have been detected in both avian nephroblastomas and human Wilms' tumors. Martinerie et al., *Oncogene,* 9: 2729-2732 (1994). Wt1 downregulates human nov expression, which downregulation might represent a key element in normal and tumoral nephrogenesis. Martinerie et al., *Oncogene,* 12: 1479-1492 (1996). It has recently been proposed that the CTGF, nov, and cyr61 genes, which encode secreted proteins that contain conserved sequences and IGFBP motifs in their N-termini and bind IGFs with low affinity, represent more members of the IGFBP superfamily, along with the low-affinity mac25/IGFBP-7 (Yamanaka et al., *J. Biol. Chem.,* 272: 30729-30734 (1997)) and the high-affinity IGFBPs 1-6. CTGF under this proposal would be designated IGFBP-8. Kim et al., *Proc. Natl. Acad. Sci. USA,* 94: 12981-12986 (1997).

The different members of the CCN family interact with various soluble or matrix associated macromolecules in particular sulfated glycoconjugates (Holt et al., *J. Biol. Chem.,* 265:2852-2855 (1990)). This interaction was used to purify Cyr61 and CTGF by affinity chromatography on heparin-agarose (Frazier et al., *J. Invest. Dermatol.,* 107:404-411 (1996); Kireeva et al., *Mol. Cell. Biol.,* 16:1326-1334 (1996)). Cyr61 is secreted and associated with both the extracellular matrix and the cell surface due to its affinity for heparan sulfate (Yang et al., *Cell. Growth Diff.,* 2:351-357 (1991)).

Recently, a protein was found in the mouse designated ELM1 that is expressed in low metastatic cells. Hashimoto et al., *J. Exp. Med.,* 187: 289-296 (1998). The elm1 gene, a mouse homologue of WISP-1 disclosed below, is another member of the CTGF, Cyr61/Cef10, and neuroblastoma overexpressed-gene family and suppresses in vivo tumor growth and metastasis of K-1735 murine melanoma cells. Another recent article on rCop-1, the rat orthologue of WISP-2 described below describes the loss of expression of this gene after cell transformation. Zhang et al., *Mol. Cell. Biol.,* 18:6131-6141 (1998).

CCN family members (with the exception of nov) are immediate early growth-responsive genes that are thought to regulate cell proliferation, differentiation, embryogenesis, and wound healing. Sequence homology among members of the CCN gene family is somewhat high; however, functions of these proteins in vitro range from growth stimulatory (i.e., human CTGF) to growth inhibitory (i.e., chicken Nov and also possibly hCTGF). Further, some molecules homologous to CTGF are indicated to be useful in the prevention of desmoplasia, the formation of highly cellular, excessive connective tissue stroma associated with some cancers, and fibrotic lesions associated with various skin disorders such as scleroderma, keloid, eosinophilic fasciitis, nodular fasciitis, and Dupuytren's contracture. Moreover, CTGF expression has recently been demonstrated in the fibrous stroma of mammary tumors, suggesting cancer stroma formation involves the induction of similar fibroproliferative growth factors as wound repair. Human CTGF is also expressed at very high levels in advanced atherosclerotic lesions, but not in normal arteries, suggesting it may play a role in atherosclerosis. Oemar and Luescher, supra.

Wnts are encoded by a large gene family whose members have been found in round worms, insects, cartilaginous fish, and vertebrates. Holland et al., *Dev. Suppl.,* 125-133 (1994). Wnts are thought to function in a variety of developmental and physiological processes since many diverse species have multiple conserved Wnt genes. McMahon, *Trends Genet.,* 8: 236-242 (1992); Nusse and Varmus, *Cell,* 69: 1073-1087 (1992). Wnt genes encode secreted glycoproteins that are thought to function as paracrine or autocrine signals active in several primitive cell types. McMahon, supra (1992); Nusse and Varmus, supra (1992). The Wnt growth factor family includes more than ten genes identified in the mouse (Wnt-1, -2, -3A, -3B, -4, -5A, -5B, -6, -7A, -7B, -8A, -8B, -10B, -11, -12, and -13) (see, e.g., Gavin et al., *Genes Dev.,* 4: 2319-2332 (1990); Lee et al., *Proc. Natl. Acad. Sci. USA,* 92: 2268-2272 (1995); Christiansen et al., *Mech. Dev.,* 51: 341-350 (1995)) and at least nine genes identified in the human (Wnt-1, -2, -3, -5A, -7A, -7B, -8B, -10B, and -11) by cDNA cloning. See, e.g., Vant Veer et al., *Mol. Cell. Biol.,* 4: 2532-2534 (1984).

The Wnt-1 proto-oncogene (int-1) was originally identified from mammary tumors induced by mouse mammary tumor virus (MMTV) due to an insertion of viral DNA sequence. Nusse and Varmus, *Cell,* 31: 99-109 (1982). In adult mice, the expression level of Wnt-1 mRNA is detected only in the testis during later stages of sperm development. Wnt-1 protein is about 42 KDa and contains an amino-terminal hydrophobic region, which may function as a signal sequence for secretion (Nusse and Varmus, supra, 1992). The expression of Wnt-2/irp is detected in mouse fetal and adult tissues and its distribution does not overlap with the expression pattern for Wnt-1. Wnt-3 is associated with mouse mammary tumorigenesis. The expression of Wnt-3 in mouse embryos is detected in the neural tubes and in the limb buds. Wnt-5a transcripts are detected in the developing fore- and hind limbs at 9.5 through 14.5 days and highest levels are concentrated in apical ectoderm at the distal tip of limbs. Nusse and Varmus, supra (1992). Recently, a Wnt growth factor, termed Wnt-x, was described (WO95/17416) along with the detection of Wnt-x expression in bone tissues and in bone-derived cells. Also described was the role of Wnt-x in the maintenance of mature osteoblasts and the use of the Wnt-x growth factor as a therapeutic agent or in the development of other therapeutic agents to treat bone-related diseases.

Wnts may play a role in local cell signaling. Biochemical studies have shown that much of the secreted Wnt protein can be found associated with the cell surface or extracellular matrix rather than freely diffusible in the medium. Papkoff and Schryver, *Mol. Cell. Biol.*, 10: 2723-2730 (1990); Bradley and Brown, *EMBO J.*, 9: 1569-1575 (1990).

Studies of mutations in Wnt genes have indicated a role for Wnts in growth control and tissue patterning. In *Drosophila*, wingless (wg) encodes a Wnt-related gene (Rijsewik et al., *Cell*, 50: 649-657 (1987)) and wg mutations alter the pattern of embryonic ectoderm, neurogenesis, and imaginal disc outgrowth. Morata and Lawerence, *Dev. Biol.*, 56: 227-240 (1977); Baker, *Dev. Biol.*, 125: 96-108 (1988); Klingensmith and Nusse, *Dev. Biol.*, 166: 396-414 (1994). In *Caenorhabditis elegans*, lin-44 encodes a Wnt homolog which is required for asymmetric cell divisions. Herman and Horvitz, *Development*, 120: 1035-1047 (1994). Knock-out mutations in mice have shown Wnts to be essential for brain development (McMahon and Bradley, *Cell*, 62: 1073-1085 (1990); Thomas and Cappechi, *Nature*, 346: 847-850 (1990)), and the outgrowth of embryonic primordia for kidney (Stark et al., *Nature*, 372: 679-683 (1994)), tail bud (Takada et al., *Genes Dev.*, 8: 174-189 (1994)), and limb bud. Parr and McMahon, *Nature*, 374: 350-353 (1995). Overexpression of Wnts in the mammary gland can result in mammary hyperplasia (McMahon, supra (1992); Nusse and Varmus, supra (1992)), and precocious alveolar development. Bradbury et al., *Dev. Biol.*, 170: 553-563 (1995).

Wnt-5a and Wnt-5b are expressed in the posterior and lateral mesoderm and the extraembryonic mesoderm of the day 7-8 murine embryo. Gavin et al., supra (1990). These embryonic domains contribute to the AGM region and yolk sac tissues from which multipotent hematopoietic precursors and HSCs are derived. Dzierzak and Medvinsky, *Trends Genet.*, 11: 359-366 (1995); Zon et al., in *Gluckman and Coulombel*, ed., Colloque, *INSERM*, 235: 17-22 (1995), presented at the Joint International Workshop on Foetal and Neonatal Hematopoiesis and Mechanism of Bone Marrow Failure, Paris France, Apr. 3-6, 1995; Kanatsu and Nishikawa, *Development*, 122: 823-830 (1996). Wnt-5a, Wnt-10b, and other Wnts have been detected in limb buds, indicating possible roles in the development and patterning of the early bone microenvironment as shown for Wnt-7b. Gavin et al., supra (1990); Christiansen et al., *Mech. Devel.*, 51: 341-350 (1995); Parr and McMahon, supra (1995).

The Wnt/Wg signal transduction pathway plays an important role in the biological development of the organism and has been implicated in several human cancers. This pathway also includes the tumor suppressor gene, APC. Mutations in the APC gene are associated with the development of sporadic and inherited forms of human colorectal cancer. The Wnt/Wg signal leads to the accumulation of beta-catenin/Armadillo in the cell, resulting in the formation of a bipartite transcription complex consisting of beta-catenin and a member of the lymphoid enhancer binding factor/T cell factor (LEF/TCF)HMG box transcription factor family. This complex translocates to the nucleus where it can activate expression of genes downstream of the Wnt/Wg signal, such as the engrailed and Ultrabithorax genes in *Drosophila*.

For a review on Wnt, see Cadigan and Nusse, *Genes & Dev.*, 11: 3286-3305 (1997).

Pennica et al., *Proc. Natl. Acad. Sci.*, 95:14717-14722 (1998) describe the cloning and characterization of two genes, WISP-1 and WISP-2, that are up-regulated in the mouse mammary epithelial cell line C57MG transformed by Wnt-1, and a third related gene, WISP-3. Pennica et al. report that these WISP genes may be downstream of Wnt-1 signaling and that aberrant levels of WISP expression in colon cancer may play a role in colon tumorigenesis. WISP-1 has recently been identified as a β-catenin-regulated gene and the characterization of its oncogenic activity demonstrated that WISP-1 might contribute to β-catenin-mediated tumorigenesis (Xu et al., *Gene & Develop.*, 14:585-595 (2000)). WISP-1 overexpression in normal rat kidney cells (NRK-49F) induced morphological transformation, accelerated cell growth and enhanced saturation density. In addition, these cells readily form tumors when injected into nude mice suggesting that WISP-1 may play some role in tumorigenesis (Xu et al., supra 2000).

Hurvitz et al., *Nature Genetics*, 23:94-97 (1999) describe a study involving WISP3 in which nine different mutations of WISP3 in unrelated individuals were found to be associated with the autosomal recessive skeletal disorder, progressive pseudorheumatoid dysplasia (PPD). WISP3 expression by RT-PCR was observed by Hurvitz et al. in human synoviocytes, articular cartilage chondrocytes, and bone-marrow-derived mesenchymal progenitor cells.

PCT application WO98/21236 published May 22, 1998 discloses a human connective tissue growth factor gene-3 (CTGF-3) encoding a 26 kD member of the growth factor superfamily. WO98/21236 discloses that the CTGF-3 amino acid sequence was deduced from a human osteoblast cDNA clone, and that CTGF-3 was expressed in multiple tissues like ovary, testis, heart, lung, skeletal muscle, adrenal medulla, adrenal cortex, thymus, prostate, small intestine and colon.

Several investigators have documented changes in the proteoglycan composition in neoplasms. Especially, a marked production of chondroitin sulfate proteoglycan is a well recognized phenomenon in a variety of malignant tumors. In addition, the expression of decorin, a dermatan sulfate containing proteoglycan, has been shown to be well correlated with malignancy in human carcinoma (Adany et al., *J. Biol. Chem.*, 265:11389-11396 (1990); Hunzlemann et al., *J. Invest. Dermatol.*, 104:509-513 (1995)). Recently, it was demonstrated that decorin suppresses the growth of several carcinomas (Santra 1997). Although the function of decorin in tumorigenic development is not fully understood, it was proposed that the decorin expression in the peritumorous stroma may reflect a regional response of the host connective tissue cells to the invading neoplastic cells (Stander et al., *Gene Therapy*, 5:1187-1194 (1999)).

For a recent review of various members of the connective tissue growth factor/cysteine-rich 61/nephroblastoma overexpressed (CNN) family, and their respective properties and activities, see Brigstock, *Endocrine Reviews*, 20:189-206 (1999).

Degenerative cartilagenous disorders broadly describe a collection of diseases characterized by degeneration or metabolic abnormalities of the connective tissues which can be manifested by pain, stiffness and limitation of motion of the affected body parts. The origin of these disorders can be, for example, pathological or as a result of trauma or injury.

Osteoarthritis (OA), also known as osteoarthrosis or degenerative joint disease, is typically the result of a series of localized degenerative processes that affect the articular structure and result in pain and diminished function. OA is often accompanied by a local inflammatory component that may accelerate joint destruction. OA is characterized by disruption of the smooth articulating surface of cartilage, with early loss of proteoglycans (PG) and collagens, followed by formation of clefts and fibrillation, and ultimately by full-thickness loss of cartilage. OA symptoms include local pain at the affected joints, especially after use. With disease progression, symptoms may progress to a continuous aching sensation, local discomfort and cosmetic alterations such as deformity of the affected joint.

In contrast to the localized nature of OA, rheumatoid arthritis (RA) is a systemic, inflammatory disease which likely begins in the synovium, the tissues surrounding the joint space. RA is a chronic autoimmune disorder characterized by symmetrical synovitis of the joint and typically affects small and large diarthrodial joints, leading to their progressive destruction. As the disease progresses, the symptoms of RA may also include fever, weight loss, thinning of the skin, multiorgan involvement, scleritis, corneal ulcers, formation of subcutaneous or subperiosteal nodules and premature death. While the cause(s) or origins of RA and OA are distinctly different, the cytokines and enzymes involved in cartilage destruction appear to be similar.

Peptide growth factors are believed to be important regulators of cartilage growth and cartilage cell (chondrocyte) behavior (i.e., differentiation, migration, division, and matrix synthesis or breakdown) F. S. Chen et al., *Am J. Orthop.* 26: 396-406 (1997). Growth factors that have been previously proposed to stimulate cartilage repair include insulin-like growth factor (IGF-1), Osborn, *J. Orthop. Res.* 7: 35-42 (1989); Florini & Roberts, J. Gerontol. 35: 23-30 (1980); basic fibroblast growth factor (bFGF), Toolan et al., *J. Biomec. Mat. Res.* 41: 244-50 (1998); Sah et al., *Arch. Biochem. Biophys.* 308: 137-47 (1994); bone morphogenetic protein (BMP), Sato & Urist, *Clin. Orthop. Relat. Res.* 183: 180-87 (1984); Chin et al., *Arthritis Rheum.* 34: 314-24 (1991) and transforming growth factor beta (TGF-beta), Hill & Logan, *Prog. Growth Fac. Res.* 4: 45-68 (1992); Guerne et al., *J. Cell Physiol.* 158: 476-84 (1994); Van der Kraan et al., *Ann. Rheum. Dis.* 51: 643-47 (1992).

Insulin-like growth factor (IGF-1) stimulates both matrix synthesis and cell proliferation in culture, K. Osborn. J. Orthop. Res. 7: 35-42 (1989), and insufficiency of IGF-1 may have an etiologic role in the development of osteoarthritis. R. D. Coutts, et al., *Instructional Course Lect.* 47: 487-94, Amer. Acad. Orthop. Surg. Rosemont, Ill. (1997). Some studies indicate that serum IGF-1 concentrations are lower in osteoarthritic patients than control groups, while other studies have found no difference. Nevertheless, both serum IGF-1 levels and chondrocyte responsiveness to IGF-1 decrease with age. J. R. Florini & S. B. Roberts, J. Gerontol. 35: 23-30 (1980). Thus, both the decreased availability of IGF-1 as well as diminished chondrocyte responsiveness to IGF-1 may contribute to cartilage homeostasis and lead to degeneration with advancing age.

IGF-1 has been proposed for the treatment of prevention of osteoarthritis. Intra-articular administration of IGF-1 in combination with sodium pentosan polysulfate (a chondrocyte catabolic activity inhibitor) caused improved histological appearance, and near-normal levels of degradative enzymes (neutral metalloproteinases and collagenase), tissue inhibitors of metalloproteinase and matrix collagen. R. A. Rogachefsky, et al., *Ann. NY Acad. Sci.* 732: 889-95 (1994). The use of IGF-1 either alone or as an adjuvant with other growth factors to stimulate cartilage regeneration has been described in WO 91/19510, WO 92/13565, U.S. Pat. No. 5,444,047, and EP 434,652, Bone morphogenetic proteins (BMPs) are members of the large transforming growth factor beta (TGF-β) family of growth factors. In vitro and in vivo studies have shown that BMP induces the differentiation of mesenchymal cells into chondrocytes. K. Sato & M. Urist, *Clin. Orthop. Relat. Res.* 183: 180-87 (1984). Furthermore, skeletal growth factor and cartilage-derived growth factors have synergistic effects with BMP, as the combination of these growth factors with BMP and growth hormone initiates mesenchymal cell differentiation. Subsequent proliferation of the differentiated cells are stimulated by other factors. D. J. Hill & A Logan, *Prog. Growth Fac. Res.* 4: 45-68 (1992).

Transforming growth factor beta (TGF-β) is produced by osteoblasts, chondrocytes, platelets, activated lymphocytes, and other cells. R. D. Coutts et al., supra. TGF-β can have both stimulatory and inhibitory properties on matrix synthesis and cell proliferation depending on the target cell, dosage, and cell culture conditions. P. Guerne et al., *J. Cell Physiol.* 158: 476-84 (1994); H. Van Beuningen et al., *Ann. Rheum. Dis.* 52: 185-91 (1993); P. Van der Kraan et al., *Ann. Rheum. Dis.* 51: 643-47 (1992). Furthermore, as with IGF-1, TGF-β responsiveness is decreased with age. P. Guerne et al., *J. Cell Physiol.* 158: 476-84 (1994). However, TGF-β is a more potent stimulator of chondrocyte proliferation than other growth factors, including platelet-derived growth factor (PDGF), bFGF, and IGF-1 (Guerne et al., supra), and can stimulate proteoglycan production by chondrocytes. TGF-β also down-regulates the effects of cytokines which stimulate chondrocyte catabolism Van der Kraan et al., supra. In vivo, TGF-β induces proliferation and differentiation of mesenchymal cells into chondrocytes and enhances repair of partial-thickness defects in rabbit articular cartilage. E. B. Hunziker & L. Rosenberg, *Trans. Orthopaed. Res. Soc.* 19: 236 (1994).

While some investigators have focused on the use of certain growth factors to repair cartilage or chondrocyte tissue, others have looked at inhibiting the activity of molecules which induce cartilage destruction and/or inhibit matrix synthesis. One such molecule is the cytokine IL-1alpha, which has detrimental effects on several tissues within the joint, including generation of synovial inflammation and up-regulation matrix metalloproteinases and prostaglandin expression. V. Baragi, et al., *J. Clin. Invest.* 96: 2454-60 (1995); V. M. Baragi et al., *Osteoarthritis Cartilage* 5: 275-82 (1997); C. H. Evans et al., *J. Keukoc. Biol.* 64: 55-61 (1998); *C. H Evans and P. D. Robbins, J. Rheumatol.* 24: 2061-63 (1997); R. Kang et al., *Biochem. Soc. Trans.* 25: 533-37 (1997); R. Kang et al., *Osteoarthritis Cartilage* 5: 139-43 (1997). One means of antagonizing IL-1alpha is through treatment with soluble IL-1 receptor antagonist (IL-1ra), a naturally occurring protein that prevents IL-1 from binding to its receptor, thereby inhibiting both direct and indirect effects of IL-1 on cartilage. In mammals only one protease, named interleukin 1beta-convertase (ICE), can specifically generate mature, active IL-1alpha. Inhibition of ICE has been shown to block IL-1alpha production and may slow arthritic degeneration (reviewed in Martel-Pelletier J. et al. *Front. Biosci.* 4: d694-703). The soluble IL-1 receptor antagonist (IL-1ra), a naturally occurring protein that can inhibit the effects of IL-1 by preventing IL-1 from interacting with chondrocytes, has also been shown to be effective in animal models of arthritis and is currently being tested in humans for its ability to prevent incidence or progression of arthritis. Other cytokines, such as IL-1beta, tumor necrosis factor-alpha, interferon gamma, IL-6, and IL-8 have been linked to increased activation of synovial fibroblast-like cells, chondrocytes and/or macrophages. The inhibition of these cytokines may be of therapeutic benefit in preventing inflammation and cartilage destruction. Molecules which inhibit TNF-alpha activity have been shown to have beneficial effects on the joints of patients with rheumatoid arthritis.

Cartilage matrix degradation is believed to be due to cleavage of matrix molecules (proteoglycans and collagens) by proteases (reviewed in Woessner J F Jr., "Proteases of the extracellular matrix", in Mow, V., Ratcliffe, A. (eds): *Structure and Function of Articular Cartilage*. Boca Raton, Fla., CRC Press, 1994 and Smith R. L., *Front. In Biosci.* 4:d704-712. While the key enzymes involved in matrix breakdown have not yet been clearly identified, matrix metalloproteinases (MMPs) and "aggrecanases" appear to play key roles in joint destruction. In addition, members of the serine and cysteine family of proteinases (for example, the cathepsins and urokinase or tissue plasminogen activator (uPA and tPA)) may also be involved. Plasmin, urokinase plasminogen activator (uPA) and tissue plasminogen activator (tPA) may play an important role in the activation pathway of the metalloproteinases. Evidence connects the closely related group of cathepsin B, L and S to matrix breakdown, and these cathepsins are somewhat increased in OA. Many cytokines, including IL-1, TNF-alpha and LIF induce MMP expression in chondrocytes. Induction of MMPs can be antagonized by TGF-β and IL-4 and potentiated, at least in rabbits, by FGF and PDGF. As shown by animal studies, inhibitors of these proteases (MMPs and aggrecanases) may at least partially protect joint tissue from damage in vivo.

Nitric oxide (NO) may also play a substantial role in the destruction of cartilage. Ashok et al., *Curr. Opin. Rheum.* 10: 263-268 (1998). Unlike normal cartilage which does not produce NO unless stimulated with cytokines such as IL-1, cartilage obtained from osteoarthritic joints produces large amounts of nitric oxide for over 3 days in culture despite the absence of added stimuli. Moreover, inhibition of NO production has been shown to prevent IL-1 mediated cartilage destruction and chondrocyte death as well as progression of osteoarthritis in animal models.

SUMMARY OF THE INVENTION

Applicants have surprisingly found that WISP polypeptides have useful activities, such as the ability to stimulate or enhance chondrocyte differentiation or proliferation, and thus, WISP polypeptides can be useful for the treatment, repair or protection of cartilage, including cartilage damaged as a result of a cartilagenous disorder and/or injury.

In one embodiment, the present invention concerns a method for the treatment of cartilage damaged as a result of a cartilagenous disorder comprising contacting said cartilage with an effective amount of WISP polypeptide. WISP polypeptides contemplated for use in the invention include but are not limited to WISP-1, WISP-2 and WISP-3 polypeptides and variants thereof, described further below. Optionally, the cartilage is articular cartilage, and the amount of WISP polypeptide employed is a therapeutically effective amount. In a preferred embodiment, the cartilagenous disorder is osteoarthritis or rheumatoid arthritis. The methods may be conducted in vivo, such as by administering the therapeutically effective amount of WISP polypeptide to the mammal, or ex vivo, by contacting said cartilage tissue with an effective amount of WISP polypeptide in culture and then transplanting the treated cartilage tissue into the mammal. In addition, the methods may be conducted by employing WISP polypeptide alone as a therapeutic agent, or in combination with an effective amount of a cartilage agent or other therapeutic technique. For example, the WISP polypeptide may be employed in combination with any standard cartilage surgical technique. The WISP polypeptide may be administered prior, after and/or simultaneous to the standard cartilage surgical technique.

In a further embodiment, the present invention concerns a method for the treatment of cartilage damaged by injury or preventing the initial or continued damage comprising contacting said cartilage with an effective amount of WISP polypeptide. More specifically, the injury treated is microdamage or blunt trauma, a chondral fracture, an osteochondral fracture, or damage to tendons, menisci, or ligaments. In a specific aspect, the injury can be the result of excessive mechanical stress or other biomechanical instability resulting from a sports injury or obesity. Alternatively, the present invention concerns a method of treating or facilitating the repair of bone fractures comprising contacting the region of the bone injury with an effective amount of WISP polypeptide.

In another embodiment, the invention concerns a method of enhancing, stimulating or promoting the differentiation of chondrocytes or chondrocyte precursor cells by contacting the chondrocytes or chondrocyte precursor cells with an effective amount of WISP polypeptide.

In another embodiment, the present invention concerns a kit or article of manufacture, comprising WISP polypeptide and a carrier, excipient and/or stabilizer (e.g. a buffer) in suitable packaging. The kit or article preferably contains instructions for using WISP polypeptide to treat cartilage damaged or to prevent initial or continued damage to cartilage as a result of a cartilagenous disorder. Alternatively, the kit may contain instructions for using WISP polypeptide to treat a cartilagenous disorder.

More particular embodiments of the present invention include methods of treating mammalian cartilage cells or tissue, comprising contacting mammalian cartilage cells or tissue damaged from a degenerative cartilagenous disorder (or damaged from an injury) with an effective amount of WISP polypeptide, wherein said WISP polypeptide is a polypeptide selected from the group consisting of:

a) a WISP-1 polypeptide comprising amino acids 23 to 367 of SEQ ID NO:3;
b) a WISP-1 polypeptide comprising amino acids 1 to 367 of SEQ ID NO:3;
c) a WISP-1 polypeptide having at least 90% identity to the polypeptide of a) or b);
d) a biologically active fragment of the polypeptide of a) or b);
e) a WISP-2 polypeptide comprising amino acids 24 to 250 of SEQ ID NO:10;
f) a WISP-2 polypeptide comprising amino acids 1 to 250 of SEQ ID NO:10;
g) a WISP-2 polypeptide having at least 90% identity to the polypeptide of e) of f);
h) a biologically active fragment of the polypeptide of e) or f);
i) a WISP-3 polypeptide comprising amino acids 34 to 372 of SEQ ID NO:9;
j) a WISP-3 polypeptide comprising amino acids 1 to 372 of SEQ ID NO:9;
k) a WISP-3 polypeptide comprising amino acids 16 to 354 of SEQ ID NO:8;
l) a WISP-3 polypeptide comprising amino acids 1 to 354 of SEQ ID NO:8;
m) a WISP-3 polypeptide having at least 90% identity to the polypeptide of i), j), k) or l); and a biologically active fragment of the polypeptide of i), j), k) or l). Optionally, the WISP-1 polypeptide has at least 90% identity to the polypeptide of a) or b), wherein said polypeptide WISP-1 stimulates chondrocyte proliferation or differentiation. Alternatively, the WISP-1 polypeptide is a biologically active fragment of the WISP-1 polypeptide of a) or b), wherein said biologically active fragment stimulates chondrocyte proliferation or differentiation. Optionally, the WISP-2 polypeptide has at least 90% identity to the polypeptide of e) or f), wherein said polypeptide WISP-2 stimulates chondrocyte proliferation or differentiation. Alternatively, the WISP-2 polypeptide is a biologically active fragment of the WISP-2 polypeptide of e) or f), wherein said biologically active fragment stimulates chondrocyte proliferation or differentiation. Optionally, the WISP-3 polypeptide has at least 90% identity to the polypeptide of i), j), k) or l), wherein said polypeptide WISP-3 stimulates chondrocyte proliferation or differentiation. Alternatively, the WISP-3 polypeptide is a biologically active fragment of the WISP-3 polypeptide of i), j), k) or l), wherein said biologically active fragment stimulates chondrocyte proliferation or differentiation. The WISP polypeptides referred to above may be linked to one or more polyethylene glycol molecules. Optionally, the WISP polypeptides may be linked to an epitope tag or immunoglobulin molecule. In the methods, the cartilage may be articular cartilage, and the degenerative cartilagenous disorder may be rheumatoid arthritis or osteoarthritis.

BRIEF DESCRIPTION OF THE DRAWINGS

FIG. 8F represents a negative control in which undigested cells were used but mWISP-1-IgG was omitted from the binding procedure. The relative fluorescence intensity of acquired digital images was measured by morphometric analysis (8G).

FIG. 10 shows the adhesion of different mutants of CHO cells to WISP-1. Cells were taken up in PBS containing 2 mM EDTA and then washed and resuspended in serum free Ham-F12/LGDMEM (50:50) containing 1% BSA. Cell suspension was added to microtiter wells coated with WISP-1 and incubated at 37° C. for 2 hours. The wells were washed 3× with PBS, the supernatant removed and the number of adherent cells measured using CyQUANT from Molecular Probes. Adhesion of CHO-K1 cells to microtiter wells coated with WISP-1 was used as 100% and all values were corrected for nonspecific adhesion to microtiter wells coated with BSA.

FIG. 12 shows the results of a chondrocyte differentiation assay.

In FIG. 15A, cartilage matrix breakdown was determined by measuring the amount of proteoglycans in the media using the DMMB assay. In FIG. 15B, nitric oxide (NO) production was determined by measuring the amount of NO in the media using the Griess reaction.

FIG. 17 shows the amino acid sequences for human WISP-1-IgG (SEQ ID NO:1); mouse WISP-1-IgG (SEQ ID NO:2); "wild-type" human WISP-1 (SEQ ID NO:3); "wild-type" mouse WISP-1 (SEQ ID NO:4); and human IgG tag (SEQ ID NO:5).

FIG. 18 shows the amino acid sequences for WISP-3-IgG (SEQ ID NO:6); "alternate" WISP-3-IgG (SEQ ID NO:7); WISP-3 (SEQ ID NO:8); and WISP-3-"long 5'splicing" (SEQ ID NO:9).

Figure 19:
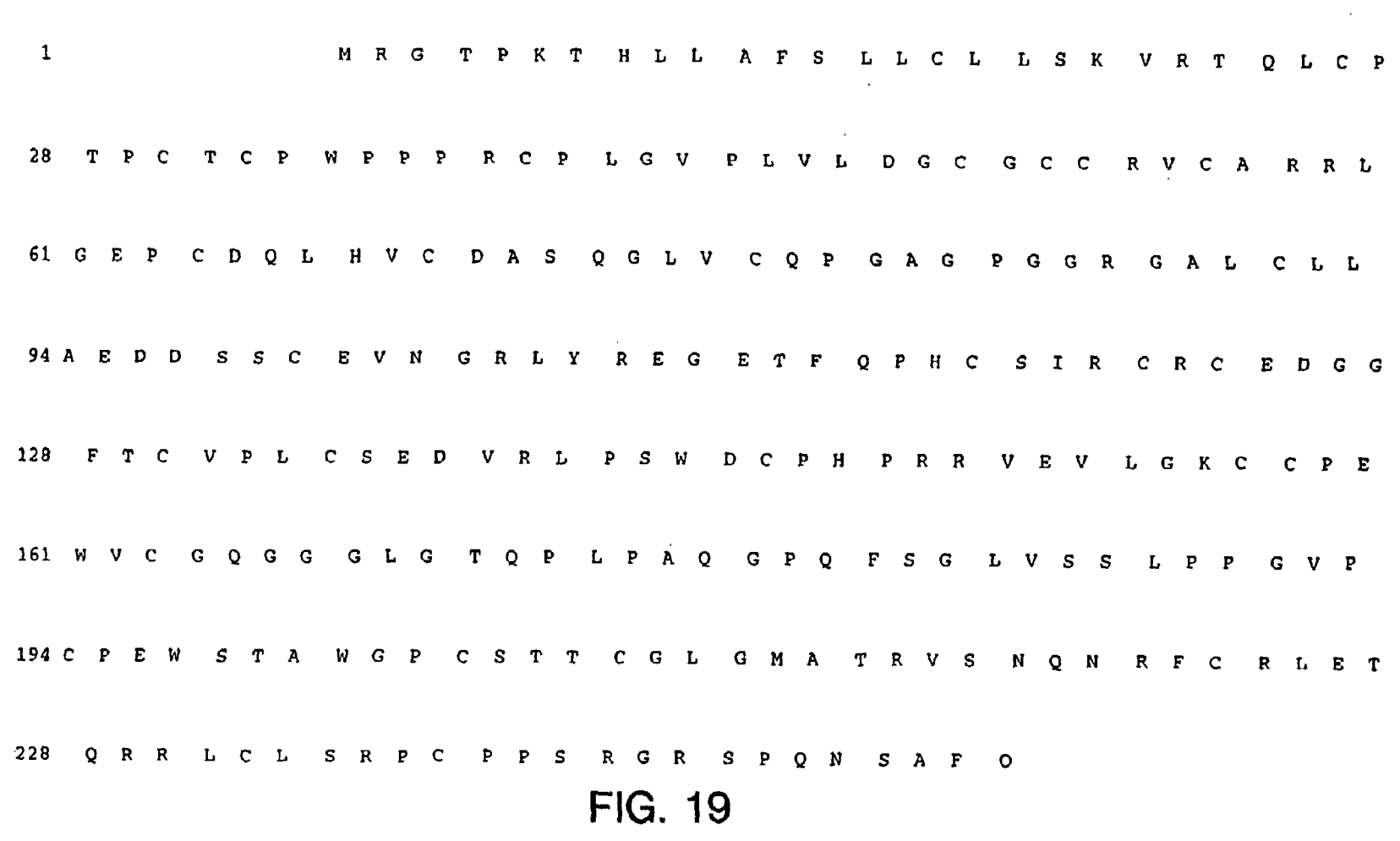

FIG. 19 shows the amino acid sequence for human WISP-2 (SEQ ID NO:10).

DETAILED DESCRIPTION OF THE INVENTION

I. Definitions

Figure 1A:
FIGS. 1A-1G show the binding of WISP-1 to different cell lines. Cells were seeded in chamber slides and cultured overnight. The next day, the non-specific binding sites were blocked and the cells were incubated with 1 nM of mWISP-1-IgG (1A and 1B) or without mWISP-1-IgG (1C) for 1 hour. The cells were washed, fixed and the binding of WISP-1-IgG was detected by immunofluorescence using a biotinylated anti-human IgG antibody and the indirect tyramide substrate amplification procedure followed with FITC conjugated streptavidin. In 1A, there are grouped the cell lines to which mWISP-1-IgG bound. The picture represents the typical fluorescent signal found on a surface of NRK cells following mWISP-1-IgG binding. In 1B, there are grouped the cell lines to which mWISP-1-IgG did not bind. The picture represents the typical fluorescent signal found on surfaces of RAG cells following mWISP-1-IgG binding. The picture in 1C represents the typical fluorescent signal found on surfaces of NRK cells when mWISP-1-IgG was omitted from the binding procedure. Slide mounted human colon tumor sections were brought to room temperature and washed, saturated and incubated for 1 hour in HBS-C/3% BSA and 1 nM WISP-1-Fc (1D and 1E). In parallel, the immunofluorescent detection of vimentin was performed on adjacent sections as described in Example 1 (1F and 1G).
Figure 1B:
Figure 1C:

The term "WISP polypeptide" refers to the family of native-sequence human and mouse WISP proteins and variants described herein whose genes are induced at least by Wnt-1. This term includes WISP-1, WISP-2, and WISP-3 and variants thereof. Such WISP-1, WISP-2 and WISP-3 proteins are described further below and in PCT application WO99/

21998 published May 6, 1999 and in Pennica et al., *Proc. Natl. Acad. Sci.*, 95:14717-14722 (1998).

The terms "WISP-1 polypeptide", "WISP-1 homologue" and grammatical variants thereof, as used herein, encompass native-sequence WISP-1 protein and variants (which are further defined herein). The WISP-1 polypeptide may be isolated from a variety of sources, such as from human tissue types or from another source, or prepared by recombinant or synthetic methods, or by any combination of these and similar techniques.

The terms "WISP-2 polypeptide", "WISP-2 homologue", "PRO261", and "PRO261 polypeptide" and grammatical variants thereof, as used herein, encompass native-sequence WISP-2 protein and variants (which are further defined herein). The WISP-2 polypeptide may be isolated from a variety of sources, such as from human tissue types or from another source, or prepared by recombinant or synthetic methods, or by any combination of these and similar techniques.

The terms "WISP-3 polypeptide", "WISP-3 homologue", and grammatical variants thereof, as used herein, encompass native-sequence WISP-3 protein and variants (which are further defined herein). The WISP-3 polypeptide may be isolated from a variety of sources, such as from human tissue types or from another source, or prepared by recombinant or synthetic methods, or by any combination of these and similar techniques.

A "native-sequence WISP-1 polypeptide" comprises a polypeptide having the same amino acid sequence as a WISP-1 polypeptide derived from nature. Such native-sequence WISP-1 polypeptides can be isolated from nature or can be produced by recombinant or synthetic means. The term "native-sequence WISP-1 polypeptide" specifically encompasses naturally occurring truncated or secreted forms of a WISP-1 polypeptide disclosed herein, naturally occurring variant forms (e.g., alternatively spliced forms or splice variants), and naturally occurring allelic variants of a WISP-1 polypeptide. In one embodiment of the invention, the native-sequence WISP-1 polypeptide is a mature or full-length native-sequence human WISP-1 polypeptide comprising amino acids 23 to 367 of SEQ ID NO:3 herein (also provided previously in FIGS. 3A and 3B (SEQ ID NO:3) shown in WO99/21998 published May 6, 1999) or amino acids 1 to 367 of SEQ ID NO:3 herein (previously provided in FIGS. 3A and 3B (SEQ ID NO:4) shown in WO99/21998), respectively, with or without a N-terminal methionine. Optionally, the human WISP-1 polypeptide comprises the contiguous sequence of amino acids 23 to 367 or amino acids 1 to 367 of SEQ ID NO:3 herein. Optionally, the human WISP-1 polypeptide is encoded by a polynucleotide sequence having the coding nucleotide sequence as in ATCC deposit no. 209533.

In another embodiment of the invention, the native-sequence WISP-1 polypeptide is the full-length or mature native-sequence human WISP-1 polypeptide comprising amino acids 23 to 367 or 1 to 367 of SEQ ID NO:3 herein wherein the valine residue at position 184 or the alanine residue at position 202 has/have been changed to an isoleucine or serine residue, respectively, with or without a N-terminal methionine. In another embodiment of the invention, the native-sequence WISP-1 polypeptide is the full-length or mature native-sequence human WISP-1 polypeptide comprising amino acids 23 to 367 or 1 to 367 of SEQ ID NO:3 herein wherein the valine residue at position 184 and the alanine residue at position 202 has/have been changed to an isoleucine or serine residue, respectively, with or without a N-terminal methionine. In another embodiment of the invention, the native-sequence WISP-1 polypeptide is a mature or full-length native-sequence mouse WISP-1 polypeptide comprising amino acids 23 to 367 of SEQ ID NO:4 herein (previously provided in FIG. 1 (SEQ ID NO:11) shown in WO99/21998), or amino acids 1 to 367 of SEQ ID NO:4 herein (previously provided in FIG. 1 (SEQ ID NO:12) shown in WO99/21998), respectively, with or without a N-terminal methionine.

In another embodiment of the invention, the native-sequence WISP-1 polypeptide is one which is encoded by a nucleotide sequence comprising one of the human WISP-1 splice or other native-sequence variants, including SEQ ID NOS:23, 24, 25, 26, 27, 28, or 29 shown in WO99/21998, with or without a N-terminal methionine.

A "native-sequence WISP-2 polypeptide" or a "native-sequence PRO261 polypeptide" comprises a polypeptide having the same amino acid sequence as a WISP-2 polypeptide derived from nature. Such native-sequence WISP-2 polypeptides can be isolated from nature or can be produced by recombinant or synthetic means. The term "native-sequence WISP-2 polypeptide" specifically encompasses naturally occurring truncated or secreted forms of a WISP-2 polypeptide disclosed herein, naturally occurring variant forms (e.g., alternatively spliced forms or splice variants), and naturally occurring allelic variants of a WISP-2 polypeptide. In one embodiment of the invention, the native-sequence WISP-2 polypeptide is a mature or full-length native-sequence human WISP-2 polypeptide comprising amino acids 1-24 up to 250 of SEQ ID NO:10 herein (previously provided in FIG. 4 (SEQ ID NOS:15, 16, and 56-77) shown in WO99/21998), including amino acids 24 to 250 and amino acids 1 to 250 of SEQ ID NO:10 herein, with or without a N-terminal methionine. Optionally, the human WISP-2 polypeptide comprises the contiguous sequence of amino acids 24 to 250 or amino acids 1 to 250 of SEQ ID NO:10 herein. Optionally, the human WISP-2 polypeptide is encoded by a polynucleotide sequence having the coding nucleotide sequence as in ATCC deposit no. 209391. In another embodiment of the invention, the native-sequence WISP-2 polypeptide is a mature or full-length native-sequence mouse WISP-2 polypeptide comprising amino acids 1-24 up to 251 of the FIG. 2 (SEQ ID NOS:19, 20, and 78-99) shown in WO99/21998, including amino acids 24 to 251 and amino acids 1 to 251 of the FIG. 2 (SEQ ID NOS:19 and 20, respectively) shown in WO99/21998, with or without a N-terminal methionine.

A "native-sequence WISP-3 polypeptide" comprises a polypeptide having the same amino acid sequence as a WISP-3 polypeptide derived from nature. Such native-sequence WISP-3 polypeptides can be isolated from nature or can be produced by recombinant or synthetic means. The term "native-sequence WISP-3 polypeptide" specifically encompasses naturally occurring truncated or other forms of a WISP-3 polypeptide disclosed herein, naturally occurring variant forms (e.g., alternatively spliced forms or splice variants), and naturally occurring allelic variants of a WISP-3 polypeptide. In one embodiment of the invention, the native-sequence WISP-3 polypeptide is a mature or full-length, native-sequence human WISP-3 polypeptide comprising amino acids 34 to 372 of SEQ ID NO:9 herein (previously provided in. 6A and 6B (SEQ ID NO:32) of WO99/21998) or amino acids 1 to 372 of SEQ ID NO:9 herein (previously provided in FIGS. 6A and 6B (SEQ ID NO:33) shown in WO99/21998), respectively, with or without a N-terminal methionine. In another embodiment of the invention, the native-sequence WISP-3 polypeptide is a mature or full-length, native-sequence human WISP-3 polypeptide comprising amino acids 16 to 354 of SEQ ID NO:8 herein (previously provided in FIGS. 7A and 7B (SEQ ID NO:36) shown in WO 99/21998) or amino acids 1 to 354 of SEQ ID NO:8 herein (previously provided in FIGS. 7A and 7B (SEQ ID NO:37) shown in WO99/21998), respectively, with or without a N-terminal methionine. Optionally, the human WISP-3 polypeptide comprises the contiguous sequence of amino acids 34 to 372 or amino acids 1 to 372 of SEQ ID NO:9 herein. Optionally, the human WISP-3 polypeptide comprises the contiguous sequence of amino acids 16 to 354 or 1 to 354 of SEQ ID NO:8 herein. Optionally, the human WISP-3 polypeptide is encoded by a polynucleotide sequence having the coding nucleotide sequence as in ATCC deposit no. 209707.

The term "WISP-1 variant" means an active WISP-1 polypeptide as defined below having at least about 80%, preferably at least about 85%, more preferably at least about 90%, most preferably at least about 95% amino acid sequence identity with human mature WISP-1 having the deduced amino acid sequence of amino acids 23 to 367 of SEQ ID NO:3, and/or with human full-length WISP-1 having the deduced amino acid sequence of amino acids 1 to 367 of SEQ ID NO:3, and/or with mouse mature WISP-1 having the deduced amino acid sequence shown in FIG. 1 (SEQ ID NO:11) shown in WO99/21998 and/or with mouse full-length WISP-2 having the deduced amino acid sequence shown in the FIG. 1 (SEQ ID NO:12) of WO99/21998. Such variants include, for instance, WISP-1 polypeptides wherein one or more amino acid residues are added to, or deleted from (i.e., fragments), the N- or C-terminus of the full-length or mature sequences of SEQ ID NO:3, including variants from other species, but excludes a native-sequence WISP-1 polypeptide.

The term "WISP-2 variant" or "PRO261 variant" means an active WISP-2 polypeptide as defined below having at least about 80%, preferably at least about 85%, more preferably at least about 90%, most preferably at least about 95% amino acid sequence identity with human mature WISP-2 having the putative deduced amino acid sequence of amino acids 24 to 250 of SEQ ID NO:10, and/or with human full-length WISP-2 having the deduced amino acid sequence of amino acids 1 to 250 of SEQ ID NO:10, and/or with mouse mature WISP-2 having the putative deduced amino acid sequence shown in FIG. 2 (SEQ ID NO:19) of WO99/21998, and/or with mouse full-length WISP-2 having the deduced amino acid sequence shown in FIG. 2 (SEQ ID NO:20) of WO99/21998. Such variants include, for instance, WISP-2 polypeptides wherein one or more amino acid residues are added to, or deleted from (i.e., fragments), the N- or C-terminus of the full-length and putative mature sequences of SEQ ID NO:10, including variants from other species, but excludes a native-sequence WISP-2 polypeptide.

The term "WISP-3 variant" means an active WISP-3 polypeptide as defined below having at least about 80%, preferably at least about 85%, more preferably at least about 90%, most preferably at least about 95% amino acid sequence identity with human mature WISP-3 having the deduced amino acid sequence of amino acids 34 to 372 of SEQ ID NO:9, and/or with human full-length WISP-3 having the deduced amino acid sequence of amino acids 1 to 372 of SEQ ID NO:9, and/or with human mature WISP-3 having the deduced amino acid sequence of amino acids 16 to 354 of SEQ ID NO:8, or with human full-length WISP-3 having the deduced amino acid sequence of amino acids 1 to 354 of SEQ ID NO:8. Such variants include, for instance, WISP-3 polypeptides wherein one or more amino acid residues are added to, or deleted from (i.e., fragments), the N- or C-terminus of the full-length or mature sequences of SEQ ID NO:9 or SEQ ID NO:8, including variants from other species, but excludes a native-sequence WISP-3 polypeptide.

"Percent (%) amino acid sequence identity" with respect to the WISP polypeptide sequences identified herein is defined as the percentage of amino acid residues in a candidate sequence that are identical with the amino acid residues in such WISP sequences identified herein, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained by using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

"Stringent conditions" are those that (1) employ low ionic strength and high temperature for washing, 0.015 M sodium chloride/0.0015 M sodium citrate/0.1% sodium dodecyl sulfate at 50° C.; (2) employ during hybridization a denaturing agent, such as formamide, 50% (vol/vol) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC and 0.1% SDS; or (4) employ a buffer of 10% dextran sulfate, 2×SSC (sodium chloride/sodium citrate), and 50% formamide at 55° C., followed by a high-stringency wash consisting of 0.1× SSC containing EDTA at 55° C.

"Moderately stringent conditions" are described in Sambrook et al., *Molecular Cloning: A Laboratory Manual* (New York: Cold Spring Harbor Laboratory Press, 1989), and include the use of a washing solution and hybridization conditions (e.g., temperature, ionic strength, and percent SDS) less stringent than described above. An example of moderately stringent conditions is a condition such as overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc., as necessary to accommodate factors such as probe length and the like.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the WISP natural environment will not be present ordinarily, however, isolated polypeptide will be prepared by at least one purification step.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

A "liposome" is a small vesicle-composed of various types of lipids, phospholipids and/or surfactant which is useful for delivery of a drug (such as the WISP polypeptides and WISP variants disclosed herein) to a mammal. The components of the liposome are commonly arranged in a bilayer formation, similar to the lipid arrangement of biological membranes.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" in the context of the WISP polypeptides or WISP variants of the invention refers to form(s) of proteins of the invention which retain the biologic and/or immunologic activities of a native or naturally-occurring WISP polypeptide, wherein "biological" activity refers to a biological function (either inhibitory or stimulatory) caused by a native or naturally-occurring WISP polypeptide other than the ability to serve as an antigen in the production of an antibody against an antigenic epitope possessed by a native or naturally-occurring polypeptide of the invention. Similarly, an "immunological" activity refers to the ability to serve as an antigen in the production of an antibody against an antigenic epitope possessed by a native or naturally-occurring polypeptide of the invention.

"Biological activity" in the context of a WISP polypeptide or WISP variant herein is used to refer to the ability of such molecules to promote the regeneration of and/or prevent the destruction of cartilage or to enhance or promote chondrocyte differentiation or proliferation (i.e., differentiation of a precursor cell into a mature chondrocyte). Optionally, the cartilage is articular cartilage and the regeneration and/or destruction of the cartilage is associated with an injury or a degenerative cartilagenous disorder. For example, such biological activity may be quantified by the inhibition of proteoglycan (PG) release from articular cartilage, the increase in PG synthesis in articular cartilage, the inhibition of the production of NO, etc.

The term "cartilagenous disorder" refers generally to a disease manifested by symptoms of pain, stiffness and/or limitation of motion of the affected body parts. Included within the scope of "cartilagenous disorder" is "degenerative cartilagenous disorder"—a disorder characterized, at least in part, by degeneration or metabolic derangement of connective tissues of the body, including not only the joints or related structures, including muscles, bursae (synovial membrane), tendons and fibrous tissue, but also the growth plate. In one embodiment, the term includes "articular cartilage disorder" which is characterized by disruption of the smooth articular cartilage surface and degradation of the cartilage matrix. Additional pathologies include nitric oxide production, and inhibition or reduction of matrix synthesis.

Included within the scope of "articular cartilage disorder" are osteoarthritis (OA) and rheumatoid arthritis (RA). OA is characterized by localized asymmetric destruction of the cartilage commensurate with palpable bony enlargements at the joint margins. OA typically affects the interphalangeal joints of the hands, the first carpometacarpal joint, the hips, the knees, the spine, and some joints in the midfoot, while large joints, such as the ankles, elbows and shoulders tend to be spared. OA can be associated with metabolic diseases such as hemochromatosis and alkaptonuria, developmental abnormalities such as developmental dysplasia of the hips (congenital dislocation of the hips), limb-length discrepancies, including trauma and inflammatory arthritides such as gout, septic arthritis, neuropathic arthritis. OA may also develop after extended biomechanical instability, such as resulting from sports injury or obesity.

Rheumatoid arthritis (RA) is a systemic, chronic, autoimmune disorder characterized by symmetrical synovitis of the joint and typically affects small and large diarthroid joints alike. As RA progresses, symptoms may include fever, weight loss, thinning of the skin, multiorgan involvement, scleritis, corneal ulcers, the formation of subcutaneous or subperiosteal nodules and even premature death. The symptoms of RA often appear during youth and can include vasculitis, atrophy of the skin and muscle, subcutaneous nodules, lymphadenopathy, splenomegaly, leukopaenia and chronic anaemia.

Furthermore, the term "degenerative cartilagenous disorder" may include systemic lupus erythematosus and gout, amyloidosis or Felty's syndrome. Additionally, the term covers the cartilage degradation and destruction associated with psoriatic arthritis, osteoarthrosis, acute inflammation (e.g., yersinia arthritis, pyrophosphate arthritis, gout arthritis (arthritis urica), septic arthritis), arthritis associated with trauma, ulcerative colitis (e.g., Crohn's disease), multiple sclerosis, diabetes (e.g., insulin-dependent and non-insulin dependent), obesity, giant cell arthritis and Sjögren's syndrome.

Examples of other immune and inflammatory diseases, at least some of which may be treatable by the methods of the invention include, juvenile chronic arthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis) autoimmune inflammatory diseases (e.g., allergic encephalomyelitis, multiple sclerosis, insulin-dependent diabetes mellitus, autoimmune uveoretinitis, thyrotoxicosis, scleroderma, systemic lupus erythematosus, rheumatoid arthritis, inflammatory bowel disease (e.g., Crohn's disease, ulcerative colitis, regional enteritis, distal ileitis, granulomatous enteritis, regional ileitis, terminal ileitis), autoimmune thyroid disease, pernicious anemia) and allograft rejection, diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis, Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. Infectious diseases including viral diseases such as AIDS (HIV infection), hepatitis A, B, C, D, and E, herpes, etc., bacterial infections, fungal infections, protozoal infections, parasitic infections, and respiratory syncytial virus, human immunodeficiency virus, etc.) and allergic disorders, such as anaphylactic hypersensitivity, asthma, allergic rhinitis, atopic dermatitis, vernal conjunctivitis, eczema, urticaria and food allergies, etc.

"Treatment" is an intervention performed with the intention of preventing the development or altering the pathology of a disorder. Accordingly, "treatment" refers to both therapeutic treatment and prophylactic or preventative measures, wherein the object is to prevent or slow down (lessen) the targeted pathological condition or disorder. Those in need of treatment include those already with the disorder as well as those in which the disorder is to be prevented. In treatment of a degenerative cartilagenous disorder, a therapeutic agent may directly decrease or increase the magnitude of response of a pathological component of the disorder, or render the disease more susceptible to treatment by other therapeutic agents, e.g. antibiotics, antifungals, anti-inflammatory agents, chemotherapeutics, etc.

The term "effective amount" is the minimum concentration of WISP polypeptide which causes, induces or results in either a detectable improvement or repair in damaged cartilage or a measureable protection from the continued or induced cartilage destruction in an isolated sample of cartilage matrix (e.g., retention of proteoglycans in matrix, inhibition of proteoglycan release from matrix, stimulation of proteoglycan synthesis). Furthermore a "therapeutically effective amount" is the minimum concentration (amount) of WISP polypeptide administered to a mammal which would be effective in at least attenuating a pathological symptom (e.g. causing, inducing or resulting in either a detectable improvement or repair in damaged articular cartilage or causing, inducing or resulting in a measurable protection from the continued or initial cartilage destruction, improvement in range of motion, reduction in pain, etc.) which occurs as a result of injury or a degenerative cartilagenous disorder.

"Cartilage agent" may be a growth factor, cytokine, small molecule, antibody, piece of RNA or DNA, virus particle, peptide, or chemical having a beneficial effect upon cartilage, including peptide growth factors, catabolism antagonists and osteo-, synovial- or anti-inflammatory factors. Alternatively, "cartilage agent" may be a peptide growth factor—such as any of the fibroblast growth factors (e.g., FGF-1, FGF-2, ... FGF-21, etc.), IGF's (I and II), TGF-βs (1-3), BMPs (1-7), or members of the epidermal growth factor family such as EGF, HB-EGF, TGF-β—which could enhance the intrinsic reparative response of cartilage, for example by altering proliferation, differentiation, migration, adhesion, or matrix production by chondrocytes. Alternatively, a "cartilage agent" may be a factor which antagonizes the catabolism of cartilage (e.g., IL-1 receptor antagonist (IL-1ra), NO inhibitors, IL1-beta convertase (ICE) inhibitors, factors which inhibit activity of IL-6, IL-8, LIF, IFN-gamma, or TNF-alpha activity, tetracyclines and variants thereof, inhibitors of apoptosis, MMP inhibitors, aggrecanase inhibitors, inhibitors of serine and cysteine proteinases such as cathepsins and urokinase or tissue plasminogen activator (uPA and tPA). Alternatively still, cartilage agent includes factors which act indirectly on cartilage by affecting the underlying bone (i.e., osteofactors, e.g. bisphosphonates or osteoprotegerin) or the surrounding synovium (i.e., synovial factors) or anti-inflammatory factors (e.g., anti-TNF-alpha (including anti-TNF-alpha antibodies such as Remicade®, as well as TNF receptor immunoadhesins such as Enbrel®), IL-1ra, IL-4, IL-10, IL-13, NSAIDs). For a review of cartilage agent examples, please see Martel-Pelletier et al., *Front. Biosci.* 4: d694-703 (1999); Hering, T. M., *Front. Biosci.* 4: d743-761 (1999).

"Chronic" administration refers to administration of the factor(s) in a continuous mode as opposed to an acute mode, so as to maintain the initial therapeutic effect (activity) for an extended period of time.

"Intermittent" administration is treatment that is done not consecutively without interruption, but rather is cyclic in nature.

"Mammal" for purposes of treatment refers to any animal classified as a mammal, including humans, domestic and farm animals, and zoo, sports, or pet animals, such as dogs, horses, cats, cattle, pigs, hamsters, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®, hyaluronic acid (HA).

II. Methods and Compositions of the Invention

In accordance with the methods of the present invention, various WISP polypeptides may be employed for treatment of degenerative cartilagenous disorders as well as various other immune and immune related conditions. Such WISP polypeptides include the polypeptides referred to herein as WISP-1, WISP-2, and WISP-3 and variants thereof (as well as fusion proteins thereof such as epitope tagged forms or Ig-fusion constructs thereof). The WISP polypeptides may be used in vivo as well as ex vivo. Optionally, the WISP polypeptides are used in the form of pharmaceutical compositions, described in further detail below.

Degenerative cartilagenous disorders contemplated by the invention include Rheumatoid arthritis (RA). RA is a systemic, autoimmune, degenerative disease that can cause symmetrical disruptions in the synovium of both large and small diarthroidal joints. As the disease progresses, symptoms of PA may include fever, weight loss, thinning of the skin, multiorgan involvement, scleritis, corneal ulcers, formation of subcutaneous or subperiosteal nodules and premature death. RA symptoms typically appear during youth, extra-articular manifestations can affect any organ system, and joint destruction is symmetrical and occurs in both large and small joints alike. Extra-articular symptoms can include vasculitis, atrophy of the skin and muscle, subcutaneous nodules, lymphadenopathy, splenomegaly, leukopaenia and chronic anaemia. RA tends to be heterogeneous in nature with a variable disease expression and is associated with the formation of serum rheumatoid factor in 90% of patients sometime during the course of the illness. RA patients typically also have a hyperactive immune system. The majority of people with RA have a genetic susceptibility associated with increased activation of class II major histocompatibility complex molecules on monocytes and macrophages. These histocompatibility complex molecules are involved in the presentation of antigen to activated T cells bearing receptors for these class II molecules. The genetic predisposition to RA is supported by the prevalence of the highly conserved leukocyte antigen DR subtype Dw4, Dw14 and Dw15 in human patients with very severe disease.

Osteoarthritis (OA) is another degenerative cartilagenous disorder that involves a localized disease that affects articular cartilage and bone and results in pain and diminished joint function. OA may be classified into two types: primary and secondary. Primary OA refers to the spectrum of degenerative joint diseases for which no underlying etiology has been determined. Typically, the joint affected by primary OA are the interphalangeal joints of the hands, the first carpometacarpal joints, the hips, the knees, the spine, and some joints in the midfoot. Large joints, such as the ankles, elbows and shoulders tend to be spared in primary OA. In contrast, secondary OA often occurs as a result of defined injury or trauma. Secondary arthritis can also be found in individuals with metabolic diseases such as hemochromatosis and alkaptonuria, developmental abnormalities such as developmental dysplasia of the hips (congenital dislocation of the hips) and limb-length discrepancies, obesity, inflammatory arthritides such as rheumatoid arthritis or gout, septic arthritis, and neuropathic arthritis.

The degradation associated with OA initially appears as fraying and fibrillation of the articular cartilage surface as proteoglycans are lost from the matrix. With continued joint use, surface fibrillation progresses, defects penetrate deeper into the cartilage, and pieces of cartilage tissue are lost. In addition, bone underlying the cartilage (subchondral bone) thickens, and, as cartilage is lost, bone becomes slowly exposed. With asymmetric cartilage destruction, disfigurement can occur. Bony nodules, called osteophytes, often form at the periphery of the cartilage surface and occasionally grow over the adjacent eroded areas. If the surface of these bony outgrowths is permeated, vascular outgrowth may occur and cause the formation of tissue plugs containing fibrocartilage.

Since cartilage is avascular, damage which occurs to the cartilage layer but does not penetrate to the subchondral bone, leaves the job of repair to the resident chondrocytes, which have little intrinsic potential for replication. However, when the subchondral bone is penetrated, its vascular supply allows a triphasic repair process to take place. The suboptimal cartilage which is synthesized in response to this type of damage, termed herein "fibrocartilage" because of its fibrous matrix, has suboptimal biochemical and mechanical properties, and is thus subject to further wear and destruction. In a diseased or damaged joint, increased release of metalloproteinases (MMPs) such as collagenases, gelatinases, stromelysins, aggrecanases, and other proteases, leads to further thinning and loss of cartilage. In vitro studies have shown that cytokines such as IL-1alpha, IL-1beta, TNF-alpha, PDGF, GM-CSF, IFN-gamma, TGF-beta, LIF, IL-2 and IL-6, IL-8 can alter the activity of synovial fibroblast-like cells, macrophage, T cells, and/or osteoclasts, suggesting that these cytokines may regulate cartilage matrix turnover in vivo.

The mechanical properties of cartilage are determined by its biochemical composition. While the collagen architecture contributes to the tensile strength and stiffness of cartilage, the compressibility (or elasticity) is due to its proteoglycan component. In healthy articular cartilage, type II collagen predominates (comprising about 90-95%), however, smaller amounts of types V, VI, IX, and XI collagen are also present. Cartilage proteoglycans (PG) include hydrodynamically large, aggregating PG, with covalently linked sulfated glycosaminoglycans, as well as hydrodynamically smaller non-aggregating PG such as decorin, biglycan and lumican.

Injuries to cartilage may fall into three categories: (1) microdamage or blunt trauma, (2) chondral fractures, and (3) osteochondral fractures.

Microdamage to chondrocytes and cartilage matrix may be caused by a single impact, through repetitive blunt trauma, or with continuous use of a biomechanically unstable joint. Metabolic and biochemical changes such as those found in the early stages of degenerative arthritis can be replicated in animal models involving repetitive loading of articular cartilage. Radin et al., *Clin. Orthop. Relat. Res.* 131: 288-93 (1978). Such experiments, along with the distinct pattern of cartilage loss found in arthritic joints, highlight the role that biomechanical loading plays in the loss of homeostasis and integrity of articular cartilage in disease. Radin et al., *J Orthop Res.* 2: 221-234 (1984); Radin et al., *Semin Arthritis Rheum* (suppl. 2) 21: 12-21 (1991); Wei et al., *Acta Orthop Scand* 69: 351-357 (1998). While chondrocytes may initially be able to replenish cartilage matrix with proteoglycans at a basal rate, concurrent damage to the collagen network may increase the rate of loss and result in irreversible degeneration. Buckwalter et al., *J. Am. Acad. Orthop. Surg.* 2: 192-201 (1994).

Chondral fractures are characterized by disruption of the articular surface without violation of the subchondral plate. Chondrocyte necrosis at the injury site occurs, followed by increased mitotic and metabolic activity of the surviving chondrocytes bordering the injury which leads to lining of the clefts of the articular surface with fibrous tissue. The increase in chondrocyte activity is transitory, and the repair response results in insufficient amount and quality of new matrix components.

Osteochondral fractures, the most serious of the three types of injuries, are lesions crossing the tidemark into the underlying subchondral plate. In this type of injury, the presence of subchondral vasculature elicits the three-phase response typically encountered in vascular tissues: (1) necrosis, (2) inflammation, and (3) repair. Initially the lesion fills with blood and clots. The resulting fibrin clot activates an inflammatory response and becomes vascularized repair tissue, and the various cellular components release growth factors and cytokines including transforming growth factor beta (TGF-beta), platelet-derived growth factor (PDGF), bone morphogenic proteins, and insulin-like growth factors I and II. Buckwalter et al., *J. Am. Acad. Orthop. Surg.* 2: 191-201 (1994).

The initial repair response associated with osteochondral fractures is characterized by recruitment, proliferation and differentiation of precursors into chondrocytes. Mesenchymal stem cells are deposited in the fibrin network, which eventually becomes a fibrocartilagenous zone. F. Shapiro et al., *J. Bone Joint Surg.* 75: 532-53 (1993); N. Mitchell and N. Shepard, *J. Bone Joint Surg.* 58: 230-33 (1976). These stem cells, which are believed to come from the underlying bone marrow rather than the adjacent articular surface, progressively differentiate into chondrocytes. At six to eight weeks after injury, the repair tissue contains chondrocyte-like cells in a matrix of proteoglycans and predominantly type II collagen, with some type I collagen. T. Furukawa et al., *J. Bone Joint Surg.* 62: 79-89 (1980); J. Cheung et al., *Arthritis Rheum.* 23: 211-19 (1980); S. O. Hjertquist & R. Lemperg, *Calc. Tissue Res.* 8: 54-72 (1971). However, this newly deposited matrix degenerates, and the chondroid tissue is replaced by more fibrous tissue and fibrocartilage and a shift in the synthesis of collagen from type II to type I. H. S. Cheung et al., *J. Bone Joint Surg.* 60: 1076-81 (1978); D. Hamerman, "Prospects for medical intervention in cartilage repair," *Joint cartilage degradation: Basic and clinical aspects*, Eds. Woessner J F et al., (1993); Shapiro et al., *J. Bone Joint Surg.* 75: 532-53 (1993); N. Mitchell & N. Shepard, *J. Bone Joint Surg.* 58: 230-33 (1976); S. O. Hjertquist & R. Lemperg, *Calc. Tissue Res.* 8: 54-72 (1971). Early degenerative changes include surface fibrillation, depletion of proteoglycans, chondrocyte cloning and death, and vertical fissuring from the superficial to deep layers. At one year post-injury, the repair tissue is a mixture of fibrocartilage and hyaline cartilage, with a substantial amount of type I collagen, which is not found in appreciable amounts in normal articular cartilage. T. Furukawa, et al., *J. Bone Joint Surg.* 62: 79-89 (1980).

While inflammation does not appear to be the initiating event in osteoarthritis, inflammation does occur in osteoarthritic joints. The inflammatory cells (i.e. monocytes, macrophages, and neutrophils) which invade the synovial lining after injury and during inflammation produce metalloproteinases as well as catabolic cyokines which can contribute to further release of degradative enzymes. Although inflammation and joint destruction do not show perfect correlation in all animal models of arthritis, agents such as IL-4, IL-10 and IL-13 which inhibit inflammation also decrease cartilage and bone pathology in arthritic animals (reviewed in Martel-Pelletier J. et al. *Front. Biosci.* 4: d694-703). Application of agents which inhibit inflammatory cytokines may slow OA progression by countering the local synovitis which occurs in OA patients.

OA involves not only the degeneration of articular cartilage leading to eburnation of bone, but also extensive remodelling of subchondral bone resulting in the so-called sclerosis of this tissue. These bony changes are often accompanied by the formation of subchondral cysts as a result of focal resorption. Agents which inhibit bone resorption, i.e. osteoprotegerin or bisphosphonates have shown promising results in animal model of arthritis. Kong et al. *Nature* 402: 304-308 (1999).

In systemic lupus erythematosus, the central mediator of disease is the production of auto-reactive antibodies to self proteins/tissues and the subsequent generation of immune-mediated inflammation. These antibodies either directly or indirectly mediate tissue injury. Although T lymphocytes have not been shown to be directly involved in tissue damage, T lymphocytes are required for the development of auto-reactive antibodies. The genesis of the disease is thus T lymphocyte dependent. Multiple organs and systems are affected clinically including kidney, lung, musculoskeletal system, mucocutaneous, eye, central nervous system, cardiovascular system, gastrointestinal tract, bone marrow and blood.

Juvenile chronic arthritis is a chronic idiopathic inflammatory disease which begins often at less than 16 years of age and which has some similarities to RA. Some patients which are rheumatoid factor positive are classified as juvenile rheumatoid arthritis. The disease is sub-classified into three major categories: pauciarticular, polyarticular, and systemic. The arthritis can be severe and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing sponylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+ T lymphocyte, a cell which targets antigen presented by class I MHC molecules. CD8+ T cells may react against the class I MHC allele HLA-B27 as if it were a foreign peptide expressed by MHC class I molecules. It has been hypothesized that an epitope of HLA-B27 may mimic a bacterial or other microbial antigenic epitope and thus induce a CD8+ T cells response.

The WISP polypeptides employed in the invention may be prepared by any suitable method, including recombinant expresssion techniques. Recombinant expression technology is well known to those skilled in the art, and optional materials and methods are described in PCT application, WO 99/21998. Optionally, the WISP polypeptides are expressed using host cell such as CHO cells, *E. coli* or yeast cells. The WISP polypeptides may comprise full length polypeptides (defined herein), or variant forms thereof, as well as other modified forms of the WISP polypeptides (such as by fusing or linking to an immunoglobulin, epitope tag, leucine zipper or other non-proteinaceous polymer).

Immunoadhesin molecules are contemplated for use in the methods herein. WISP immunoadhesins may comprise various forms of WISP, such as the full length polypeptide as well as variant or fragment forms thereof. In one embodiment, the molecule may comprise a fusion of the WISP with an immunoglobulin or a particular region of an immunoglobulin. For a bivalent form of the immunoadhesin, such a fusion could be to the Fc region of an IgG molecule. For the production of immunoglobulin fusions, see also U.S. Pat. No. 5,428,130 issued Jun. 27, 1995 and Chamow et al., *TIBTECH*, 14:52-60 (1996).

In another embodiment, the WISP polypeptide may be covalently modified by linking the polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337. Such pegylated forms of the WISP polypeptide may be prepared using techniques known in the art.

Leucine zipper forms of these molecules are also contemplated by the invention. "Leucine zipper" is a term in the art used to refer to a leucine rich sequence that enhances, promotes, or drives dimerization or trimerization of its fusion partner (e.g., the sequence or molecule to which the leucine zipper is fused or linked to). Various leucine zipper polypeptides have been described in the art. See, e.g., Landschulz et al., *Science,* 240:1759 (1988); U.S. Pat. No. 5,716,805; WO 94/10308; Hoppe et al., *FEBS Letters,* 344:1991 (1994); Maniatis et al., *Nature,* 341:24 (1989). Those skilled in the art will appreciate that a leucine zipper sequence may be fused at either the 5' or 3' end of the WISP polypeptide.

The WISP polypeptides of the present invention may also be modified in a way to form chimeric molecules by fusing the receptor polypeptide to another, heterologous polypeptide or amino acid sequence. Preferably, such heterologous polypeptide or amino acid sequence is one which acts to oligimerize the chimeric molecule. In one embodiment, such a chimeric molecule comprises a fusion of the WISP polypeptide with a tag polypeptide which provides an epitope to which an anti-tag antibody can selectively bind. The epitope tag is generally placed at the amino- or carboxyl-terminus of the polypeptide. The presence of such epitope-tagged forms of the WISP polypeptide can be detected using an antibody against the tag polypeptide. Also, provision of the epitope tag enables the WISP polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.,* 8:2159-2165 (1988)]; the c-myc tag and the 8F9, 3C7, 6E10, G4, B7 and 9E10 antibodies thereto [Evan et al., *Molecular and Cellular Biology,* 5:3610-3616 (1985)]; and the Herpes Simplex virus glycoprotein D (gD) tag and its antibody [Paborsky et al., *Protein Engineering,* 3(6):547-553 (1990)). Other tag polypeptides include the Flag-peptide [Hopp et al., *BioTechnology,* 6:1204-1210 (1988)]; the KT3 epitope peptide [Martin et al., *Science,* 255:192-194 (1992)]; an α-tubulin epitope peptide [Skinner et al., *J. Biol. Chem.*, 266:15163-15166 (1991)]; and the T7 gene 10 protein peptide tag (Lutz-Freyermuth et al., *Proc. Natl. Acad. Sci. USA,* 87:6393-6397 (1990)].

Formulations of WISP polypeptides employable with the invention can be prepared by mixing the WISP polypeptide having the desired degree of purity with optional pharmaceutically acceptable carriers, excipients or stabilizers (*Remington's Pharmaceutical Sciences* 16th edition, Osol, A. Ed. [1980]). Such therapeutic formulations can be in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, dextrins, or hyaluronan; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN®, PLURONICS® or polyethylene glycol (PEG).

The WISP polypeptides also may be prepared by entrapping in microcapsules prepared, for example by coacervation techniques or by interfacial polymerization, for example, hydroxymethylcellulose or gelatin-microcapsules and poly-(methylmethacrylate) microcapsules, respectively. Such preparations can be administered in colloidal drug delivery systems (for example, liposomes, albumin microspheres, microemulsions, nanoparticles and nanocapsules) or in macroemulsions. Such techniques are disclosed in *Remington's Pharmaceutical Sciences,* 16th Edition (or newer), Osol A. Ed. (1980).

Where sustained-release or extended-release administration of the WISP polypeptides is desired in a formulation with release characteristics suitable for the treatment of any disease or disorder requiring administration of such polypeptides, microencapsulation is contemplated. Microencapsulation of recombinant proteins for sustained release has been successfully performed. See, e.g., Johnson et al., *Nat. Med.* 2: 795-799 (1996); Yasuda, *Biomed. Ther.* 27: 1221-1223 (1993); Hora et al., *Bio/Technology* 8: 755-758 (1990); Cleland, "Design and Production of Single Immunization Vaccines Using Polylactide Polyglycolide Microsphere Systems" in *Vaccine Design: The Subunit and Adjuvant Approach*, Powell and Newman, eds., (Plenum Press: New York, 1995), pp. 439-462; WO 97/03692, WO 96/40072, WO 96/07399 and U.S. Pat. No. 5,654,010.

Suitable examples of sustained-release preparations include semipermeable matrices of solid hydrophobic polymers containing the active molecule, which matrices are in the form of shaped articles, e.g. films, or microcapsules. Examples of sustained-release matrices include one or more polyanhydrides (e.g., U.S. Pat. Nos. 4,891,225; 4,767,628), polyesters such as polyglycolides, polylactides and polylactide-co-glycolides (e.g., U.S. Pat. No. 3,773,919; U.S. Pat. No. 4,767,628; U.S. Pat. No. 4,530,840; Kulkarni et al., *Arch. Surg.* 93: 839 (1966)), polyamino acids such as polylysine, polymers and copolymers of polyethylene oxide, polyethylene oxide acrylates, polyacrylates, ethylene-vinyl acetates, polyamides, polyurethanes, polyorthoesters, polyacetylnitriles, polyphosphazenes, and polyester hydrogels (for example, poly(2-hydroxyethyl-methacrylate), or poly(vinylalcohol)), cellulose, acyl substituted cellulose acetates, non-degradable polyurethanes, polystyrenes, polyvinyl chloride, polyvinyl fluoride, poly(vinylimidazole), chlorosulphonated polyolefins, polyethylene oxide, copolymers of L-glutamic acid and gamma-ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. Additional non-biodegradable polymers which may be employed are polyethylene, polyvinyl pyrrolidone, ethylene vinylacetate, polyethylene glycol, cellulose acetate butyrate and cellulose acetate propionate.

Alternatively, sustained release formulations may be composed of degradable biological materials. Biodegradable polymers are attractive drug formulations because of their biocompatibility, high responsibility for specific degradation, and ease of incorporating the active drug into the biological matrix. For example, hyaluronic acid (HA) may be crosslinked and used as a swellable polymeric delivery vehicle for biological materials. U.S. Pat. No. 4,957,744; Valle et al., *Polym. Mater. Sci. Eng.* 62: 731-735 (1991). HA polymer grafted with polyethylene glycol has also been prepared as an improved delivery matrix which reduced both undesired drug leakage and the denaturing associated with long term storage at physiological conditions. Kazuteru, M., *J. Controlled Release* 59:77-86 (1999). Additional biodegradable polymers which may be used are poly(caprolactone), polyanhydrides, polyamino acids, polyorthoesters, polycyanoacrylates, poly(phosphazines), poly(phosphodiesters), polyesteramides, polydioxanones, polyacetals, polyketals, polycarbonates, polyorthocarbonates, degradable and nontoxic polyurethanes, polyhydroxylbutyrates, polyhydroxyvalerates, polyalkylene oxalates, polyalkylene succinates, poly(malic acid), chitin and chitosan.

Alternatively, biodegradable hydrogels may be used as controlled release delivery vehicles for biological materials and drugs. Through the appropriate choice of macromers, membranes can be produced with a range of permeability, pore sizes and degradation rates suitable for a wide variety of biomolecules.

Alternatively, sustained-release delivery systems for biological materials and drugs can be composed of dispersions. Dispersions may further be classified as either suspensions or emulsions. In the context of delivery vehicles for biological materials, suspensions are a mixture of very small solid particles which are dispersed (more or less uniformly) in a liquid medium. The solid particles of a suspension can range in size from a few nanometers to hundreds of microns, and include microspheres, microcapsules and nanospheres. Emulsions, on the other hand, are a mixture of two or more immiscible liquids held in suspension by small quantities of emulsifiers. Emulsifiers form an interfacial film between the immiscible liquids and are also known as surfactants or detergents. Emulsion formulations can be both oil in water (o/w) wherein water is in a continuous phase while the oil or fat is dispersed, as well as water in oil (w/o), wherein the oil is in a continuous phase while the water is dispersed. One example of a suitable sustained-release formulation is disclosed in WO 97/25563. Additionally, emulsions for use with biological materials include multiple emulsions, microemulsions, microdroplets and liposomes. Microdroplets are unilamellar phospholipid vesicles that consist of a spherical lipid layer with an oil phase inside. E.g., U.S. Pat. No. 4,622,219 and U.S. Pat. No. 4,725, 442. Liposomes are phospholipid vesicles prepared by mixing water-insoluble polar lipids with an aqueous solution.

Alternatively, the sustained-release formulations of WISP polypeptides may be developed using poly-lactic-coglycolic acid (PLGA), a polymer exhibiting a strong degree of biocompatibility and a wide range of biodegradable properties. The degradation products of PLGA, lactic and glycolic acids, are cleared quickly from the human body. Moreover, the degradability of this polymer can be adjusted from months to years depending on its molecular weight and composition. For further information see Lewis, "Controlled Release of Bioactive Agents from Lactide/Glycolide polymer," in *Biogradable Polymers as Drug Delivery Systems* M. Chasin and R. Langeer, editors (Marcel Dekker: New York, 1990), pp. 1-41.

The encapsulated polypeptides or polypeptides in extended-release formulation may be imparted by formulating the polypeptide with a "water-soluble polyvalent metal salts" which are non-toxic at the release concentration and temperature. Exemplary "polyvalent metals" include the following cations: $Ca^{2+}$, $Mg^{2+}$, $Zn^{2+}$, $Fe^{2+}$, $Fe^{3+}$, $Cu^{2+}$, $Sn^{2+}$, $Sn^{2+}$, $Al^{2+}$ and $Al^{3+}$. Exemplary anions which form water-soluble salts with the above polyvalent metal cations include those formed by inorganic acids and/or organic acids. Such water-soluble salts have solubility in water (at 20° C.) of at least about 20 mg/ml, alternatively 100 mg/ml, alternatively 200 mg/ml.

Suitable inorganic acids that can be used to form the "water soluble polyvalent metal salts" include hydrochloric, sulfuric, nitric, thiocyanic and phosphoric acid. Suitable organic acids that can be used include aliphatic carboxylic acid and aromatic acids. Aliphatic acids within this definition may be defined as saturated or unsaturated $C_{2-9}$ carboxylic acids (e.g., aliphatic mono-, di- and tri-carboxylic acids). Commonly employed water soluble polyvalent metal salts which may be used to help stabilize the encapsulated polypeptides of this invention include, for example: (1) the inorganic acid metal salts of halides (e.g., zinc chloride, calcium chloride), sulfates, nitrates, phosphates and thiocyanates; (2) the aliphatic carboxylic acid metal salts calcium acetate, zinc acetate, calcium proprionate, zinc glycolate, calcium lactate, zinc lactate and zinc tartrate; and (3) the aromatic carboxylic acid metal salts of benzoates (e.g., zinc benzoate) and salicylates.

In order for the formulations to be used for in vivo administration, they should be sterile. The formulation may be readily rendered sterile by filtration through sterile filtration membranes, prior to or following lyophilization and reconstitution. The therapeutic compositions herein generally are placed into a container having a sterile access port, for example, an intravenous solution bag or vial having a stopper pierceable by a hypodermic injection needle.

For treatment of the mammal in vivo, the route of administration is in accordance with known methods, e.g., injection or infusion by intravenous, intraperitoneal, intramuscular, intraarterial, intralesional or intraarticular routes, topical administration, by sustained release or extended-release means. Optionally the active compound or formulation is injected directly or locally into the afflicted cartilagenous region or articular joint. The treatment contemplated by the invention may also take the form of gene therapy.

Dosages' and desired drug concentrations of pharmaceutical compositions employable with the present invention may vary depending on the particular use envisioned. The determination of the appropriate dosage or route of administration is well within the skill of an ordinary physician. Animal experiments can provide reliable guidance for the determination of effective doses for human therapy. Interspecies scaling of effective doses can be performed following the principles laid down by Mordenti, J. and Chappell, W. "The use of interspecies scaling in toxicokinetics" in *Toxicokinetics and New Drug Development*, Yacobi et al., Eds., Pergamon Press, New York 1989, pp. 42-96.

When in vivo administration of WISP polypeptides are employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344 or 5,225,212. It is anticipated that different formulations will be effective for different treatments and different disorders, and that administration intended to treat a specific organ or tissue, may necessitate delivery in a manner different from that to another organ or tissue.

The formulations used herein may also contain more than one active compound as necessary for the particular indication being treated, preferably those with complementary activities that do not adversely affect each other. The WISP polypeptide may be administered in combination with a cytotoxic agent, cytokine or growth inhibitory agent. Such molecules are present in combinations and amounts that are effective for the intended purpose. It may be desirable to also administer antibodies against other immune disease associated or tumor associated antigens, such as antibodies which bind to CD20, CD11a, CD 40, CD18, ErbB2, EGFR, ErbB3, ErbB4, or vascular endothelial growth factor (VEGF). Alternatively, or in addition, two or more antibodies binding the same or two or more different antigens disclosed herein may be coadministered to the patient. Sometimes, it may be beneficial to also administer one or more cytokines to the patient. In one embodiment, the polypeptides of the invention are coadministered with a growth inhibitory agent. For example, the growth inhibitory agent may be administered first, followed by a WISP polypeptide of the invention. Still other agents may be administered in combination with WISP polypeptide, such as agents like decorin or biglycan. Simultaneous administration or sequential administration is also contemplated.

The present method may also be administered in combination with any standard cartilage surgical technique. Standard surgical techniques are surgical procedures which are commonly employed for therapeutic manipulations of cartilage, including: cartilage shaving, abrasion chondroplasty, laser repair, debridement, chondroplasty, microfracture with or without subchondral bone penetration, mosaicplasty, cartilage cell allografts, stem cell autografts, costal cartilage grafts, chemical stimulation, electrical stimulation, perichondral autografts, periosteal autografts, cartilage scaffolds, shell (osteoarticular) autografts or allografts, or osteotomy. These techniques are described and discussed in greater detail in Frenkel et al., *Front. Bioscience* 4: d671-685 (1999).

In a preferred embodiment, the WISP polypeptides are used in combination with microfracture surgery. Microfracture surgery techniques are known in the art and generally entail surgical drilling into the mammal's bone marrow cavity. Fibrin clots then form, filling the defect in the mammals's body. Subsequently, fibrocartilage forms.

It is contemplated that WISP polypeptides can be employed to treat cartilage or chondrocyte cells ex vivo. Such ex vivo treatment may be useful in transplantation and particularly, autologous transplantation. For instance, treatment of cells or tissue(s) containing such cartilage or chondrocyte cells with WISP polypeptide, and optionally, with one or more other therapies, such as described above, can be employed to regenerate cartilage tissue of induce differentiation of precursor chondrocyte cells prior to transplantation in a recipient mammal.

Cells or tissue(s) containing cartilage or chondrocyte cells are first obtained from a donor mammal. The cells or tissue(s) may be obtained surgically and preferably, are obtained aseptically. The cells or tissue(s) are then treated with WISP polypeptide, and optionally, with one or more other therapies, such as described above.

The treated cells or tissue(s) can then be infused or transplanted into a recipient mammal. The recipient mammal may be the same individual as the donor mammal or may be another, heterologous mammal.

The progress or effectiveness of the therapies described herein can be readily monitored by conventional techniques and assays known to the skilled practicioner.

The activity or effects of the WISP polypeptides described herein on cartilage or chondrocytes can be determined without undue experimentation using various in vitro or in vivo assays. By way of example, several such assays are described below.

In one assay, the synthetic and prophylactic potential of WISP polypeptide on intact cartilage can be tested. To this end, proteoglycan (PG) synthesis and breakdown, and nitric oxide release are measured in treated articular cartilage explants. Proteoglycans are the second largest component of the organic material in articular cartilage (Kuettner, K. E. et al., *Articular Cartilage Biochemistry*, Raven Press, New York, USA (1986), p.456; Muir, H., *Biochem. Soc. Tran.* 11: 613-622 (1983); Hardingham, T. E., *Biochem. Soc. Trans.* 9: 489-497 (1981). Since proteoglycans help determine the physical and chemical properties of cartilage, the decrease in cartilage PGs which occurs during joint degeneration leads to loss of compressive stiffness and elasticity, an increase in hydraulic permeability, increased water content (swelling), and changes in the organization of other extracellular components such as collagens. Thus, PG loss is an early step in the progression of degenerative cartilaginous disorders, one which further perturbs the biomechanical and biochemical stability of the joint. PGs in articular cartilage have been extensively studied because of their likely role in skeletal growth and disease. Mow, V. C., & Ratcliffe, A. *Biomaterials* 13: 67-97 (1992). Proteoglycan breakdown, which is increased in diseased joints, can be measured by quantitating PGs released into the media by articular cartilage explants using the colorimetric DMMB assay. Farndale and Buttle, *Biochem. Biophys. Acta* 883: 173-177 (1985). Incorporation of $^{35}$S-sulfate into proteoglycans is used to measure proteoglycan synthesis.

The evidence linking interleukin-1alpha, IL-1beta, and degenerative cartilagenous diseases is substantial. For example, high levels of IL-1alpha (Pelletier J P et al., "Cytokines and inflammation in cartilage degradation" in *Osteoarthritic Edition of Rheumatic Disease Clinics of North America*, Eds. R W Moskowitz, Philadelphia, W D. Saunders Company, 1993, p.545-568) and IL-1 receptors (Martel-Pelletier et al., *Arthritis Rheum.* 35: 530-540 (1992) have been found in diseased joints, and IL-1alpha induces cartilage matrix breakdown and inhibits synthesis of new matrix molecules. Baragi et al., *J. Clin. Invest.* 96: 2454-60 (1995); Baragi et al., *Osteoarthritis Cartilage* 5: 275-82 (1997); Evans et al., *J. Leukoc. Biol.* 64: 55-61 (1998); Evans et al., *J. Rheumatol.* 24: 2061-63 (1997); Kang et al., *Biochem. Soc. Trans.* 25: 533-37 (1997); Kang et al., *Osteoarthritis Cartilage* 5: 139-43 (1997). Because of the association of IL-1alpha with disease, the WISP polypeptide can also be assayed in the presence of IL-1alpha. The ability of the WISP polypeptide to not only have positive effects on cartilage, but also to counteract the catabolic effects of IL-1alpha is strong evidence of the protective effect exhibited by the WISP polypeptide. In addition, such and activity suggests that the WISP polypeptide could inhibit the degradation which occurs in arthritic conditions, since catabolic events initiated by IL-1alpha are also induced by many other cytokines and since antagonism of IL-1alpha activity has been shown to reduce the progression of osteoarthritis. Arend, W. P. et al., *Ann. Rev. Immunol.* 16: 27-55 (1998).

The production of nitric oxide (NO) can be induced in cartilage by catabolic cytokines such as IL-1. Palmer, R M J et al., *Biochem. Biophys. Res. Commun.* 193: 398-405 (1993). NO has also been implicated in the joint destruction which occurs in arthritic conditions. Ashok et al., *Curr. Opin. Rheum.* 10: 263-268 (1998). Unlike normal (undiseased or uninjured) cartilage, osteoarthritic cartilage produced significant amounts of nitric oxide ex vivo, even in the absence of added stimuli such as interleukin-1 or lipopolysaccharide (LPS). In vivo animal models suggest that inhibition of nitric oxide production reduces progression of arthritis. Pelletier, J P et al., *Arthritis Rheum.* 7: 1275-86 (1998); van de Loo et al., *Arthritis Rheum.* 41: 634-46 (1998); Stichtenoth, D. O. and Frolich J. C., *Br. J. Rheumatol.* 37: 246-57 (1998). In vitro, nitric oxide exerts detrimental effects on chondrocyte function, including inhibition of collagen and proteoglycan synthesis, inhibition of adhesion to the extracellular matrix, and enhancement of cell death (apoptosis). Higher concentrations of nitrite are found in synovial fluid from osteoarthritic patients than in fluid from rheumatoid arthritic patients. Renoux et al., *Osteoarthritis Cartilage* 4: 175-179 (1996). Furthermore, animal models suggest that inhibition of nitric oxide production reduces progression of arthritis. Pelletier, J. P. et al., *Arthritis Rheum.* 7: 1275-86 (1998); van de Loo et al., *Arthritis Rheum.* 41: 634-46 (1998); Stichtenoth, D. O. & Frolich, J. C., *Br. J. Rheumatol.* 37: 246-57 (1998). Since NO also has effects on other cells, the presence of NO within the articular joint could increase vasodilation and permeability, potentiate cytokine release by leukocytes, and stimulate angiogenic activity. Since NO likely play a role in both the erosive and the inflammatory components of joint diseases, a factor which decreases nitric oxide production would likely be beneficial for the treatment of degenerative cartilagenous disorders.

The assay to measure nitric oxide production is based on the principle that 2,3-diaminonapthalene (DAN) reacts with nitrite under acidic conditions to form 1-(H)-naphthotriazole, a fluorescent product. As NO is quickly metabolized into nitrite ($NO_2^{-1}$) and nitrate ($NO_3^{-1}$), detection of nitrite is one means of detecting (albeit undercounting) the actual NO produced by cartilage.

The ability of a WISP polypeptide to enhance, promote or maintain the viability of chondrocytes in cultures in the absence of serum or other growth factors can also be examined. Articular chondrocytes are first prepared by removal of the extracellular matrix and cultured in a monolayer, which is believed to approximate the latter stages of cartilage disorders when the matrix has been depleted. The assay is a colorimetric assay that measures the metabolic activity of the cultured cells based on the ability of viable cells to cleave the yellow tetrazolium salt MTT to form purple formazan crystals. This cellular reduction reaction involves the pyridine nucleotide cofactors NADH and NADPH. Berridge, M. V. & Tan, A. S., *Arch. Biochem. Biophys.* 303: 474 (1993). The solubilized product is spectrophotometrically quantitated on an ELISA reader.

Yet another assay examines the effects of WISP polypeptides on proteoglycan synthesis in patellae (kneecaps) of mice. This assay uses intact cartilage (including the underlying bone) and thus tests factors under conditions which approximate the in vivo environment of cartilage. Compounds are either added to patellae in vitro, or are injected into knee joints in vivo prior to analysis of proteoglycan synthesis in patellae ex vivo. As has been shown previously, in vivo treated patellae show distinct changes in PG synthesis ex vivo (Van den Berg et al., *Rheum. Int.* 1: 165-9 (1982); Vershure, P. J. et al., *Ann. Heum. Dis.* 53: 455-460 (1994); and Van de Loo et al., *Arthrit. Rheum.* 38: 164-172 (1995). In this model, the contralateral joint of each animal can be used as a control.

A guinea pig model can be employed to measure the effects of WISP polypeptides on both the stimulation of PG synthesis and inhibition of PG release in articular cartilage explants from a strain of guinea pigs, Dunkin Hartley (DH), which spontaneously develops knee osteoarthritis (OA). Most other animal models which cause rapidly progressing joint breakdown resemble secondary OA more than the slowly evolving human primary OA. In contrast, DH guinea pigs have naturally occurring slowly progressive, non-inflammatory OA-like changes. Because the highly reproducible pattern of cartilage breakdown in these guinea pigs is similar to that seen in the human disorder, the DH guinea pig is a well-accepted animal model for osteoarthritis. Young et al., "Osteoarthritis", Spontaneous animal models of human disease vol. 2, pp. 257-261, Acad. Press, New York. (1979); Bendele et al., *Arthritis Rheum.* 34: 1180-1184; Bendele et al., *Arthritis Rheum.* 31: 561-565 (1988); Jimenez et al., *Laboratory Animal Sciences* 47 (6): 598-601 (1997); Wei et al., *Acta Orthop Scand* 69: 351-357 (1998)). Initially, these animals develop a mild OA that is detectable by the presence of minimal histologic changes. However, the disease progresses, and by 16-18 months of age, moderate to severe cartilage degeneration within the joints is observed. As a result, the effect of the WISP polypeptide on the cartilage matrix of the DH guinea pigs over the progression of the disease would be indicative of the therapeutic effect of the compound in the treatment of OA at different stages of joint destruction.

The metabolic changes associated with diabetes mellitus (diabetes) affect may other organ and musculo-skeletal systems of the afflicted organism. For example, in humans, the incidence of musculoskeletal injuries and disorders is increased with the onset of diabetes, and diabetes is considered a risk factor for the development of arthritis.

A syndrome similar to diabetes can be induced in animals by administration of streptozotocin (STZ). Portha B. et al., *Diabete Metab.* 15: 61-75 (1989). By killing pancreatic cells which produce insulin, STZ decreases the amount of serum insulin in treated animals. STZ-induced diabetes is associated with atrophy and depressed collagen content of connective tissues including skin, bone and cartilage. Craig, R. G. et al., *Biochim. Biophys. Acta* 1402: 250-260 (1998). In this assay, the patellae of treated STZ-treated mice are incubated in the presence of the WISP polypeptide and the resulting matrix synthesis is analyzed. The ability of the WISP polypeptide to increase or restore the level of PG synthesis to that of untreated controls is indicative of the therapeutic potential.

In another embodiment of the invention, kits and articles of manufacture containing materials useful for the diagnosis or treatment of the disorders described above are provided. The article of manufacture comprises a container and an instruction. Suitable containers include, for example, bottles, vials, syringes, and test tubes. The containers may be formed from a variety of materials such as glass or plastic. The container holds a composition which is effective for diagnosing or treating the degenerative cartilagenous disorder, and may have a sterile access port (for example the container may be an intravenous solution bag or a vial having a stopper pierceable by a hypodermic injection needle). The active agent in the composition will typically be a WISP polypeptide. The composition can comprise any or multiple ingredients disclosed herein. The instruction on, or associated with, the container indicates that the composition is used for diagnosing or treating the condition of choice. For example, the instruction could indicate that the composition is effective for the treatment of osteoarthritis arthritis, rheumatoid arthritis or any other degenerative cartilagenous disorder. The article of manufacture may further comprise a second container comprising a pharmaceutically-acceptable buffer, such as phosphate-buffered saline, Ringer's solution and dextrose solution. Alternatively, the composition may contain any of the carriers, excipients and/or stabilizers mentioned herein. It may further include other materials desirable from a commercial and user standpoint, including other buffers, diluents, filters, needles, syringes, and package inserts with instructions for use.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., *Molecular Cloning: A Laboratory Manual*, Cold Spring Harbor Press N.Y., 1989, Ausubel et al., *Current Protocols in Molecular Biology*, Green Publishing Associates and Wiley Interscience, N.Y., 1989; Innis et al., *PCR Protocols: A Guide to Methods and Applications*, Academic Press, Inc., N.Y., 1990; Harlow et al., *Antibodies: A Laboratory Manual*, Cold Spring Harbor Press, Cold Spring Harbor, 1988; Gait, M. J., *Oligonucleotide Synthesis*, IRL Press, Oxford, 1984; R. I. Freshney, *Animal Cell Culture*, 1987; Coligan et al., *Current Protocols in Immunology*, 1991.

Example 1

In the assays described below, the following methods and materials were employed:

Materials: Chondroitin sulfate A from bovine trachea, chondroitin sulfate C from shark cartilage, hyaluronidase (EC 3.2.1.45) from bovine testes and chondroitinase AC II (EC 4.2.2.5) from *Artherobacter aurenscens* were purchased from Calbiochem (San Diego). Chondroitin sulfate B, heparin and heparan sulfate from porcine intestinal mucosa, decorin and biglycan from bovine articular cartilage, chondroitinase C, chondroitinase B and heparinase I (EC 4.2.2.7) from *Flavobacterium hepanium* were obtained from Sigma. Chondroitin sulfate D from shark cartilage and chondroitin sulfate E from squid cartilage were purchased from United States Biological (Swampscott, Mass.). Neuramimidase (EC 3.2.2.18) from *Vibrio Cholera*, chondroitinase ABC (EC 4.2.2.4), protease free from *Proteus vulgaris*, Complete EDTA-free protease inhibitors cocktail tablets and fatty acid ultra free BSA fraction V were purchased from Roche Molecular Biochemicals (Indianapolis, Ind.). Chondroitin-4-sulfatase (EC 3.1.6.9) and chondroitin-6-sulfatase (EC 3.1.6.10) from *Proteus vulgaris* were from ICN Biomedicals (Aurora, OI). Horseradish peroxidase conjugated and biotinylated goat anti-human IgG, Fc fragment specific and biotinylated anti-sheep IgG was purchased from Jackson ImmunoResearch (Costa Mesa, Calif.). Proteinase K (EC 3.4.21.14) ready-to-use, Texas red conjugated steptavidin and anti-vimentin monoclonal antibody (clone Vim 3B4) was from Dako (Carpinteria, Calif.). 5-chloromethylfluoroscein diacetate (5-CFDA) and Hoechst 33342 were purchased from Molecular Probes (Eugene, Oreg.). The Renaissance TSA indirect amplification kit was bought from NEN Life Science Products (Boston, Mass.). Vectashield mounting media and biotinylated horse anti-mouse IgG were obtained from Vector (Burlingame, Calif.).

Full length murine WISP-1 (Pennica et al., *Proc. Natl. Acad. Sci.*, 95:14717-14722 (1998); WO 99/21998) was cloned into an expression vector encoding the human IgG1 Fc region downstream of the WISP-1 sequence as described previously for TNFR1 (Ashkenazi et al., *Proc. Natl. Acad. Sci.*, 88:10535-10539 (1991)). The resulting recombinant fusion protein (WISP-1-Fc) was synthesized in a baculovirus expression system using Sf9 insect cells and purified to homogeneity from serum-free conditioned medium by affinity chromatography on a protein A-Sepharose Fast Flow (Pharmacia Biotech, Sweden) column. Unadsorbed proteins were washed out with 50 mM sodium phosphate buffer containing 1 M NaCl. WISP-1-Fc was eluted with 100 mM glycine pH 2.5 and the pH was neutralized with 0.1 volume of 3M Tris-HCl pH 8. After dialysis (20 mM Tris-HCl, pH 7.5, 150 mM) the purified protein was concentrated by ultrafiltration using Centriprep-30 (Millipore Corp., Bedford, Mass.) and the purity estimated by SDS-PAGE and silver staining. The experiments were repeated at least three times with three different batches of protein expressed and purified at different times and similar results were obtained.

Cell Culture: NRK (normal rat kidney fibroblasts), Hs 597.5k (human normal skin fibroblasts), Hs 839.T (human skin melanoma fibroblasts), Hs 908.5k (human skin melanoma fibroblasts), COLO 320DM (human colon adenocarcinoma cells), RAG (mouse renal adenocarcinoma cells), 293 (human kidney epithelial cells), HUVEC (human umbilical vein endothelial cells), and WM-266-4 (human skin melanoma epithelial cells) were obtained from American Type Culture Collection, Manassas, Va. The cells were maintained in Low glucose Dulbecco's modified Eagle's Medium/Ham F-12 (1:1) supplemented with 10% FBS at 37° C. under 5% $CO_2$.

Cell Binding: Cells were plated in 8 well plastic chamber slides and maintained overnight at 37° C., 5% $CO_2$. The next day the cells were washed with PBS and the wells were blocked for 30 minutes at room temperature with 3% BSA in HBS-C buffer (25 mM Hepes, pH 7.2, 150 NaCl, 3 mM $CaCl_2$, 3 mM $MgSO_4$, 5 mM KCl, Complete protease inhibitors cocktail). When indicated, cells were washed and incubated 2 hours at 37° C. with 0.1 U of the different lyases before blocking. (see, Vacherot et al., *J. Biol. Chem.*, 274: 7741-7747 (1999)). The cells were incubated with 1 nM mWISP-1-IgG for 1 hour at room temperature, washed and incubated with 0.2 µg/ml biotinylated anti-human IgG Fc' in HBS-C/3% BSA for 30 minutes at room temperature. The signal was amplified using the TSA indirect kit (NEN Dupont) according to the manufacturer instructions. After a 30 minutes incubation with 1:200 FITC conjugated streptavidin (DAKO), the slides were mounted using Vectashield containing 1 μg/ml Hoechst 33342 (Molecular Probes) and visualized under a Nikon Eclipse 800 fluorescent microscope. The images were acquired using a Photometrics 300 CCD Cooled Camera. Measurement of the fluorescence intensity of cells was as described previously with modifications (Szurdoki et al., *Anal. Biochem.,* 291:219-228 (2001)). Briefly, images of a minimum of three separate fields containing an average of 90 cells were acquired and stored as electronic files. The threshold was defined as the lowest intensity of the 1% brightest pixels in a negative control executed without WISP-1-Fc. The fluorescence signal for a cell population was defined as the total pixel intensity over the threshold divided by the cell number.

Solid Phase Binding Assay: Proteins were diluted in 50 μl (total volume) of PBS, applied to polystyrene microtiter wells and incubated at 40 C overnight. The next day the wells were washed three times with 300 μl of HBS-c containing 0.3% BSA and the non-specific binding sites were blocked for 1 hour at room temperature with 200 μl HBS-C/3% BSA. The buffer was aspirated and 50 μl of 0.5 nM WISP-1-IgG in HBS-C/3% BSA was incubated for 2 hours at room temperature. The wells were washed and incubated for 1 hour with 50 μl of 2 μg/ml horseradish peroxidase conjugated goat anti-human IgG Fc' in HBS-C/3%. At the end of the incubation, the wells were washed 6 times with 200 μl of PBS containing 0.05% Tween-20 and the signal was visualized using 100 μl of the horseradish peroxidase chromogenic substrate TMB (KPL). The reaction was stopped with 100 μl of 1 M phosphoric acid and the OD at 450 nm was measured. Non-specific WISP-1-Fc binding was determined in parallel incubations by omitting microtiter well coating. No signal was generated when WISP-1-Fc was omitted.

Purification of WISP-1 Binding Factors: Human skin fibroblasts were cycled between serum containing and serum free culture media every 3 days. The serum free conditioned media was concentrated on a Centriprep-30 (Millipore, Bedford, Mass.). The buffer was then changed by sequentially adding 20 mM Tris-HCL pH 7.4, 300 mM NaCl and reconcentrating. The concentrate (150 μg protein/ml) was snap frozen and stored at −80° C. until used. The concentrated conditioned media was thawed, filtered and applied on a Mono Q anion exchange column equilibrated in 20 mM Tris-HCl pH 7.4, containing 300 mM NaCl. The column was washed and the adsorbed proteins were eluted using a linear gradient of NaCl (300 mM-2 M) in the same buffer. Fractions of 500 μl were analyzed for WISP-1 binding activity.

Protein Identification by Mass Spectrometry: The fractions containing the WISP-1 binding activity were pooled, denatured, reduced and applied on 4-15% gradient acrylamide SDS-PAGE with or without a previous incubation for 2 hours at 37° C. with 0.1 U of chondroitinase ABC. The gels were silver stained and the protein bands demonstrating a mobility change upon chondroitinase ABC digestion were excised and digested in situ with trypsin as previously described by Arnott et al., *Electrophoresis,* 19:968-980 (1998). Tryptic peptides were extracted and analyzed by microcapillary reverse-phase liquid chromatography-mass spectrometry. Peptide mixtures were loaded onto 100 μm i.d., 10 cm long fused silica capillary columns packed with 5 μm C18 beads (238MSB5; Vydac, Hesperia, Calif.) and eluted with an acetonitrile gradient directly into the microelectrospray ionization source of an ion trap mass spectrometer (LCQ; Thermoquest, San Jose, Calif.). A flow rate of 500 μl/min was obtained by a pre-column split from 25 μl/min delivered by the HPLC (Ultra PlusII; Microtech Scientific, Sunnyvale, Calif.; Arnott et al., supra). Automated, data-dependent acquisition of mass spectra provided molecular mass (MS) and sequence data (MS/MS) for peptides as they eluted from the column. Proteins were identified by correlation of MS/MS data with entries in a non-redundant protein sequence database using the Sequest program (Gatlin, C., Eng, J., Cross, S., Detter, J. and Yates III, *Analytical Chemistry,* 72:757-763 (2000)). Protein matches were confirmed by manual interpretation of the spectra.

Immunofluorescence: Slide-mounted human colon tumor sections were brought to room temperature, fixed with 70% ethanol for 10 minutes and the non-specific binding sites were saturated with PBS/3% BSA containing 1.5% normal serum for 20 minutes. The sections were incubated for 1 hour with 0.125 microgram/ml anti-vimentin antibody, washed with PBS and further incubated for 30 minutes with 2 microgram/ml biotinylated anti-mouse IgG antibody. The signal was amplified using the TSA indirect kit according to manufacturer instructions. After a 30 minute incubation with 1:1000 Texas red conjugated streptavidin, the slides were mounted using Vectashield containing 1 microgram/ml Hoechst 33342 and visualized under a Nikon Eclipse 800 fluorescent microscope. Images were acquired using a Photometrics 300 CCD Cooled Camera. The negative control executed in absence of primary antibody did not reveal any fluorescent staining.

The immunofluorescent detection of decorin on human skin fibroblasts was executed using a similar protocol. $8 \times 10^3$ cells were plated in chamber slides and cultured overnight. The next day, the cells were washed and incubated at 37° C. for 15 minutes with fresh medium containing 5 microgram/ml 5-CFDA. After washing, the non-specific binding sites were saturated with HBS-C/3% BSA for 30 minutes at room temperature. The cells were then incubated for 1 hour at room temperature with 1:4000 sheep anti-human decorin antibody in HBS-C/0.1% BSA. The cells were washed, fixed with 4% paraformaldehyde/PBS for 10 minutes, washed and further incubated for 30 minutes with 2 microgram/ml biotinylated anti-sheep IgG. The signal was amplified using the TSA indirect kit. After a 30 minute incubation with 1:1000 Texas red conjugated streptavidin, the slides were mounted using Vectashield containing 1 microgram/ml Hoechst 33342 and visualized under a Nikon Eclipse 800 fluorescent microscope. Images were acquired using a Photometrics 300 CCD Cooled Camera. The negative control executed in absence of primary antibody did not reveal any fluorescent staining.

Analytical Methods: SDS-PAGE was performed according to Laemli, *Nature,* 227:680-685 (1970) using a Bio-Rad Mini-PROTEAN II vertical slab gel electrophoresis apparatus. The apparent molecular mass was determined using the broad range molecular weight standards from Bio-Rad. Protein was determined using the Bio-Rad Protein Assay silver stain Dye Reagent and bovine serum albumin standard.

A. Binding of WISP-1 to Various Cell Lines and Human Colon Tumor Sections

The binding of a chimeric recombinant mouse WISP-1 bearing a human immunoglobulin Fc fragment tag to various cells in culture was analyzed. Cells were seeded in chamber slides and cultured overnight. The next day, the non-specific binding sites were blocked and the cells were incubated with 1 nM of mWISP-1-IgG or without mWISP-1-IgG for 1 hour. The cells were washed, fixed and the binding of WISP-1-IgG was detected by immunofluorescence using a biotinylated anti-human IgG antibody and the indirect tyramide substrate amplification procedure followed with FITC conjugated streptavidin.

As summarized in FIG. 1, the binding of WISP-1 could only be seen at the surface of fibroblastic cell lines. As an example, the binding of WISP-1 to NRK cells is illustrated (FIG. 1A). Moreover, the protein also bound to fibroblasts of rat or human origin whether they were normal or from skin melanoma. On the other hand, no fluorescent signal could be detected when mouse renal adenocarcinoma, human colon adenocarcinoma, human kidney epithelial cells, human umbilical vein endothelial cells, or human skin melanoma epithelial cells were used. As an example, the binding of WISP-1 to RAG cells is illustrated (FIG. 1B). No signal could be detected when the addition of WISP-1 was omitted or when an unrelated biotinylated secondary antibody was used (FIG. 1C).

Binding of WISP-1 to human colon tumor sections was evaluated using in situ ligand binding procedures. Slide mounted human colon tumor sections were brought to room temperature and immediately incubated for 4 minutes in 35 mM acetic acid (pH 3.5) containing 3 mM $CaCl_2$, 3 mM $MgSO_4$, 5 mM KCl and 1 M NaCl. The slides were then washed in HBS-C (25 mM Hepes, pH 7.2, 150 NaCl, 3 mM $CaCl_2$, 3 mM $MgSO_4$, 5 mM KCl, Complete protease inhibitor cocktail) containing 32 mM sucrose and the non-specific binding sites were blocked for 20 minutes in HBS-C containing 3% BSA, 1.5% normal goat serum and 32 mM sucrose. The binding sites were avidin and biotin were blocked using the avidin/biotin blocking kit from Vector (Burlingame, Calif.). The slides were incubated for 1 hour in HBS-C/3% BSA and 1 nM of WISP-1-Fc, washed three times for 1 minute each time with cold (4° C.) HBS-C/1% BSA and fixed for 10 minutes in PBS/4% paraformaldehyde. The slides were incubated with 0.2 microgram/ml biotinylated goat anti-human IgG, Fc specific in HBS-C/3% BSA for 30 minutes, washed and fixed in PBS/4% paraformaldehyde for 10 minutes. The signal was amplified using the TSA indirect amplification kit according to the manufacturer instructions. The reaction was stopped by three washes of 4 minutes in TBS/0.1% BSA. The slides were incubated for 30 minutes with streptavidin conjugated FITC (1:1000) in TBS/0.1% BSA and washed in TBS containing 0.05% Tween-20. The sections were mounted using Vectashield mounting media containing 1 microgram/ml Hoechst 33342 and visualized under a Nikon Eclipse 800 Fluorescent microscope.

Figure 1D:
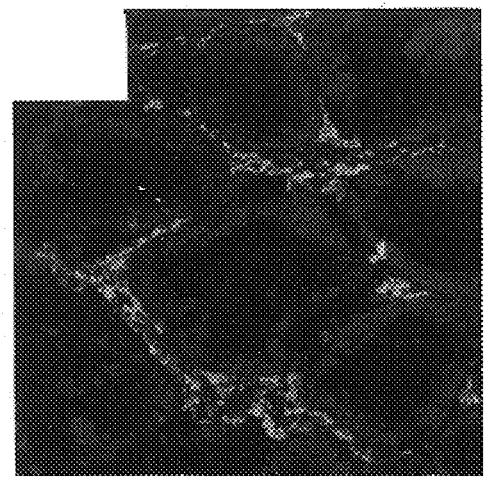
Figure 1E:
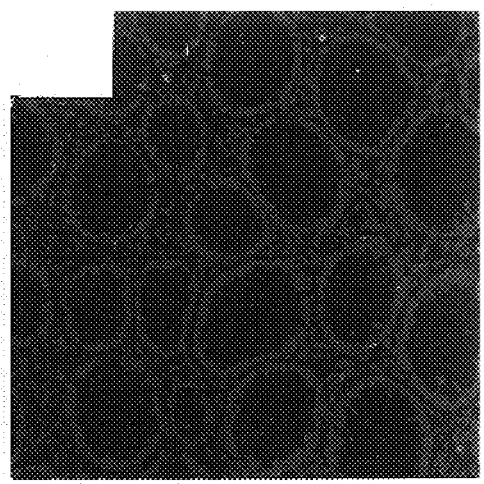
Figure 1F:
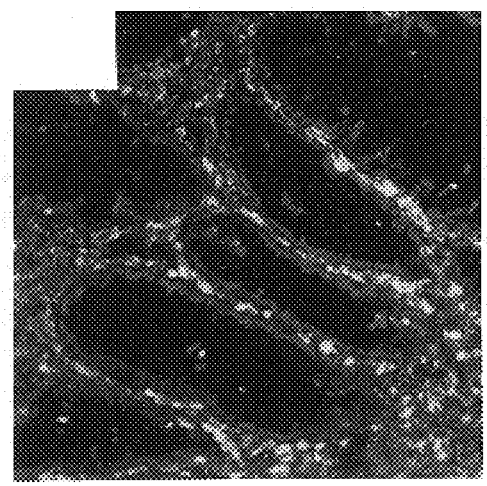
Figure 1G:
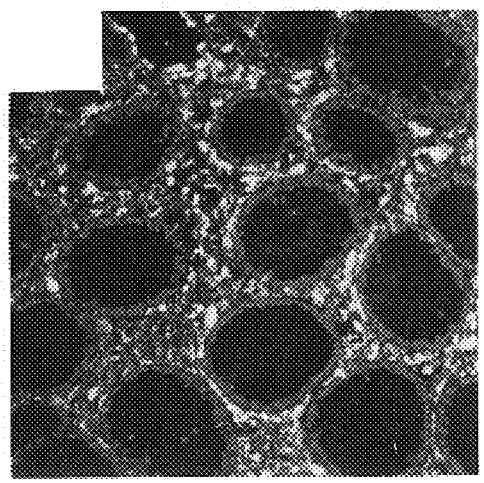

Although vimentin staining revealed the presence of mesenchymal cells in both the tumor and the normal mucosa (see FIGS. 1F and 1G), the in situ WISP-1 binding was restricted to the peritumoral stroma (FIG. 1D). No binding was found to the tumor epithelial cells or to the normal mucosa (FIGS. 1D and 1E).

B. WISP-1 Binds to Human Skin Fibroblast Conditioned Media

Figure 2A:
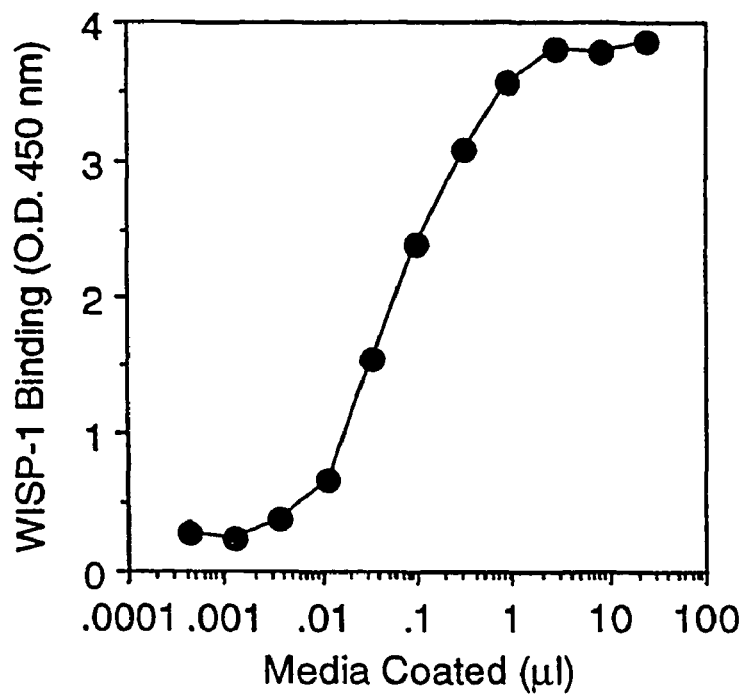
FIGS. 2A-2B show the binding of mWISP-1-IgG to human skin fibroblasts conditioned media. Serum free conditioned media of human skin fibroblasts was prepared as described in the section "Purification of WISP-1 Binding Factors". Fifty microliters of conditioned media was coated in duplicate in microtitration wells. The non-specific binding sites were saturated by incubation with HBS-C containing 3% BSA and the wells were incubated for 2 hours with mWISP-1-IgG. The wells were washed and incubated for 1 hour with horseradish peroxidase conjugated anti-human IgG Fc'. After 6 washes with HBS-C containing 0.3% BSA, the signal was visualized using a horseradish peroxidase chromogenic substrate. The reaction was stopped with 1 M phosphoric acid and the OD at 450 nm was measured. 2A shows binding of 1 nM of mWISP-1-IgG to wells coated with serial dilutions of conditioned media; 2B shows binding of serial dilutions of mWISP-1-IgG to wells coated with 0.5 µl of human skin fibroblast conditioned media.
Figure 2B:
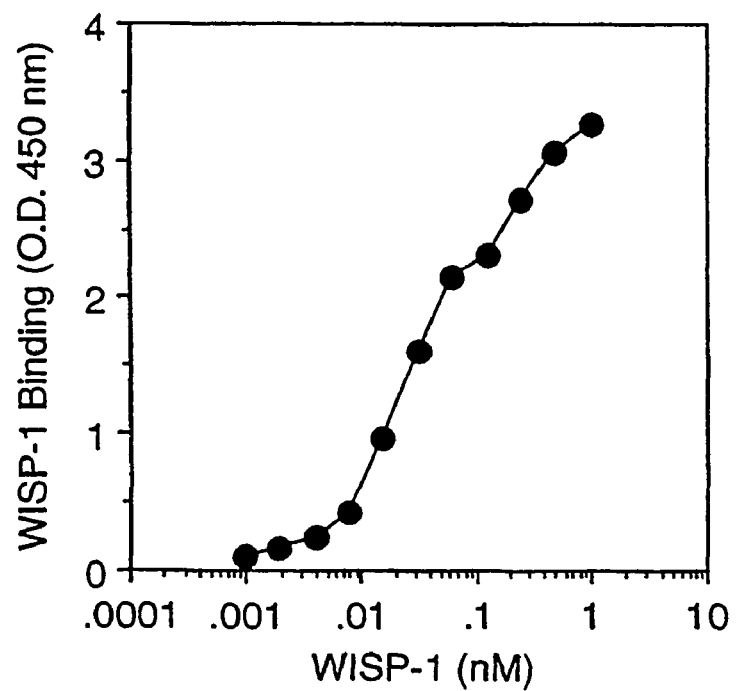

To examine whether a WISP-1 binding factor was secreted or shed from the surface of human skin fibroblasts, a solid phase binding assay was conducted. Serum free conditioned media from human skin fibroblasts (prepared as described above) was collected, concentrated and coated in microtiter plates overnight. Fifty microliters of conditioned media was coated in duplicate in microtitration wells. The non-specific binding sites were saturated by incubation with HBS-C containing 3% BSA and the wells were incubated for 2 hours with mWISP-1-IgG. After blocking the non-specific binding sites, the wells were first incubated with WISP-1 and then with a horseradish peroxidase conjugated anti-human IgG antibody. The wells were washed and incubated for 1 hour with horseradish peroxidase conjugated anti-human IgG Fc'. After 6 washes with HBS-C containing 0.3% BSA, the signal was visualized using a horseradish peroxidase chromogenic substrate. The reaction was stopped with 1 M phosphoric acid and the OD at 450 nm was measured. FIG. 2A shows binding of 1 nM of mWISP-1-IgG to wells coated with serial dilutions of conditioned media, and FIG. 2B shows binding of serial dilutions of mWISP-1-IgG to wells coated with 0.5 µl of human skin fibroblast conditioned media. Binding was proportional to the amount of media coated and the concentration of WISP-1 added, indicating that human skin fibroblasts produce soluble WISP-1 binding factors.

Figures 3A, 3B:
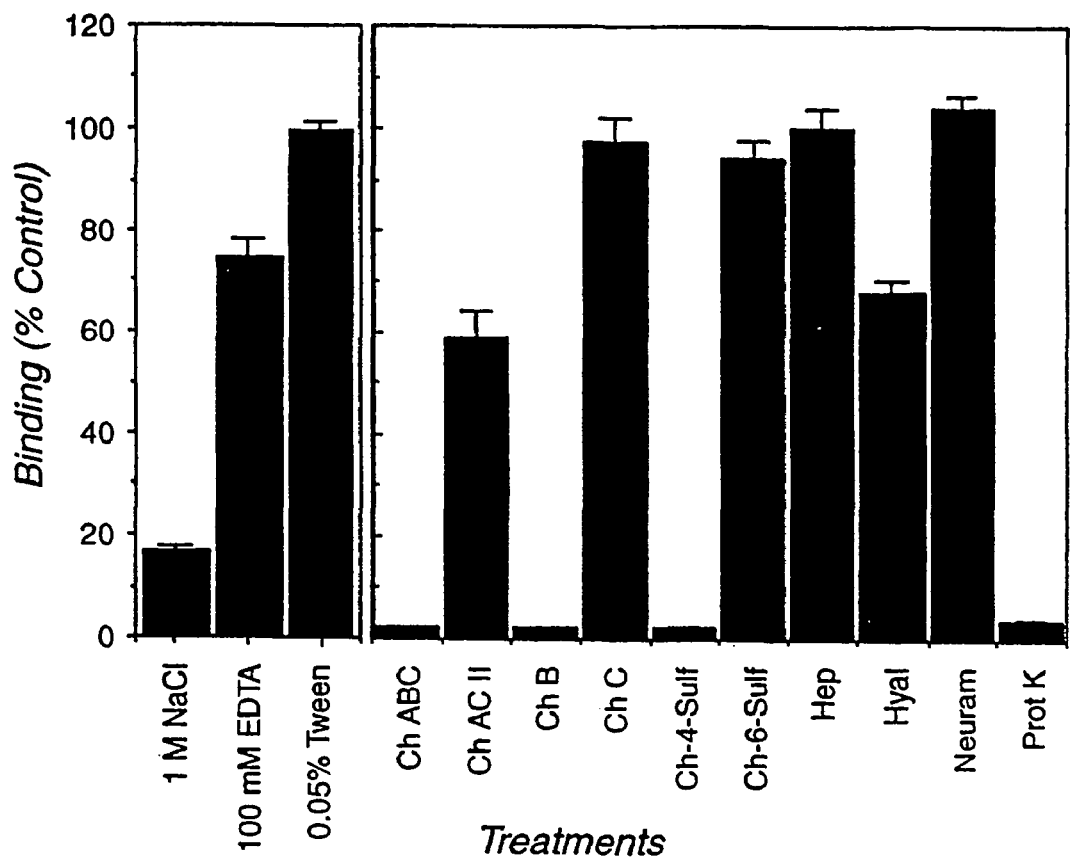
FIGS. 3A-3B show the binding of mWISP-1-IgG to a chondroitinase B sensitive factor of human skin fibroblast conditioned media. In 3A, fifty microliters of conditioned media was coated in duplicate in microtitration wells and the non-specific binding sites were saturated by incubation with HBS-C containing 3% BSA. One nanomolar WISP-1-IgG was incubated for 2 hours in the absence or the presence of 1 M NaCl, 100 mM EDTA or 0.05% Tween-20. The wells were washed and incubated for 1 hour with horseradish peroxidase conjugated anti-human IgG Fc'. After 6 washes with HBS-C containing 0.3% BSA, the signal was visualized using a horseradish peroxidase chromogenic substrate. The reaction was stopped with 1 M phosphoric acid and the OD at 450 nm was measured. In 3B, 50 µl of HBS-C containing 0.5 U/ml chondroitinase ABC (Ch ABC), 0.5 U/ml chondroitinase AC II (Ch AC II), 0.5 U/ml chondroitinase B (Ch B), 0.5 U/ml chondroitinase C (Ch C), 0.5 U/ml chondroitin-4-sulfatase (Ch-4-Sulf), 0.5 U/ml chondroitin-6-sulfatase (Ch-6-Sulf), 0.5 U/ml heparinase (Hep), 0.5 U/ml hyaluronidase (Hyal), 0.5 U/ml neuramimidase (Neuram) or 100 µg/ml proteinase K (Prot K) were added to the coated wells and incubated for 2 hours at 37° C. The wells were washed extensively, the non specific binding sites were saturated and 1 nM mWISP-1-IgG was incubated for 2 hours at room temperature. The wells were washed and binding of WISP-1-IgG was measured.

As seen in FIG. 3A, the interaction between WISP-1 and the conditioned media was abolished in the presence of 1 M NaCl. The presence of 100 mM EDTA only partially diminished the binding while the presence of 0.05% Tween-20 had no effect. It was concluded that the binding of WISP-1 to the coated material was cation independent and had an ionic component. The possibility that the binding factor was a proteoglycan was then investigated by treating the coated wells with various lyases before the binding of WISP-1 was evaluated. Treatment of the coated material with chondroitinase C, chondroitin-6-sulfatase, heparinase or neuramimidase did not alter the binding of WISP-1 when compared to the control (FIG. 3B). However, the digestion with chondroitinase AC II or hyaluronidase partially diminished the binding. Ultimately, the treatment with chondroitinase ABC, chondroitinase B, chondroitin-4-sulfatase or proteinase K abolished the binding of WISP-1 to the coated wells. The specificity of chondroitinase B and chondroitin-4-sulfatase indicates that dermatan sulfate components are essential to the binding of WISP-1. Moreover, the sensitivity of the interaction to a proteinase K indicates that the binding factor has a proteinous component. The results suggest that WISP-1 binds to a secreted dermatan sulfate containing proteoglycan.

Chondroitinase ABC and chondroitinase B treatments completely abolished the binding, whereas treatment with chondroitinase C had no effect. Chondroitinase B cleaves dermatan sulfate at the beta-D-galactosamine-L-iduronic acid linkage. The specificity of this enzyme demonstrates the requirement for iduronic acid for the binding of WISP-1. Treatments with chondroitinase AC II or hyaluronidase only partially reduced the binding. This could indicate that the glycosaminoglycan chain responsible for the interaction of WISP-1 consisted of a dermatan sulfate-chondroitin sulfate co-polymer. By cleaving the susceptible galactosaminidic bonds, those enzymes could have removed parts of the glycosaminoglycan chain containing iduronic acid residues. Treatment with chondroitin-4-sulfatase completely abolished the binding while chondroitin-6-sulfatase did not alter the interaction. This indicates the necessity for a sulfate group at position 4 of the N-acetylgalactosamine for the interaction. Treatment with heparinase had no effect, indicating that the binding does not require the iduronic acid to be sulfated at position 2. Treatment with proteinase K abolished the binding suggesting that the glycosaminoglycan responsible for the interaction is linked to a protein core that could be detached from the wells by proteolytic degradation. Collectively, these results support the conclusion that a iduronic acid containing motif of the glycosaminoglycan chain of a proteoglycan mediates WISP-1 binding to human skin fibroblast conditioned media.

C. Purification and Identification of the WISP-1 Binding Factor

Figures 4A, 4B:
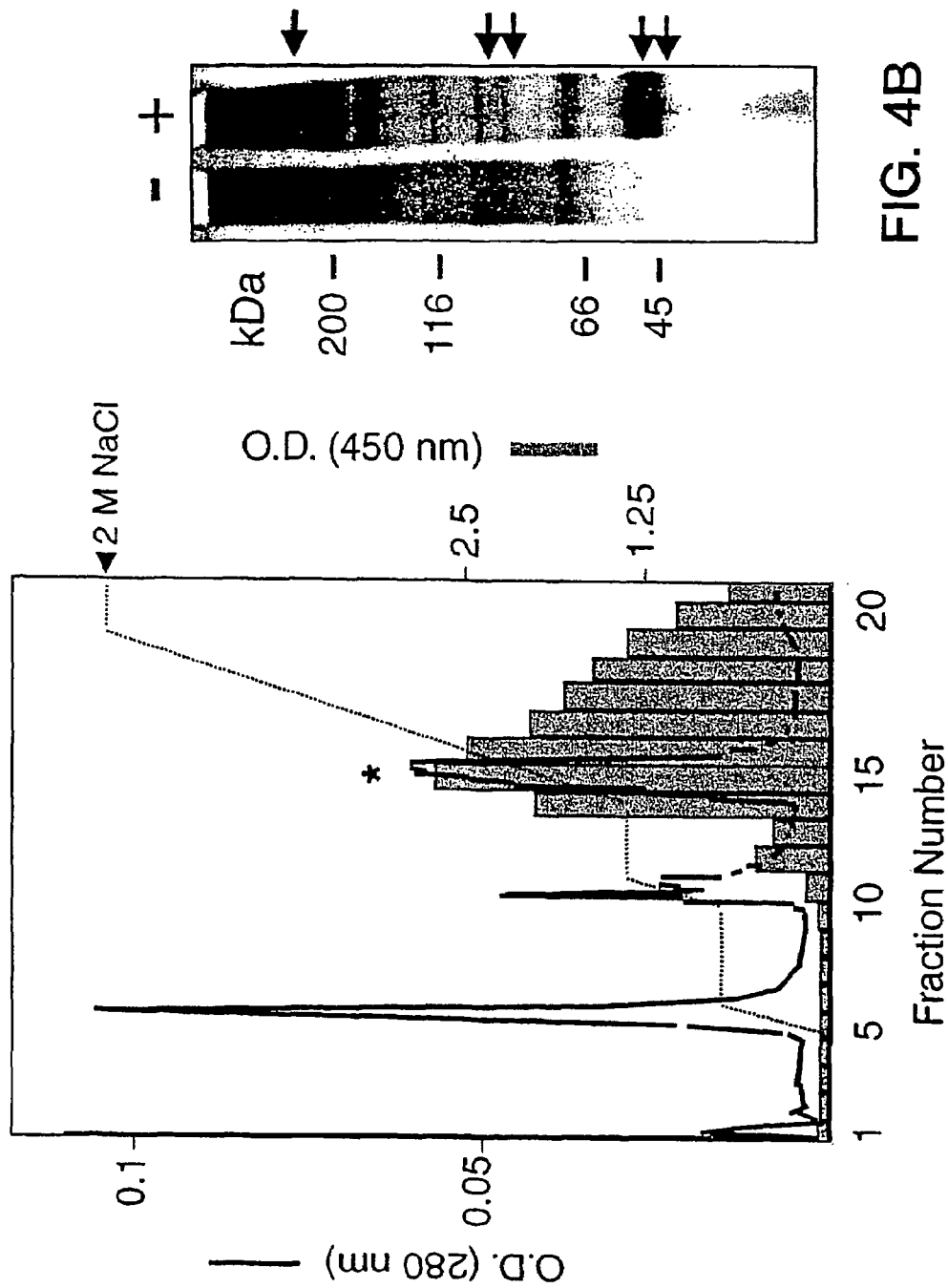
FIGS. 4A-4B show purification of WISP-1 binding factors from human skin fibroblast conditioned media. In 4A, the serum free conditioned media from human skin fibroblasts was collected after three days of culture, concentrated, transferred to a buffer containing 20 mM Tris-HCl pH 7.4 and 300 mM NaCl, and applied on a Q-Sepharose anion exchange chromatography column. The column was washed and the retained proteins were desorbed with an increasing concentration of NaCl. The presence of a WISP-1 binding factor was analyzed in each fraction using a solid phase binding assay. In 4B, fraction 15 (indicated by a * in FIG. 4A) was incubated at 37° C. for 2 hours in the presence (+) or the absence (−) of 0.1 U of chondroitinase ABC. The samples were separated by SDS-PAGE under reducing conditions and the gels were silver stained. The indicated bands were identified by mass spectroscopy.

To purify the factor responsible for the binding of WISP-1, the serum free conditioned media from human skin fibroblasts was collected after three days of culture, concentrated, transferred to a buffer containing 20 mM Tris-HCl pH 7.4 300 mM NaCl and applied on a Q-Sepharose anion exchange chromatography column. The column was washed and the retained proteins were desorbed with an increasing concentration of NaCl. The presence of a WISP-1 binding factor was analyzed in each fraction using a solid phase binding assay, and the results are shown in FIG. 4A. Further, fraction 15 (indicated by a * in FIG. 4A) was incubated at 37° C. for 2 hours in the presence (+) or the absence (−) of 0.1 U of chondroitinase ABC. The samples were separated by SDS-PAGE under reducing conditions and the gels were silver stained. The indicated bands were identified by mass spectroscopy (FIG. 4B).

The bands found at 46, 60, and 70 kDa corresponded to decorin while the band at 44 kDa was identified as biglycan (the band at 230 kDa appeared to be a mixture of both decorin and biglycan). The bands found at the different molecular weights probably corresponded to biglycan and decorin containing incompletely digested glycosaminoglycan chains that were generated during the chondroitinase ABC treatment. The results demonstrate that WISP-1 binds to the two dermatan sulfates containing proteoglycans, biglycan and decorin.

D. WISP-1 Binds to Decorin and Biglycan

To demonstrate the direct interaction of WISP-1 with decorin and biglycan, a solid phase binding assay was conducted. Decorin and biglycan were coated to microtiter wells overnight. Non-specific binding sites were saturated and 0.25 nM of mWISP-1-IgG was incubated for 2 hours. The wells were washed and incubated with horseradish peroxidase conjugated anti-human IgG Fc' (2 μg/ml) for 1 hour. After 6 washes with PBS containing 0.05% Tween-20, a signal was developed by the incubation of a chromogenic substrate. The color development was stopped by the addition of 1 M phosphoric acid and the O.D. at 450 nm was measured.

Figure 5A:
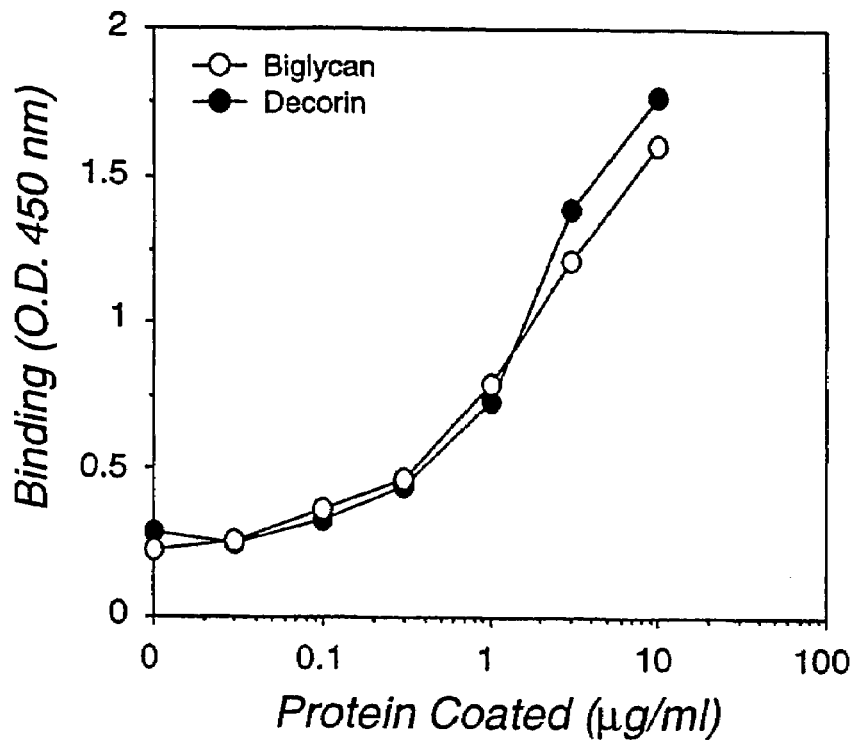
FIGS. 5A-5B show WISP-1 binding to decorin and biglycan. In 5A, microtiter wells were coated with serial dilutions of decorin (filled circles) or biglycan (empty circles). Non-specific binding sites were saturated and 0.25 nM of mWISP-1-IgG was incubated for 2 hours. The wells were washed and incubated with horseradish peroxidase conjugated anti-human IgG Fc' (2 µg/ml) for 1 hour. After 6 washes with PBS containing 0.05% Tween-20, a signal was developed by the incubation of a chromogenic substrate. The color development was stopped by the addition of 1 M phosphoric acid and the O.D. at 450 nm was measured. In 5B, fifty milliliters of human skin fibroblast conditioned media were coated in wells of microtiter plates. Non-specific binding sites were saturated and 0.25 nM of WISP-1-IgG was incubated in the presence of various concentrations of decorin (filled circles) or biglycan (empty circles) for 2 hours. The binding of mWISP-1-IgG was evaluated as described in 5A.

As illustrated in FIG. 5A, the curves corresponding to the binding of WISP-1 to decorin and biglycan are very similar and are proportional to the amount of protein coated. Similarly, the ability of decorin and biglycan to inhibit the binding of WISP-1 to coated human skin fibroblast conditioned media was evaluated.

Figure 5B:
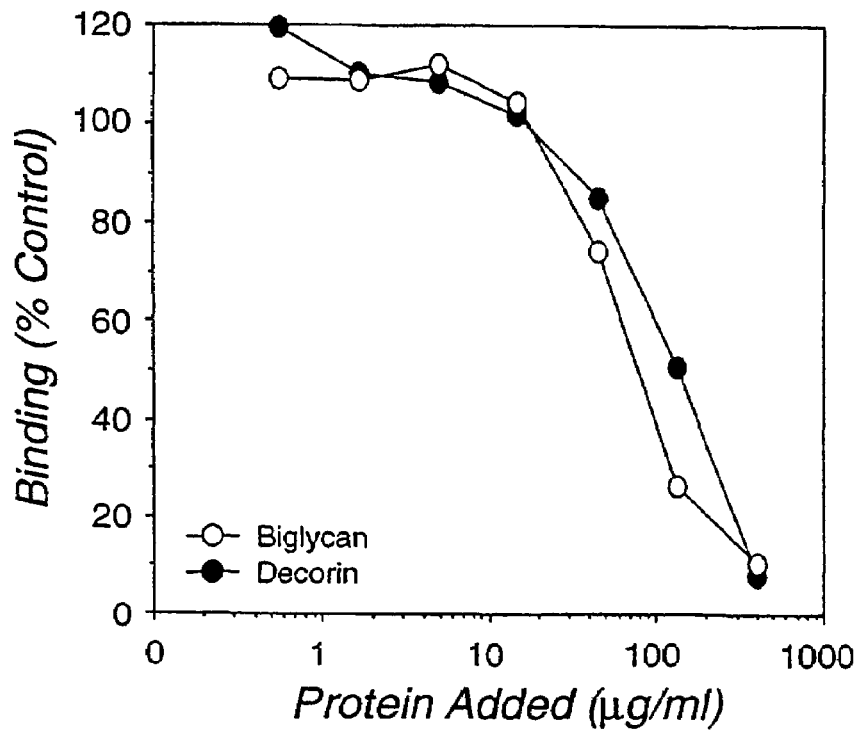

Fifty microliters of human skin fibroblast conditioned media were coated in wells of microtiter plates. Non-specific binding sites were saturated and 0.25 nM of WISP-1-IgG was incubated in the presence of various concentrations of decorin (filled circles) or biglycan (empty circles) (FIG. 5B) for 2 hours. The binding of mWISP-1-IgG was evaluated as described above. As seen in FIG. 5B, the binding of WISP-1 to the human skin fibroblast conditioned media is gradually decreased in the presence of increasing concentrations of decorin and biglycan. Decorin and biglycan gave similar competition curves showing 50% inhibition of the WISP-1 binding at 70 μg/ml for decorin and 105 μg/ml for biglycan.

E. WISP-1 binds to Glycosaminoglycan

Figure 6:
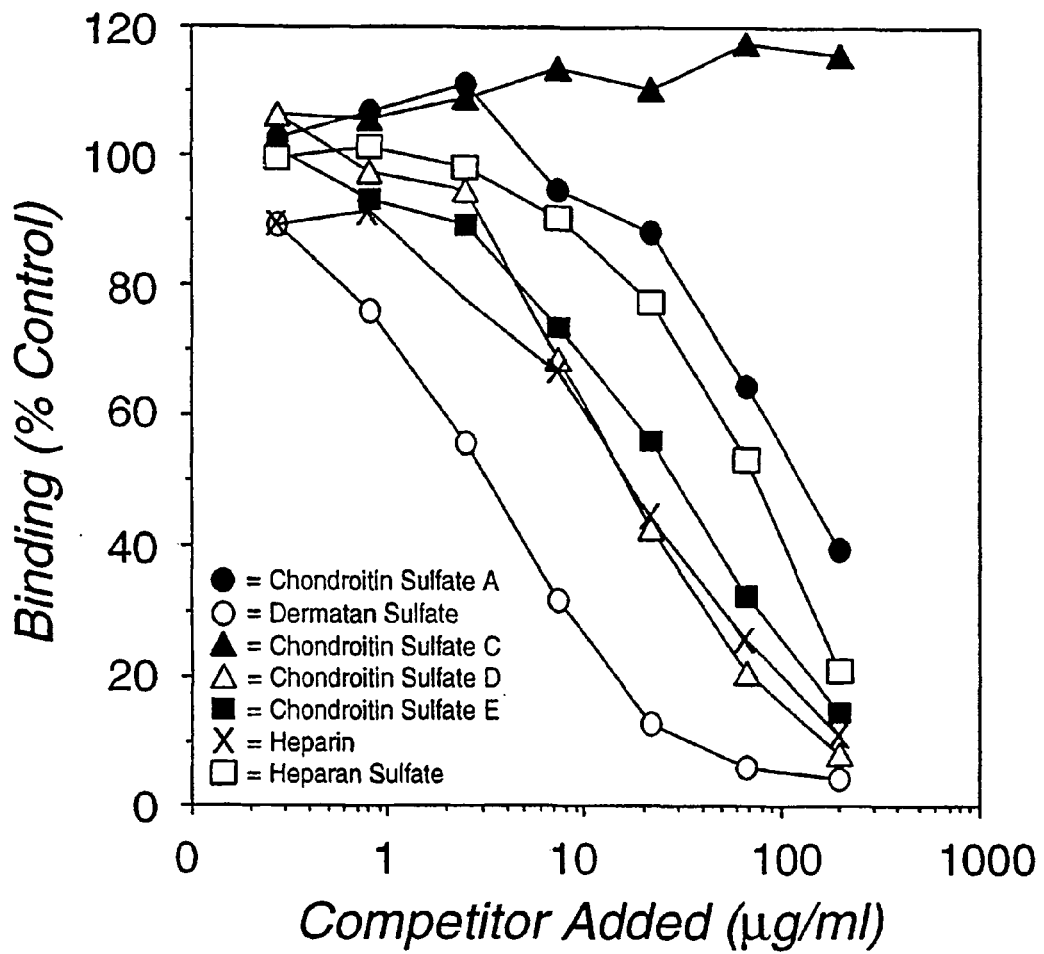
FIG. 6 shows mWISP-1-IgG binding to glycosaminoglycans. Serum free conditioned media of human skin fibroblasts was prepared as described below in the Examples. Fifty µl of conditioned media were coated in wells of microplates overnight at 4° C., the non specific binding sites were saturated and the wells were incubated for 2 hours at room temperature with 0.5 nM of WISP-1-IgG in the presence of various concentrations of different glycosaminoglycans. The wells were washed, a signal was developed using a chromogenic substrate and the O.D. at 450 nm was measured. Chondroitin sulfate A (filled circles); dermatan sulfate (empty circles); chondroitin sulfate C (filled triangles); chondroitin sulfate D (empty triangles); chondroitin sulfate E (filled squares); heparin (X); heparan sulfate (empty squares).
Figure 7A:
FIGS. 7A-7I show that WISP-1 binding to human skin fibroblasts is competed by dermatan sulfate. Human skin fibroblasts were seeded in chamber slides. The non specific binding sites were saturated and 1 nM WISP-1-IgG was incubated for 1 hour at room temperature in the absence (7A) or the presence (7B) of 50 µg/ml chondroitin sulfate A ("CSA"), dermatan sulfate ("DS"); (7C), chondroitin sulfate C ("CS C"); (7D), chondroitin sulfate D ("CS D"); (7E), chondroitin sulfate E ("CS E") (7F); heparin ("Hep") (7G) or heparan sulfate ("HS") (7H). The cells were washed and fixed and the binding of WISP-1-IgG was detected by immunofluorescence using a biotinylated anti-human IgG antibody and the indirect tyramide substrate amplification procedure ended with FITC conjugated streptavidin. The relative fluorescence intensity of acquired digital images was measured by morphometric analysis (7I).
Figure 7B:

To understand if the specificity of the interaction of WISP-1 to the proteoglycan is limited to dermatan sulfate, the binding of WISP-1 to the human skin fibroblast conditioned media in the presence of various proteoglycans was evaluated. Serum free conditioned media of human skin fibroblasts was prepared as described above. Fifty μl of conditioned media were coated in wells of microplates overnight at 4° C., the non specific binding sites were saturated and the wells were incubated for 2 hours at room temperature with 0.5 nM of WISP-1-IgG in the presence of various concentrations of different glycosaminoglycans. The wells were washed, a signal was developed using a chromogenic substrate and the O.D. at 450 nm was measured. FIG. 6 shows: Chondroitin sulfate A (filled circles); dermatan sulfate (empty circles); chondroitin sulfate C (filled triangles); chondroitin sulfate D (empty triangles); chondroitin sulfate E (filled squares); heparin (X); heparan sulfate (empty squares).

As shown in FIG. 6, the binding of WISP-1 is reduced proportionally in the presence of increasing concentrations of various proteoglycans. The binding of WISP-1 reached 50% of the maximal binding at 3 μg/ml of dermatan sulfate, 10.5 μg/ml chondroitin sulfate D or heparin, 30 μg/ml chondroitin sulfate E, 75 μg/ml of heparan sulfate, 105 μg/ml chondroitin sulfate A. The presence of chondroitin sulfate C did not reduce the binding of WISP-1. This data demonstrate that the interaction of WISP-1 with glycosaminoglycan is sufficient to mediate its binding to human skin fibroblasts conditioned media. Moreover it indicates that WISP-1 shows a greater specificity for dermatan sulfate than any other glycosaminoglycan tested.

F. Binding of WISP-1 to Human Skin Fibroblasts is Inhibited by Dermatan Sulfate

Figure 7C:
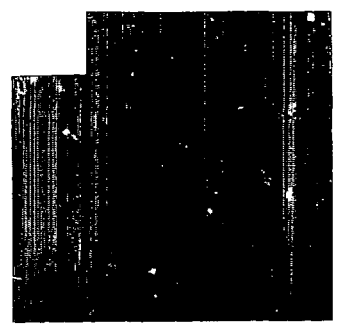
Figure 7D:
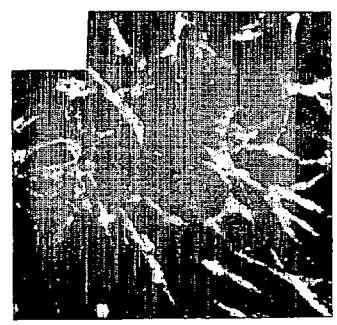
Figure 7E:
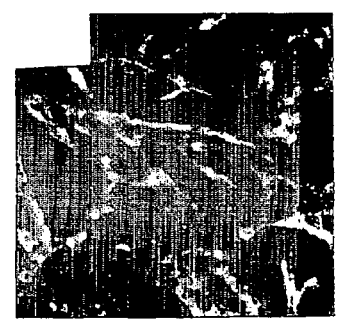
Figure 7F:
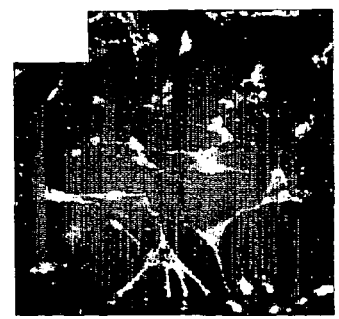
Figure 7G:
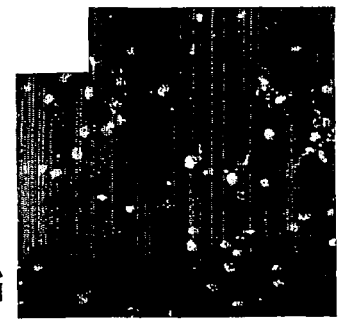
Figure 7H:
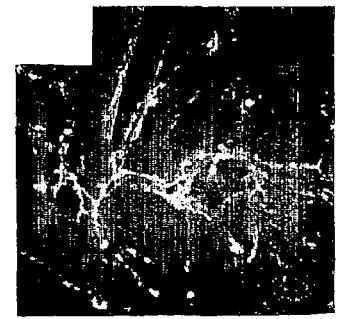

To ascertain the importance of dermatan sulfate containing proteoglycans in the binding of WISP-1 to the cell surface a cell binding analysis in the presence of various glycoaminoglycans was performed. Human skin fibroblasts were seeded in chamber slides. The non specific binding sites were saturated and 1 nM WISP-1-IgG was incubated for 1 hour at room temperature in the absence (FIG. 7A) or the presence of 50 μg/ml chondroitin sulfate A (FIG. 7B), dermatan sulfate (FIG. 7C), chondroitin sulfate C (FIG. 7D), chondroitin sulfate D (FIG. 7E), chondroitin sulfate E (FIG. 7F), heparin (FIG. 7G) or heparan sulfate (FIG. 7H). The cells were washed and fixed and the binding of WISP-1-IgG was detected by immunofluorescence using a biotinylated anti-human IgG antibody and the indirect tyramide substrate amplification procedure ended with FITC conjugated streptavidin.

Figure 7I:
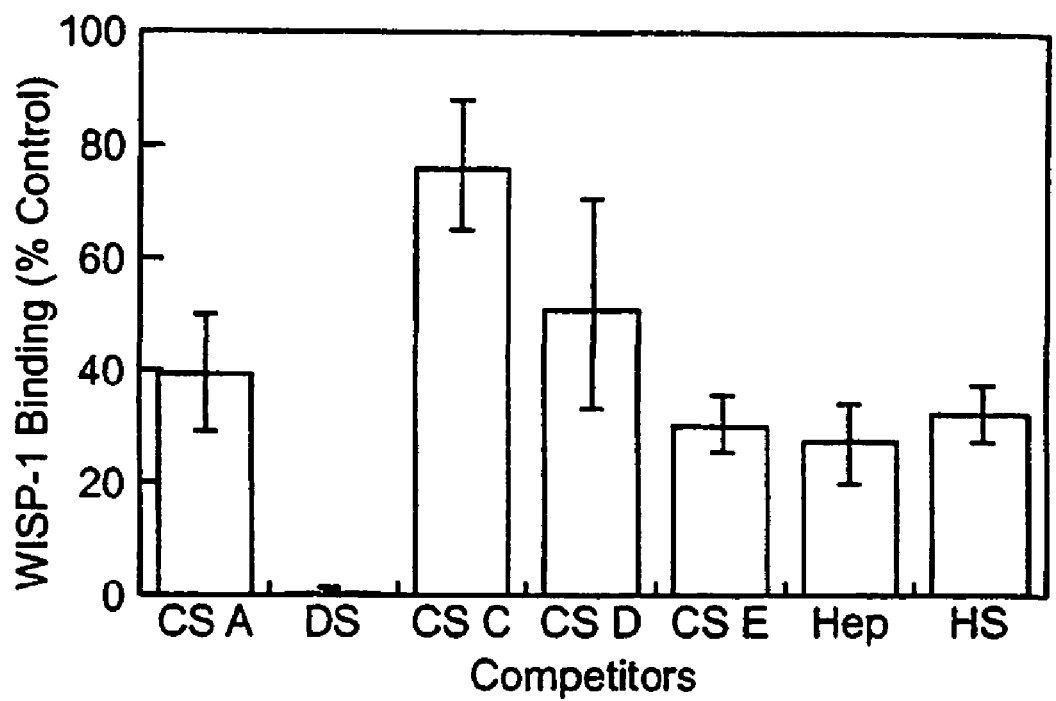

In the absence of any added glycosaminoglycan the binding of WISP-1 to the cell surface gave rise to a strong fluorescent staining. Chondroitin sulfate C and chondroitin sulfate D reduced WISP-1 binding by approximately 20% and 46%, respectively, while chondroitin sulfate A, chondroitin sulfate E, heparin sulfate or heparin diminished the interaction by approximately 60-70% (FIG. 7I). On the other hand, in the presence of 50 μg/ml of dermatan sulfate, the binding of WISP-1 to the surface of human skin fibroblasts was abolished. Together these results demonstrate that WISP-1 has a higher affinity for dermatan sulfate and this interaction may be responsible for the binding of WISP-1 to the cell surface.

G. WISP-1 Binding to Human Skin Fibroblasts is Abolished by the Digestion of the Cell Surface with Chondroitinase B While WISP-1 interacts with glycosaminoglycans and small proteoglycans containing dermatan sulfate, whether it interacts with the cell surface through the same type of interaction remained to be determined. To address this possibility, the binding of WISP-1 to the surface of human skin fibroblasts treated with different glycosaminoglycan lyases was analyzed. Human skin fibroblasts were incubated for 2 hours at 37° C. in the absence (FIG. 8A), or the presence of with 0.1 U of chondroitinase ABC (FIG. 8B), chondroitinase B (FIG. 8C), chondroitinase C (FIG. 8D), heparinase (FIG. 8E), or in the absence of mWISP-1 (FIG. 8F). The cells were washed, the non specific binding sites were saturated and 1 nM mWISP-1-IgG was incubated for 1 hour at room temperature. After 3 washes, the cells were fixed and the binding of mWISP-1-IgG was detected by immunofluorescence using a biotinylated anti-human IgG antibody and the indirect tyramide substrate amplification procedure ended with FITC conjugated streptavidin.

Figure 8A:
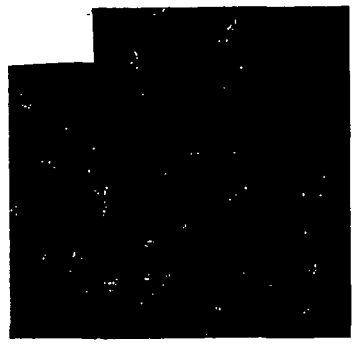
FIGS. 8A-8G show that WISP-1 binding to human skin fibroblasts is abolished by the digestion of the cell surface with chondroitinase B. Human skin fibroblasts were incubated for 2 hours at 37° C. in the absence (8A), or the presence of 0.1 U of chondroitinase ABC (Ch ABC); (8B), chondroitinase B ("Ch B"); (8C), chondroitinase C ("Ch C"); (8D), heparinase ("Hep") (8E). The cells were washed, the non specific binding sites were saturated and 1 nM WISP-1-IgG was incubated for 1 hour at room temperature. After 3 washes, the cells were fixed and the binding of WISP-1-IgG was detected by immunofluorescence using a biotinylated anti-human IgG antibody and the indirect tyramide substrate amplification procedure ended with FITC conjugated streptavidin.
Figure 8B:
Figure 8C:
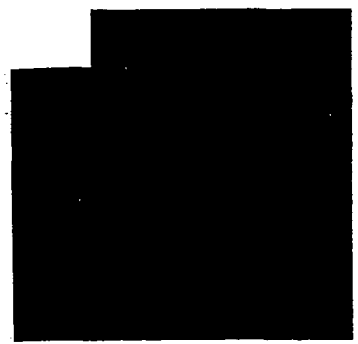
Figure 8D:
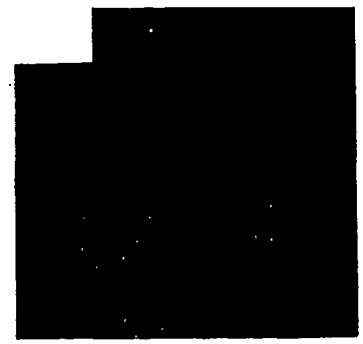
Figure 8E:
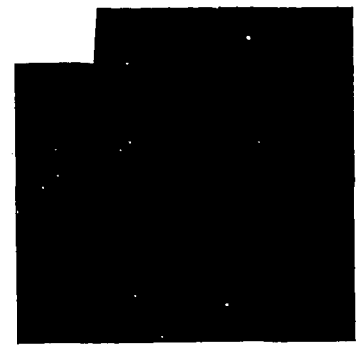
Figure 8F:
Figure 8G:
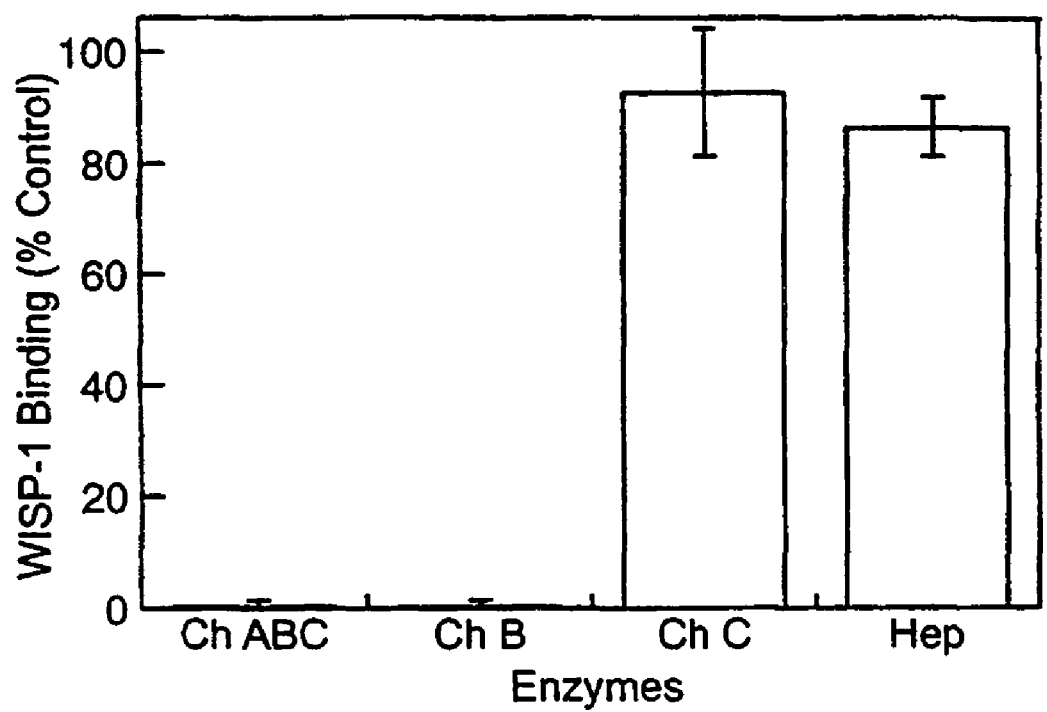

As shown in FIG. 8A, the binding of WISP-1 to the surface of untreated human skin fibroblasts gave rise to a strong fluorescent signal. When the cells were treated with chondroitinase ABC or chondroitinase B the binding of WISP-1 was decreased to a level comparable to the negative control in which WISP-1 was omitted (FIGS. 8B, C and D respectively).

On the other hand, the binding of WISP-1 to the cells treated with chondroitinase C or heparinase did not show any modification in term of distribution or intensity (FIG. 8, panel D and E respectively). These results indicated that the binding of WISP-1 to the cell surface of human skin fibroblasts is mediated by a dermatan sulfate containing proteoglycan.

H. Decorin and Biglycan Block the Binding of WISP-1 Human Skin Fibroblasts

Figure 9A:
FIGS. 9A-9D show that WISP-1 binding to human skin fibroblasts is competed by decorin and biglycan. Human skin fibroblasts were seeded in chamber slides and the non specific binding sites were saturated. One nanomolar mWISP-1-IgG was incubated for 1 hour at room temperature in the presence of 1 mg/ml decorin (9A) or biglycan (9B), or in the absence of added competitors (9C). The cells were washed and fixed and the binding of WISP-1-IgG was detected by immunofluorescence using a biotinylated anti-human IgG antibody and the indirect tyramide substrate amplification procedure ended with FITC conjugated streptavidin. The relative fluorescence intensity of acquired digital images was measured by morphometric analysis (9D).
Figure 9B:
Figure 9C:
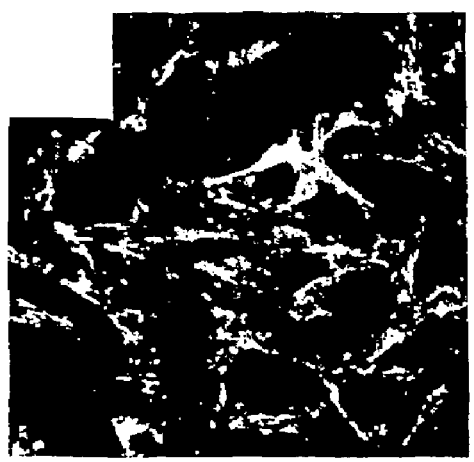
Figure 9D:
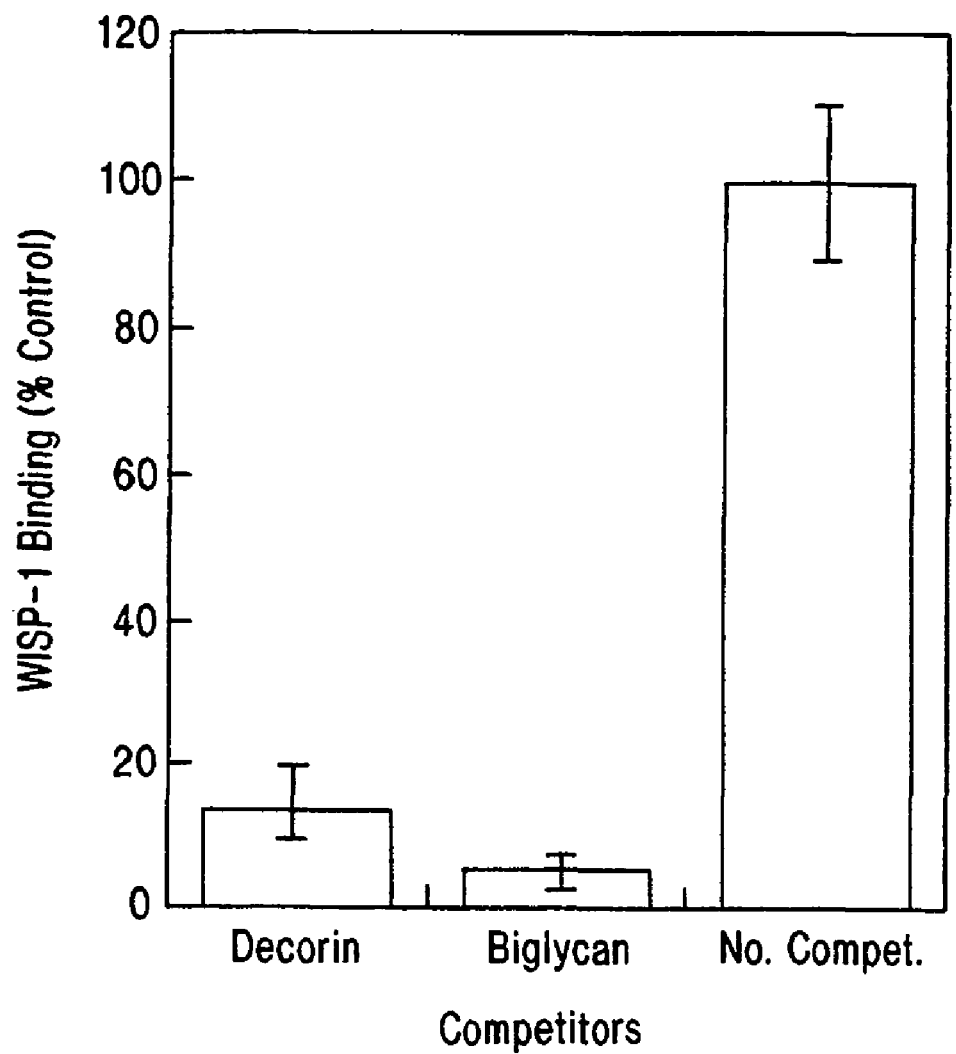

The binding of WISP-1 to human skin fibroblasts was evaluated in the presence or the absence of an excess of decorin or biglycan. Human skin fibroblasts were seeded in chamber slides and the non specific binding sites were saturated. One nanomolar mWISP-1-IgG was incubated for 1 hour at room temperature in the presence of 1 mg/ml decorin (FIG. 9A), biglycan (FIG. 9B), or in the absence of added competitors (FIG. 9C). The cells were washed and fixed, and the binding of WISP-1-IgG was detected by immunofluorescence using a biotinylated anti-human IgG antibody and the indirect tyramide substrate amplification procedure ended with FITC conjugated streptavidin.

As shown in FIG. 9, the presence of decorin or biglycan partially blocked the interaction of WISP-1 with human skin fibroblasts. Although the inhibition is significant (approximately 88% and 94%), even at the highest concentration tested (1 mg/ml) the binding could not be completely abolished. This can be explained by the capacity that decorin and biglycan have to interact with collagen present in the extracellular matrix of the cell.

Decorin and biglycan are members of a family of small leucine-rich proteoglycans present in the extracellular matrix of connective tissues. The secreted form of decorin consists of a core protein of 36,319 Da (Krusius et al., *Proc. Natl. Acad. Sci.*, 83:7683-7687 (1986)) and a single glycosaminoglycan chain of dermatan sulfate attached to a serine at position 4 (Scott, PG, *Dermatan Sulfate Proteoglycans: Chemistry, Biology, Chemical Pathology*, Portoland Press, London, England, 1993). The secreted form of biglycan consists of a core protein of 37,983 Da substituted with two glycosaminoglycan chains, one of dermatan sulfate and one of chondroitin sulfate (Fisher et al., *J. Biol. Chem.*, 264:4571-4576 (1989)). The core proteins of biglycan and decorin share about 55% amino acid identity. The molecular weight of the core protein of decorin and biglycan corresponds to the predicted molecular weight of the two bands referred to above having the fastest electrophoretic mobility after the chondroitinase ABC treatment. The slower migrating bands would correspond to decorin and biglycan bearing partially digested glycosaminoglycan chains.

Decorin co-localizes with fibronectin fibrils at the surface of human skin fibroblasts (Schmidt, G., Robenek, H., Harrach, B., Glossl, J., Nolte, V., Hormann, H., Richter, H. and Kresse, H., *J. Cell. Biol,* 104:1683-1691 (1987)). It is possible that the WISP-1 interaction with the cell surface is mediated by decorin attached to the extracellular matrix. Using immunofluorescence, the presence of decorin at the surface of the human skin fibroblasts was confirmed in the above assays. Also, it was shown that decorin and biglycan significantly diminished WISP-1 binding to the cell surface. The interaction of decorin and biglycan with human skin fibroblasts probably prevented the complete inhibition of WISP-1 binding Together those results demonstrated that decorin can act as a cell surface binding site for WISP-1.

Several proteoglycans associated with the cellular membrane or the extracellular matrix were shown to contain iduronic acid. Consequently, it is possible for WISP-1 to interact with chondroitin sulfate of heparan sulfate proteoglycan exhibiting iduronate motifs. Also, the iduronic acid content of the glycosaminoglycan chain of different proteoglycans was shown to vary with their tissue distribution. For example, decorin and biglycan from skin contain approximately 80% of iduronic acid whereas in cartilage they contain only 40% (Choi et al., *J. Biol. Chem.*, 264:2876-2884 (1989)). The glycosaminoglycan chains of biglycan and decorin from bone and bovine nasal cartilage contain no iduronate and are therefore chondroitin sulfate (Fisher et al., *J. Biol. Chem.* 262: 9702-9708 (1987); Heinegard et al., *Biochem. J.*, 3:2042-2051 (1981)). Also, it was reported that TGF-β treatment induces a 10 to 15% decrease of the iduronic acid content of side-chains of decorin and biglycan (Malmstrom, A et al., *Dermatan Sulfate Proteoglycans: Chemistry, Biology, Chemical Pathology*, Portoland Press, London, England, 1993). Consequently, it is possible that modification in the level of iduronic acid content in the glycosaminoglycan chain of proteoglycans modulates the interaction of WISP-1.

Biglycan and decorin are known to interact with a variety of extracellular matrix proteins, cytokines and cell surface receptors (for a review, see Hocking et al., *Matrix Biol.*, 17:1-19 (1998) and Iozzo, R. V. *J. Biol. Chem.* 274:18843-18846 (1999). Decorin and biglycan interact with transforming growth factor-β (TGF-β), negatively regulating its biological activity (Hildebrand et al., *Biochem. J.*, 302:527-534 (1994)). Also, decorin was shown to decrease mRNA levels and TGF-β protein synthesis in vitro (Stander et al., *Gene Therapy,* 5:1187-1194 (1998)). On the other hand, the expression of decorin is generally downregulated by TGF-β in various cells and organisms (Iozzo, *Ann. Rev. Biochem.*, 67:609-652 (1998)). The promoter region of the decorin gene contains a TGF-β-negative regulated element. This TGF-β-negative regulated element has been found in several protease genes downregulated by TGF-β and could function to suppress the decorin gene expression (Iozzo, *Experientia,* 49:447-455 (1993)). Moreover, the expression of decorin well correlates with a malignant property in human carcinoma (Adany et al., *J. Biol. Chem.*, 265:11389-11396 (1990); Hunzlemann et al., *J. Invest. Sermatol.*, 104:509-513 (1995)). It was found to be depressed in many tumoral tissues (Iozzo, supra, 1993) and lost in several tumor cell lines (Iozzo et al., *FASEB J.,* 10:598-614 (1996)). However, the expression of decorin is increased in the tumoral stroma (Adany et al., supra, 1991; Iozzo, supra, 1993, Brown et al., *Clin. Cancer Res.,* 5:1041-1056 (1999)). Decorin could be a potent negative regulator of the TGF-β released by the tumor to facilitate carcinogenesis and tumor progression. Since decorin was shown to directly suppress the growth of several carcinomas through TGF-β dependent and independent mechanisms, it was proposed that its expression in the peritumorous stroma may reflect a regional response of the host connective tissue cells to the invading neoplastic cells (Stander et al., supra, 1999).

Example 2

Adhesion of CHO Cells to WISP-1 and Other ECM Proteins

The following CHO cell lines (identified by ATCC number) were maintained in Ham-F12/LGDMEM (50:50) containing 10% FBS:

CHO-K1 (CCL-61)
CHO pgs A-745 (CRL-2242; DO NOT synthesize proteoglycan)

-continued

| | |
|---|---|
| CHO pgs B-618 | (CRL-2241; DO NOT synthesize proteoglycan) |
| CHO pgs D-677 | (CRL-2244; DO NOT synthesize haparan sulfate) |
| CHO pgs E-606 | (CRL-2246; Synthesize an undersulfated heparan sulfate) |

Maxisorp plates were coated with 50 µl of mWISP-1-IgG (5 µg/ml) or BSA 3% (Fraction V, fatty acid ultra-free; Boehringer Mannheim) in solution in PBS at 4° C. overnight. The next day, the contents of the wells were aspirated and the wells blocked with 200 µl of PBS/3% BSA for 1 hour at room temperature. The cells were taken up in PBS containing 2 mM EDTA, and the clumps were broken using a pipette and then centrifuged at 1000 rpm for 10 minutes. The supernatant was removed, and the cells were washed twice with serum free Ham-F12/LGDMEM (50:50) containing 1% BSA.

The cells were resuspended at $25 \times 10^5$ cells/ml in serum free Ham-F12/LGDMEM (50:50) containing 1% BSA. 50 µl of serum free Ham-F12/LGDMEM (50:50)/1% BSA was added to each well followed by 50 µl of cell suspension. The plates were incubated 2 hours at 37° C. without lid. Subsequently, the wells were washed 3× with PBS and once the supernatant was completely removed, the plates were stored at −70° C.

The plates were thawed and Molecular Probes CyQUANT (Molecular Probes) was added. Fluorescence was measured at 480 nm-520 nm.

The results are shown in FIG. 10.

Mutant CHO cell lines impaired in their glycosaminoglycan synthesis were used to verify the role of the proteoglycan in the cell adhesion to WISP-1. As shown in FIG. 10, none of the CHO cell lines completely deficient for the synthesis of glycosaminoglycan (CHO pgs A and CHO pgs B) were found to adhere to WISP-1. This result indicates that the adhesion of CHO cells to WISP-1 is totally dependent on the glycosaminoglycan side chains of the proteoglycan. On the other hand, CHO cell lines lacking heparan sulfate (CHO pgsD) or synthesizing an undersulfated heparan sulfate showed a 40% reduction in adhesion to WISP-1 compared to CHO-K1 that synthesize a normal proteoglycan. This shows that heparan sulfate proteoglycan of CHO cells is responsible only in part for the cell adhesion to WISP-1 and that its sulfation is necessary for its activity. Consequently, the dermatan sulfate proteoglycan which is the remaining fraction of the proteoglycan of CHO pgs D and CHO pgs E should be responsible for most of the adhesion of CHO cells to WISP-1.

Example 3

Adhesion of Human Skin Fibroblasts to WISP-1 and Other ECM Proteins

Human Skin Fibroblasts (ATCC; CRL 7356) were maintained in Ham-F12/LGDMEM (50:50) containing 10% FBS. Maxisorp plates were coated with 50 µl of the proteins (identified below) in solution in PBS at 4° C. overnight:

| | | |
|---|---|---|
| Collagen I, Human | (2 µg/ml) | (Human; BioDesign) |
| Collagen II, Human | (2 µg/ml) | (Human; BioDesign) |
| mWISP-1-IgG | (2 µg/ml) | (see Example 1 above) |
| BSA | 3% | (Fraction V, fatty acid ultra-free; Boehringer Mannheim) |

The next day, the content of the wells was aspirated and the wells be saturated with 200 µl of PBS/3% BSA for 1 hour at room temperature. The cells were taken up in PBS containing 15 mM EDTA, and the clumps were broken up using a pipette. The cell suspension was filtered over a 45 µm filter and centrifuged at 1000 rpm for 10 minutes.

The supernatant was removed and the cells washed twice with serum free Ham-F12/LGDMEM (50:50) containing 1% BSA. The cells were resuspended at $3 \times 10^5$ cells/ml with serum free Ham-F12/LGDMEM (50:50) containing 1% BSA. 50 µl of serum free Ham-F12/LGDMEM (50:50)/1% BSA was then added, along with 100 µg/ml Dermatan sulfate (Chondroitin sulfate B from Porcine intestinal mucosa; Sigma); 100 µg/ml Heparin (Porcine intestinal mucosa; Sigma) or no addition. The plates were incubated for 15 minutes at room temperature. Then, 50 µl of cell suspension was added to each well and incubated 2 hours at 37° C. without lids. Subsequently, the wells were washed 3× with PBS. Staining was performed with crystal violet for 30 minutes. The plates were then washed in water. O.D. was measured at 570 nm.

Figure 11:
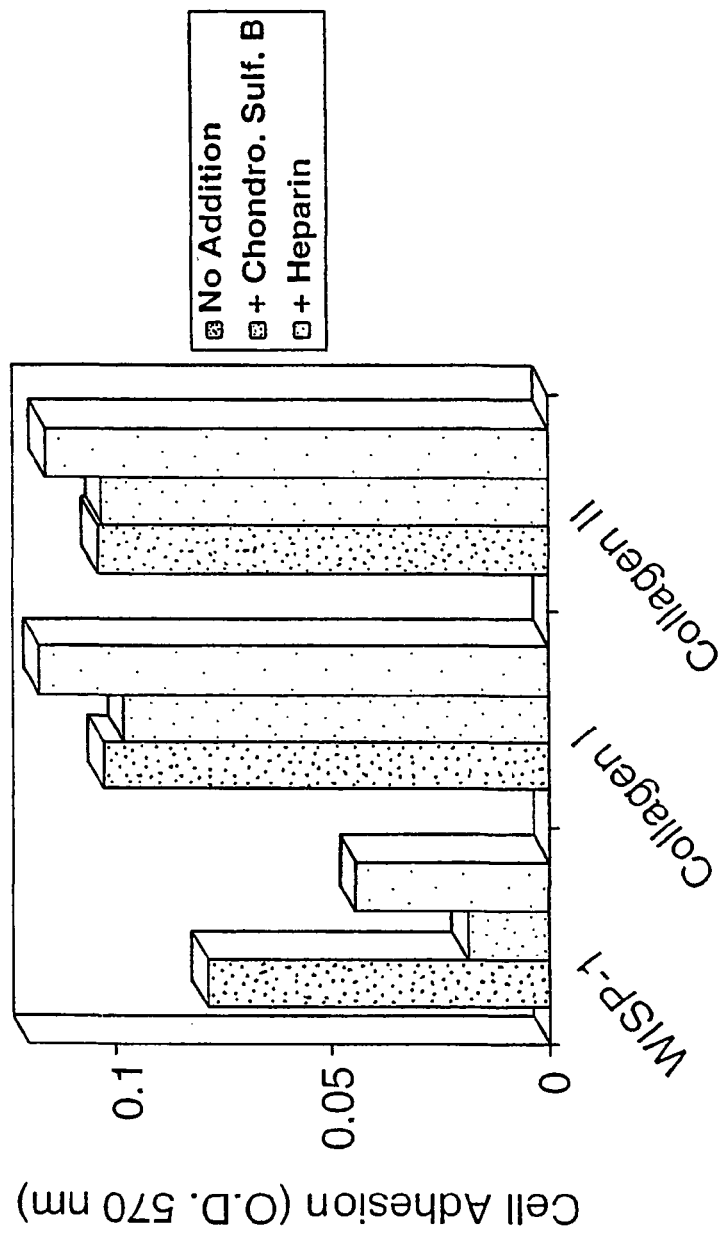
FIG. 11 shows the adhesion of human skin fibroblasts to WISP-1. Cells were taken up in PBS containing 15 mM EDTA and then washed and resuspended in serum free Ham-F12/LGDMEM (50:50) containing 1% BSA. Cell suspension was added to microtiter wells in the absence or the presence of 100 µg/ml of dermatan sulfate (i.e., chondroitin sulfate B) or heparin. After 2 hours at 37° C., the wells were washed 3× with PBS, the supernatant removed and the number of adherent cells measured by crystal violet staining. All values were corrected for nonspecific adhesion to microtiter wells coated with BSA.

The results are shown in FIG. 11.

The data suggests that although the value is lower than the positive controls (adhesion to collagen I and to collagen II) human skin fibroblasts adhere to wells coated with WISP-1 (FIG. 11). The presence of 100 µg/ml of heparin or 100 µg/ml dermatan sulfate reduced the cell adhesion to WISP-1 by 30% or 70% respectively. In similar conditions, the cell adhesion to collagen I and II did not significantly change. Those results indicate that the adhesion of human skin fibroblasts to WISP-1 is mediated through a different mechanism than the adhesion to collagen I and collagen II. It also indicates that while heparin containing proteoglycan can participate in this phenomenon, the adhesion of the human skin fibroblasts to WISP-1 is mainly mediated through dermatan sulfate proteoglycan.

Example 4

Chondrocyte Re-Differentiation Assay

An experiment was conducted to determine the effects of various concentrations of WISP-1 polypeptides on chondrocyte differentiation. In order to culture chondrocytes, articular cartilage is digested with enzymes which remove the extracellular matrix. Thus, the cellular environment in this culture system may be similar to that found in later stages of cartilage disorders where the matrix has been depleted and chondrocyte cells tend to revert back to an "immature" phenotype.

The metacarpophalangeal joints of 4-6 month old female pigs were aseptically dissected, and articular cartilage was removed by free-hand slicing taking care so as to avoid the underlying bone. These cartilage fragments were then digested in 0.05% trypsin in serum-free Ham's F12 for 25 minutes at 37° C. The medium was drained and discarded, and cartilage was digested in 0.3% collagenase B in serum-free Ham's F12 media for thirty minutes at 37° C. The medium was drained and discarded, and the cartilage was digested overnight in 0.06% collagenase B in Ham's F12+ 10% fetal bovine serum. The cells were then filtered through a 70 micron nylon filter and seeded in Ham's F12 medium without serum. The isolated cells are seeded at 25,000 cells/$cm^2$ in Ham F-12 containing 10% FBS and 4 µg/ml gentamycin. The culture media was changed every third day and the cells were re-seeded to 25,000 cells/$cm^2$ every five days. On day 12, the cells were seeded in 96 well plates at 5,000 cells/well in 100 μl of the same media without serum and 100 μl of human WISP-1-IgG (see FIG. 17), at 1% dilution, were added to give a final volume of 200 μl/well. After 5 days at 37° a picture of each well was taken using a stage driven inverted microscope. The differentiation state was morphologically determined using the Metamorph software from Universal Imaging Corporation. On each picture, round cells corresponding to re-differentiated chondrocytes are selected according to their size and shape whereas flattened cells having a dedifferentiated phenotype are eliminated. The total area covered by the selected cells on a picture is then calculated and compared to a positive control (redifferentiated chondrocytes by Staurosporin) and to a negative control (untreated cells).

The result calculation and interpretation were conducted as follows:

Result Calculation:

Y=Chondrocytes area

Redifferentiation index=[(Y-Y$_{negative\ control}$)/(Y$_{positive\ control}$-Y$_{negative\ control}$)]*100

Result Interpretation:

The greater the redifferentiation index, the better the WISP molecule will promote the chondrocytes to redifferentiate.

Result Cutoff: Redifferentiation index>40→positive result.

The results are shown in FIG. 12.

Example 5

Collagen II Staining Assay

Collagen II is a preferred marker for chondrocytes. After primary porcine chondrocytes are in culture for 10 days to "de-differentiate" into mesenchymal cells, the cells tend to loose their collagen II expression. The chondrocyte differentiation assay described above was conducted in which triplicate wells were treated for (+) and (−) controls and duplicates of each of the following proteins for 5 days:

| Positives | 5 nM (0.5 μl/50 ml) Staurosporin |
| | 100 nM IGF-1 |
| Negative | medium alone |
| Test | 100 nM human WISP-1-His |
| | 100 nM human WISP-2-His |
| | 100 nM human WISP-3-His |

(The WISP polypeptide constructs were prepared using a N-terminal His tag attached to each WISP polypeptide).

After the pictures are taken using the inverted microscope (as described in Example 4), the cells were fixed in 70% ethyl alcohol for 15 minutes at room temperature, and then washed 3× with PBS. The plates were blocked with PBS/3% BSA for 60 minutes at 200 μl/well. The treated wells were treated with mouse anti-Collagen II (Neomarker-5 B2.5) in PBS/3% BSA for 1 hour at room temperature, running a 1:2000 dilution. The plates were again washed 3× with PBS/0.1% BSA.

Following the wash, the plates were incubated with 1:1000 of Vector Biotinylated anti-Mouse in PBS/0.1% BSA for 30 minutes at room temperature. The plates were then washed 3× for 2 minutes in PBS.

The cells were fixed in 4% paraformaldehyde in PBS for 10 minutes at room temperature, and then washed with TBS (50 mM Tris-HCl, 150 mM NaCl, pH 8)+0.3%. BSA, 2× for 3 minutes (500 μl/well). Then, incubate with Dupont HRP-Streptavidin 1:1000 in TBS+1% BSA for 30 minutes (100 μl/well). This is followed by washes with TBS+0.1% BSA, 3× for 4 minutes (500 μl/well). Next, incubate with biotinylated tyramide for 10 minutes 1:50 in amplification diluent (NEN Dupont) (100 μl/well). Washes with TBS+0.1% BSA, 3× for 4 minutes (500 μl/well) followed the incubation.

In the next incubation, DAKO FITC-Streptavidin 1:1000 in TBS in HBS-C+1% BSA was added for 30 minutes (100 μl/well). Then, there was a brief wash in PBS. Finally, 1:1000 Hoechst in PBS (100 μl/well) was added, and then evaluated under an inverted microscope.

Figure 13:
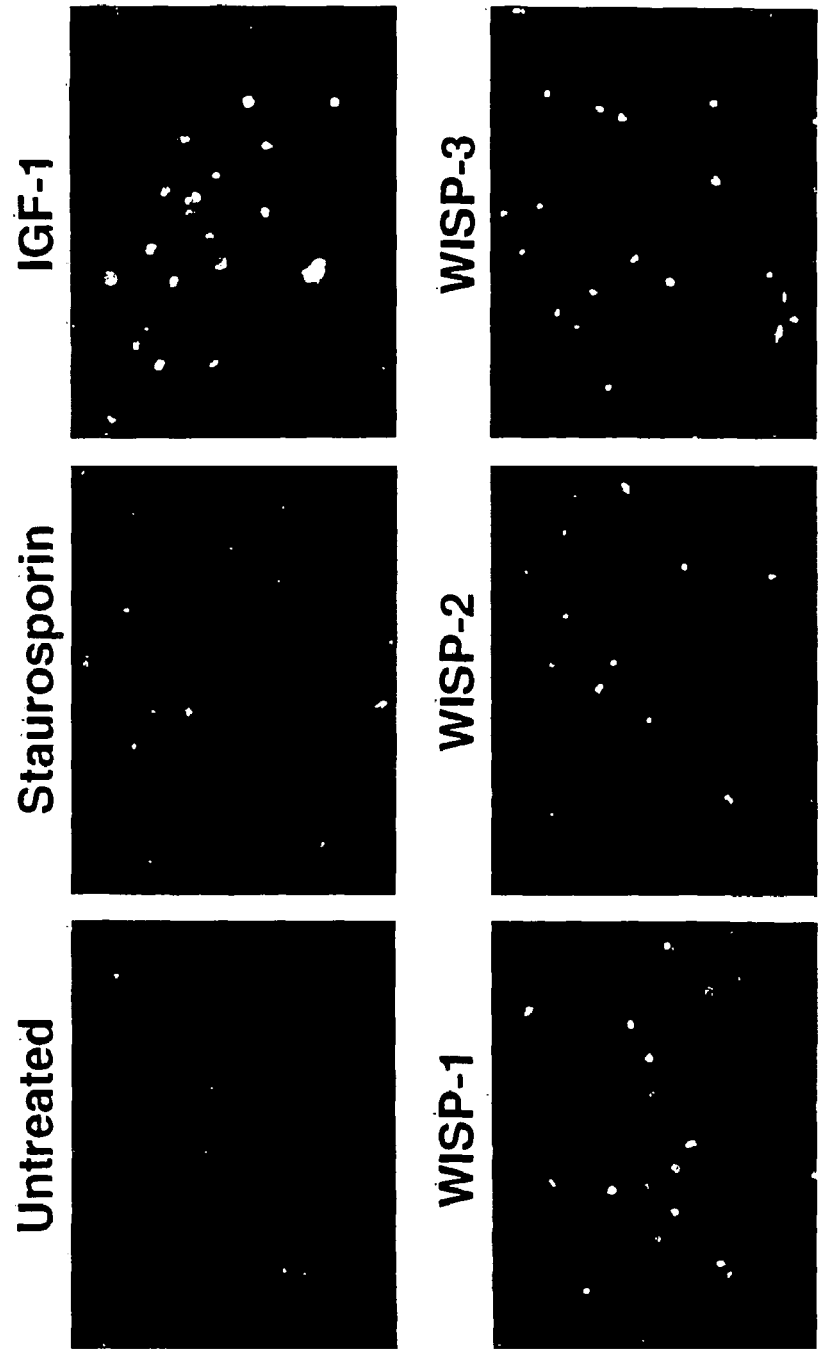
FIG. 13 shows the results of a collagen II staining assay.

The data are shown in FIG. 13. Positive controls (Staurosporin and IGF-1) stained strongly for collagen II while the negative control did not show any staining at all. Cells treated with 100 nM of WISP-1 or WISP-2 or WISP-3 showed a strong positive staining for collagen II. This data indicated that WISP proteins promote the redifferentiation of primary porcine chondrocytes in culture.

Example 6

Articular Cartilage Explant Assay

An experiment was conducted to examine both the synthetic and prophylactic potential of WISP polypeptides on cartilage matrix turnover. This potential is determined by measuring matrix (i.e proteoglycan) synthesis and breakdown, as well as nitric oxide production, in articular cartilage. These parameters are evaluated in the presence and absence of interleukin-1alpha. Articular cartilage explants have several advantages over primary cells in culture. First, and perhaps most importantly, cells in explants remain embedded in tissue architecture produced in vivo. Secondly, these explants are phenotypically stable for several weeks ex vivo, during which time they are able to maintain tissue homeostasis. Finally, unlike primary cells, explants can be used to measure matrix breakdown. To set up cartilage explants, articular cartilage must be dissected and minced which results in disruption of the collagen network and release of proteoglycans into the culture media. This system thus mimics degenerative conditions such as arthritis in which the matrix is progressively depleted.

The metacarpophalangeal joint of 4-6 month old female pigs was aseptically dissected as described above. The cartilage was minced, washed and cultured in bulk for at least 24 hours at 37° C. and 5% $CO_2$ in explant media, i.e. serum free (SF) LG DMEM/F12 media with 0.1% BSA, 100 U/ml penicillin/streptomycin (Gibco), 2 mM L-Glutamine, 0.1 mM sodium pyruvate (Gibco), 20 μg/ml Gentamicin (Gibco) and 1.25 mg/L Amphotericin B. Articular cartilage was aliquoted into micronics tubes (approximately 55 mg per tube) and incubated for at least 24 hours in the above media. Media was harvested and new media was added (alone or with WISP polypeptides (IgG-fusion constructs) at various time points (0, 24, 48 and 72 hours).

Media was harvested at various time points and then assayed for proteoglycan content using the 1,9-dimethylmethylene blue (DMMB) colorimetric assay of Farndale and Buttle, *Biochim. Biophys. Acta* 883: 173-177 (1985) as described above. PG release at 0 hours was used as a baseline measurement, and any samples with especially high or low PG release were discarded prior to treatment with WISP-1 polypeptide. For all treatments, results represent the average of 5 independent samples.

At 48 hours after the first treatment, $^{35}$S-sulfate was added to cartilage explants at a final concentration of 10 μCi/ml along with fresh media (with or without test compound). After an additional 12-17 hours of incubation at 37° C., the media was removed and saved for subsequent PG and nitric oxide (NO) analysis. The cartilage explants were washed twice with explant media and digested overnight at 50° C. in a 900 mL reaction volume of 10 mM EDTA, 0.1M sodium phosphate and 1 mg/ml proteinase K (Gibco BRL). The digestion reaction was mixed (2:1) with 10% w/v cetylpyridinium chloride (Sigma) to precipitate the proteoglycans and centrifuged at 1000×g for 15 minutes. The supernatant was removed and formic acid (500 ml, Sigma) was added to dissolve the pellets. The samples were then transferred to vials containing 10 ml scintillation fluid (ICN) and read in a scintillation counter.

After 72 hours, the remaining articular cartilage explants were digested as described above and assayed for proteoglycan content using the DMMB colorimetric assay (referenced above).

Figure 14:
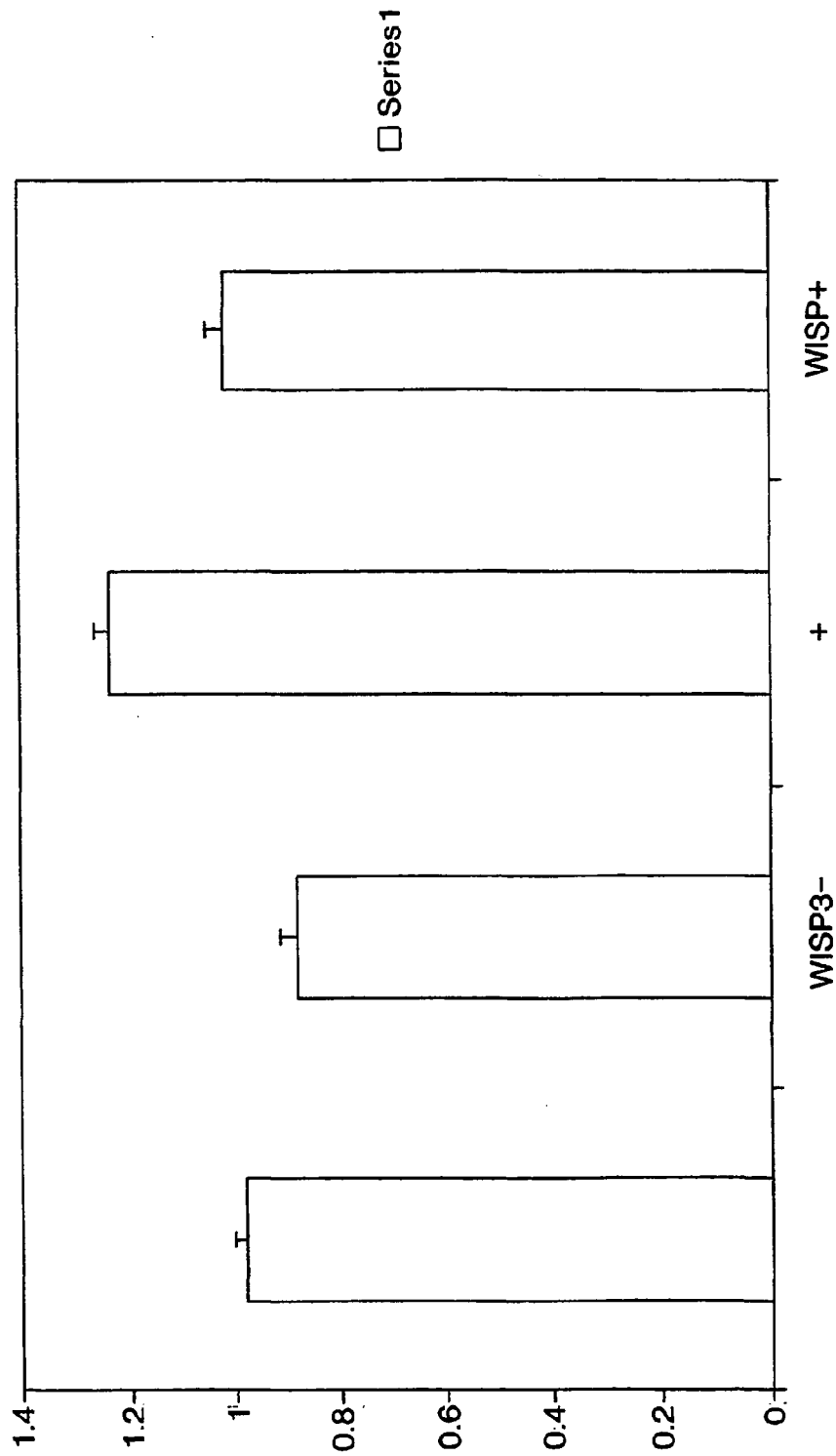
FIG. 14 shows the results of a cartilage matrix breakdown assay. The data illustrated shows that WISP-3 decreases cartilage matrix breakdown. Articular cartilage explants were treated with media alone (−)' or with 150 ng/ml WISP-3 ((WISP3—), or in media with IL-1alpha at 1 ng/ml alone (+) or IL-1alpha plus WISP-3 (WISP3+) for 3 days. Cartilage matrix breakdown was determined by measuring the amount of proteoglycans in the media using the DMMB assay.
Figure 15A:
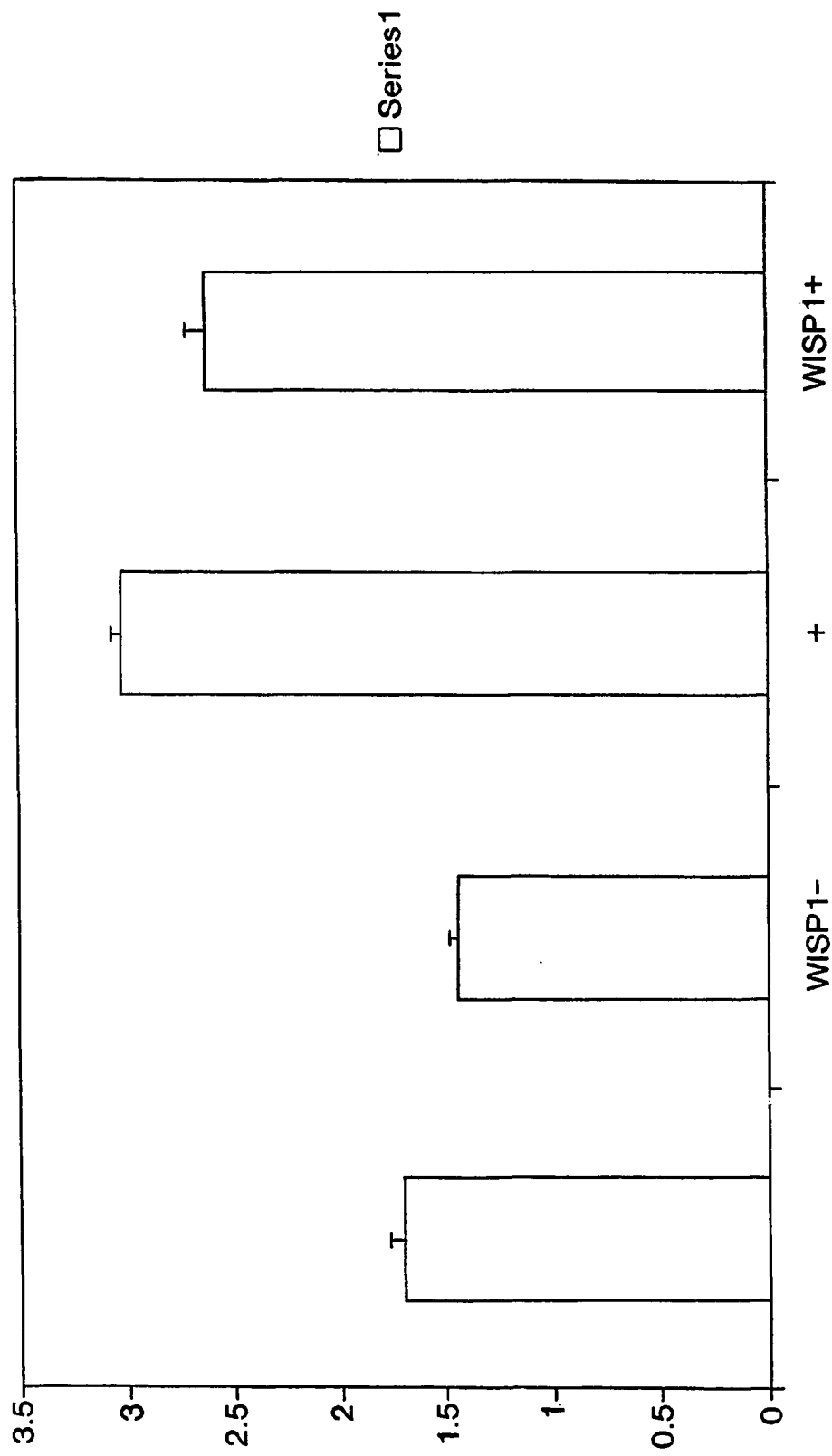
FIGS. 15A-15B show that WISP-1 inhibits cartilage matrix breakdown and production of nitric oxide. Articular cartilage explants were treated with media alone (−) or with 1.1 nM WISP-1 (WISP1−), or in media with IL-1alpha at 1 ng/ml alone (+) or IL-1alpha with WISP-1 (WISP1+) for 3 days.
Figure 15B:
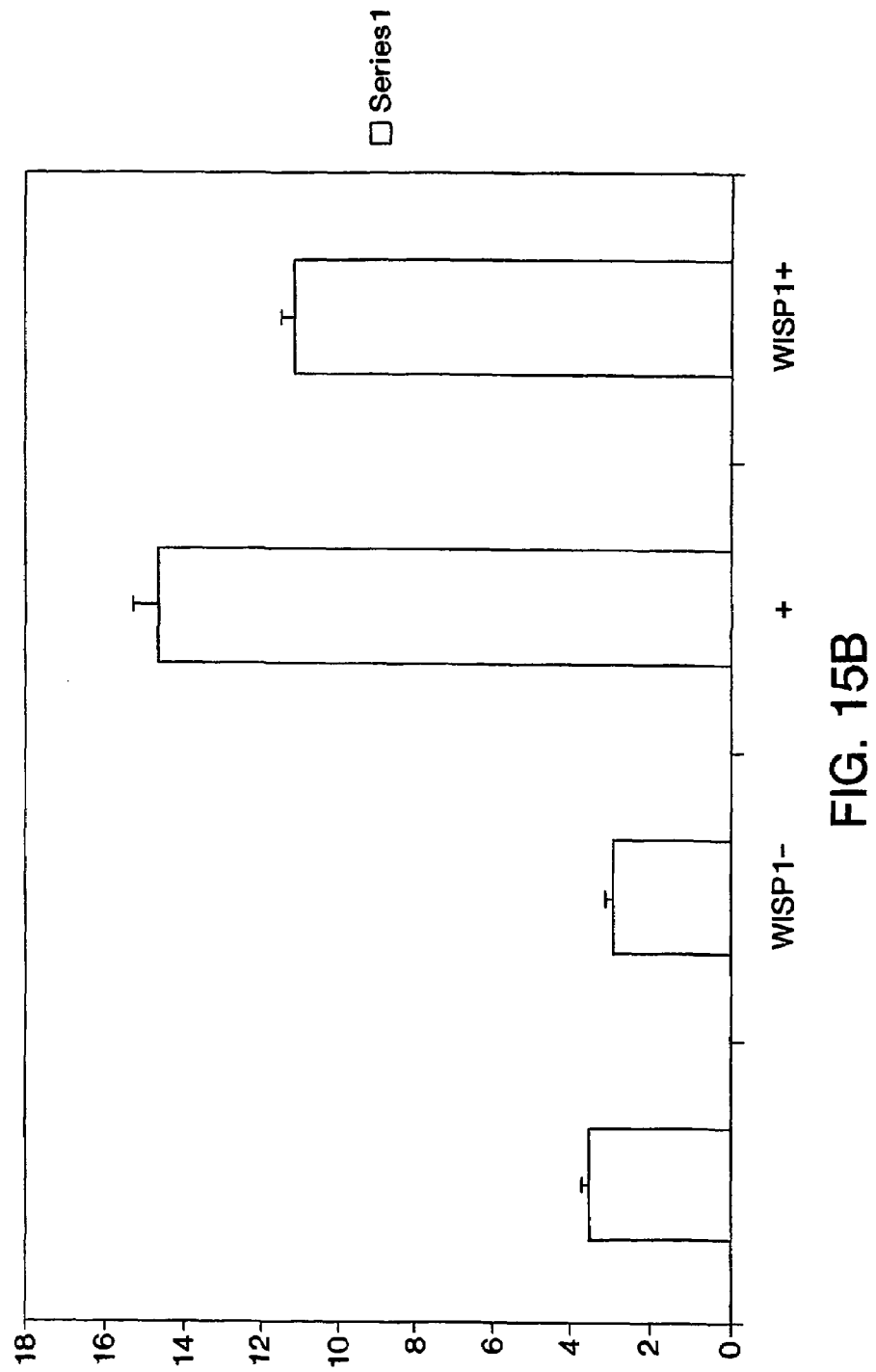

When articular cartilage explants were treated with either WISP-3 (FIG. 14) or WISP-1 (FIG. 15A), both basal and IL-1alpha induced cartilage matrix breakdown were decreased. In addition, WISP-1 inhibited both basal and IL-1alpha induced nitrix oxide production (FIG. 15B).

These results show that WISP polypeptides can protect against cartilage catabolism. Given the fact that elevated levels of both nitric oxide and IL-1alpha are found in diseased joints, the ability of WISP polypeptides to block activity of IL-1alpha and production of nitric oxide suggest that WISP polypeptides can decrease the extent of tissue damage in arthritic joints.

Example 7

Transgenic Mice Expressing WISP-2

To test the effect of WISP polypeptides in vivo, transgenic mice were created which overexpress WISP-2 in their muscle by virtue of the myosin light chain promoter. The transgenics were made using techniques known in the art (Manipulating the Mouse Embryo: A Laboratory Manual, Beddington et al., Cold Spring Harbor Press, 1994; Transgenic Animal Technology: A Laboratory Handbook, Academic Press, New York, 1994). The bones of these mice were examined at 14 weeks of age by standard histology. Following sacrifice of animals, bones were fixed in 4% buffered formalin, followed by decalcification in Formical™ for 4-8 hours. Samples were then processed for paraffin embedding and for histological assessment. Three-micron thick step sections were cut and stained with hematoxylin and eosin.

Figure 16:
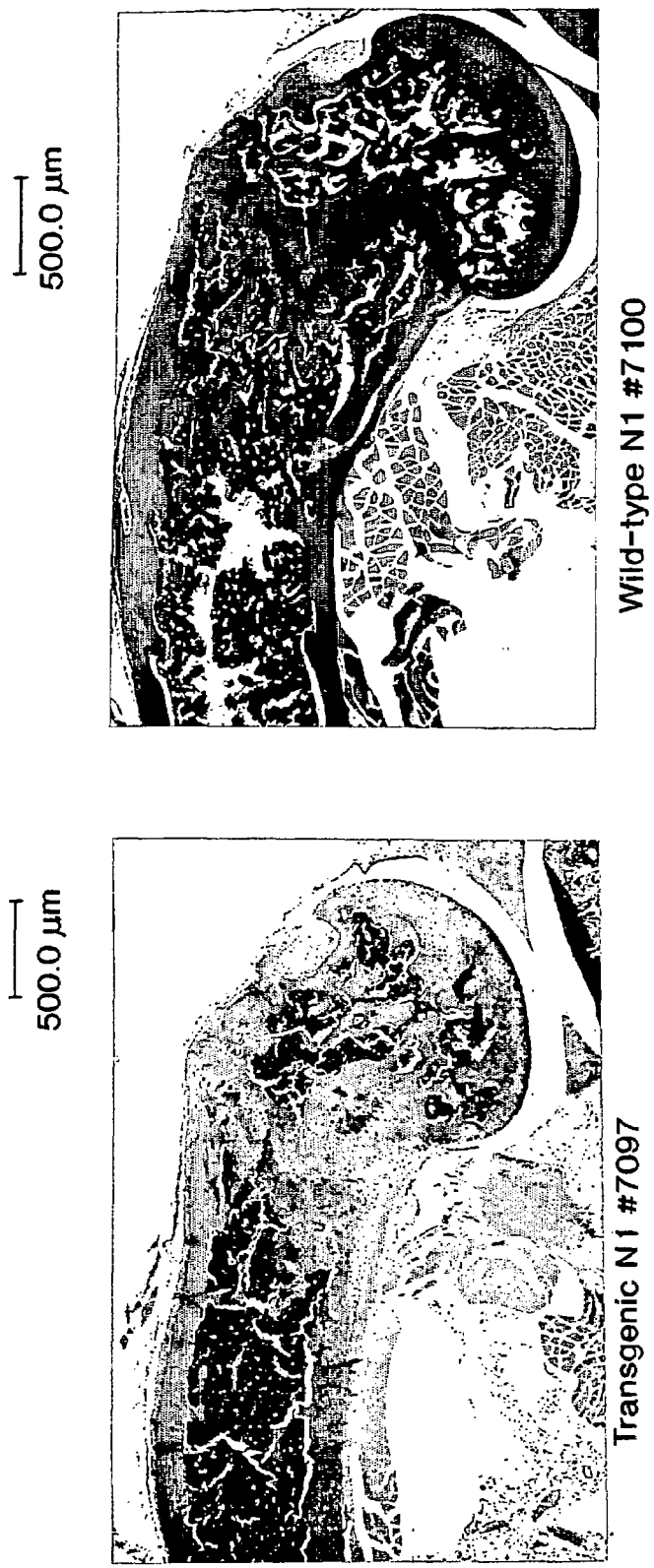
FIG. 16 shows the skeletal phenotype of transgenic mice which overexpress WISP-2. Histological sections of the femur of 14 week old wild-type (right panel) or transgenic (left panel) mice which overexpress WISP-2 in their skeletal muscle are shown. Note the expansion of the zones of hyaline cartilage, namely the growth plate and the articular cartilage, in the transgenic mice relative to those of the wild-type mice. In addition, areas of cartilage matrix appear to be present in the cortical bone of the transgenics, but not the wild-type mice.

As shown in FIG. 16, the hyaline cartilage compartments (i.e. the growth plate and the articular cartilage) appear to be expanded. These results are consistent with results presented in the Examples above showing the ability of WISP polypeptides to induce cartilage cell differentiation and inhibit cartilage matrix breakdown. Thus, WISP polypeptides can have potent effects on cartilage tissue in vivo. Treatment of an arthritic individual with a polypeptide having such activity, namely one which increases the amount of cartilage, may prevent the disability and joint destruction which can occur in arthritic patients.

What is claimed is:

1. A method of treating mammalian cartilage cells or mammalian cartilage tissue, comprising contacting mammalian cartilage cells or mammalian cartilage tissue damaged from a degenerative cartilagenous disorder with an effective amount of WISP polypeptide, wherein said WISP polypeptide is a polypeptide selected from the group consisting of:
   a) a WISP-1 polypeptide comprising amino acids 23 to 367 of SEQ ID NO:3;
   b) a WISP-1 polypeptide comprising amino acids 1 to 367 of SEQ ID NO:3; and
   c) a WISP-1 polypeptide having at least 95% identity to the polypeptide of a) or b), wherein said WISP-1 polypeptide stimulates chondrocyte proliferation or differentiation.

2. The method of claim 1 wherein said WISP-1 polypeptide comprises amino acids 23 to 367 of SEQ ID NO:3.

3. The method of claim 1 wherein said WISP-1 polypeptide is linked to one or more polyethylene glycol molecules.

4. The method of claim 1 wherein said WISP-1 polypeptide is linked to an epitope tag or immunoglobulin molecule.

5. The method of claim 1 wherein said cartilage cells or mammalian cartilage tissue is articular cartilage.

6. The method of claim 1 wherein the degenerative cartilagenous disorder is rheumatoid arthritis or osteoarthritis.

7. The method of claim 6 wherein the degenerative cartilagenous disorder is rheumatoid arthritis.

8. The method of claim 1 wherein the mammalian cartilage cells or mammalian cartilage tissue is contacted with the effective amount of the WISP polypeptide in vivo.

9. The method of claim 1 wherein the WISP polypeptide is included in a pharmaceutically acceptable carrier.

10. A method of treating mammalian cartilage cells or mammalian cartilage tissue, comprising contacting mammalian cartilage cells or mammalian cartilage tissue damaged from injury with an effective amount of WISP polypeptide, wherein said WISP polypeptide is a polypeptide selected from the group consisting of:

a) a WISP-1 polypeptide comprising amino acids 23 to 367 of SEQ ID NO:3;
b) a WISP-1 polypeptide comprising amino acids 1 to 367 of SEQ ID NO:3; and
c) a WISP-1 polypeptide having at least 95% identity to the polypeptide of a) or b), wherein said WISP-1 polypeptide stimulates chondrocyte proliferation or differentiation.

11. The method of claim 10 wherein the injury is a microdamage or blunt trauma, a chondral fracture, an osteochondral fracture or damage to meniscus, tendon or ligament.

12. The method of claim 10 wherein said WISP polypeptide is administered to a mammal by injection into said cartilage cells or mammalian cartilage tissue or a joint of the mammal.

13. The method of claim 10 wherein said WISP-1 polypeptide comprises amino acids 23 to 367 of SEQ ID NO:3.

14. The method of claim 10 wherein said WISP-1 polypeptide is linked to one or more polyethylene glycol molecules.

15. The method of claim 10 wherein said WISP-1 polypeptide is linked to an epitope tag or immunoglobulin molecule.

16. The method of claim 10 wherein the mammalian cartilage cells or mammalian cartilage tissue is contacted with the effective amount of the WISP polypeptide in vivo.

17. The method of claim 16 wherein the WISP polypeptide is included in a pharmaceutically acceptable carrier.

* * * * *